(12) United States Patent
Abdel-Wahab et al.

(10) Patent No.: US 10,202,427 B2
(45) Date of Patent: Feb. 12, 2019

(54) ESCULENTIN-2CHA PEPTIDE AND ANALOGUES THEREOF

(71) Applicant: UNIVERSITY OF ULSTER, Coleraine, County Londonderry (GB)

(72) Inventors: Yasser Abdel-Wahab, Coleraine (GB); Peter Flatt, Coleraine (GB); Opeolu Ojo, Coleraine (GB); J. Michael Conlon, Coleraine (GB)

(73) Assignee: UNIVERSITY OF ULSTER, Coleraine (GB)

( * ) Notice: Subject to any disclaimer, the term of this patent is extended or adjusted under 35 U.S.C. 154(b) by 0 days.

(21) Appl. No.: 15/115,532

(22) PCT Filed: Feb. 2, 2015

(86) PCT No.: PCT/EP2015/052094
§ 371 (c)(1),
(2) Date: Jul. 29, 2016

(87) PCT Pub. No.: WO2015/114148
PCT Pub. Date: Aug. 6, 2015

(65) Prior Publication Data
US 2017/0166614 A1    Jun. 15, 2017

(30) Foreign Application Priority Data
Jan. 31, 2014  (GB) .................................. 1401673.7

(51) Int. Cl.
*A61K 38/00*    (2006.01)
*C07K 14/46*    (2006.01)

(52) U.S. Cl.
CPC ............ *C07K 14/463* (2013.01); *A61K 38/00* (2013.01)

(58) Field of Classification Search
CPC .................................................. C07K 14/463
See application file for complete search history.

(56) References Cited

FOREIGN PATENT DOCUMENTS

| WO | WO 2000/09553 A2 | 2/2000 |
|---|---|---|
| WO | WO 2005/047316 A2 | 5/2005 |

OTHER PUBLICATIONS

Hermansen, Diabetes Care 29:1269-1274, 2006.*
Attoub, Esculentin-2CHa: A host-defense peptide with differential cytotoxicity against bacteria, erythrocytes and tumor cells, Peptides 2013, 39:95-102, available online Nov. 16, 2012, of record (Year: 2012).*
Roux, Elimination and exchange of trifluoroacetate counter-ion from cationic peptides: a critical evaluation of different approaches, J. Pept. Sci. 2008; 14: 354-359R, of record (Year: 2008).*
Hong, Effect of D-Amino Acid Substitution on the Stability, the Secondary Structure, and the Activity of Membrane-Active Peptide, Biochemical Pharmacology 1999, vol. 58, of record (Year: 1999).*
Malina, Conjugation of fatty acids with different lengths modulates the antibacterial and antifungal activity of a cationic biologically inactive peptide, Biochem. J. 2005, 390:695-702, of record (Year: 2005).*
Attoub et al., "Esculentin-2CHa: A host-defense peptide with differential cytotoxicity against bacteria, erythrocytes and tumor cells," *Peptides* 39: 95-102 (Nov. 16, 2012).
Conlon et al., "Characterization of antimicrobial peptide in skin secretions from discrete populations of *Lithobates chiricahuenis* (Ranidae) from central and southern Arizona," *Peptides* 32(4): 664-669 (Jan. 5, 2011).
International Search Report from parent PCT Application No. PCT/EP2015/052094, 5 pages (dated Apr. 8, 2015).
Marenah et al., "Skin secretions of *Rana saharica* frogs reveal antimicrobial peptides esculentines-1 and -1B and brevinins-1E and -2EC with novel insulin releasing activity," *Journal of Endocrinology* 188(1): 1-9 (Jan. 2006).
Written Opinion from parent PCT Application No. PCT/EP2015/052094, 8 pages (dated Apr. 8, 2015).

* cited by examiner

*Primary Examiner* — Lianko G Garyu
*Assistant Examiner* — Khalid Kader
(74) *Attorney, Agent, or Firm* — Klarquist Sparkman, LLP

(57) ABSTRACT

The present invention relates to an esculentin-2CHa peptide and analogs thereof, and the use each thereof in the treatment of diabetes, for example type 2 diabetes; insulin resistance; obesity, and/or hypercholesterolemia. Also disclosed is a pharmaceutical composition comprising peptides and analogs according to the present invention; use of peptides and analogs according to the present invention for the manufacture of a medicament for the treatment of diabetes, insulin resistance, obesity, and/or hypercholesterolemia; and methods of treating diabetes, insulin resistance, obesity, and/or hypercholesterolemia.

18 Claims, 49 Drawing Sheets
Specification includes a Sequence Listing.

Figure 2
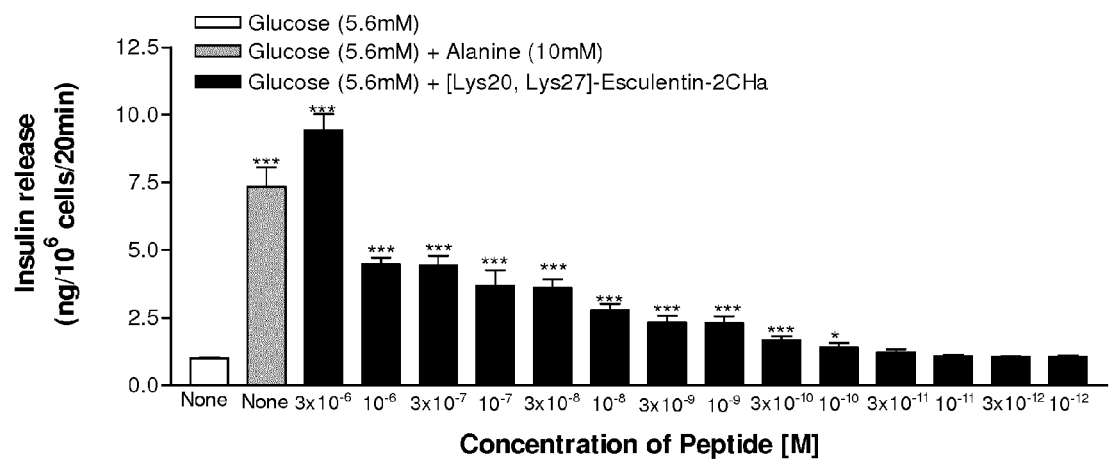
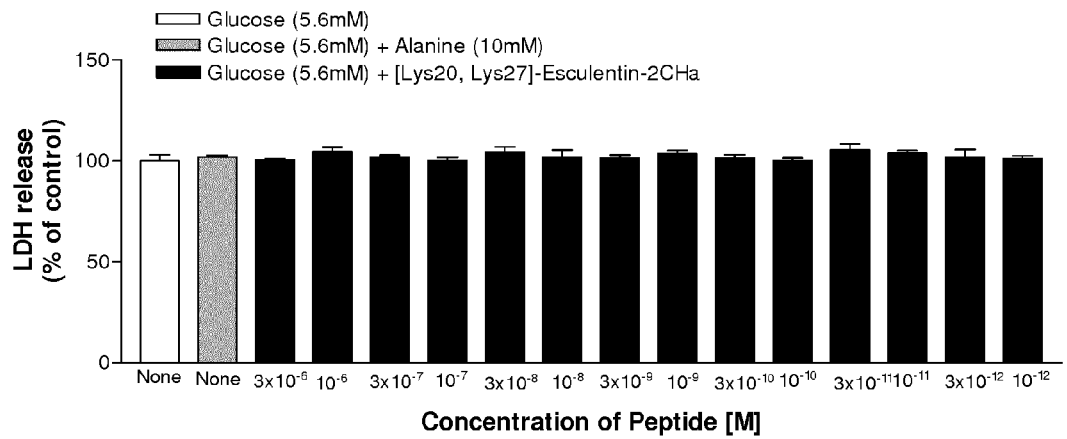

Figure 16
(A)
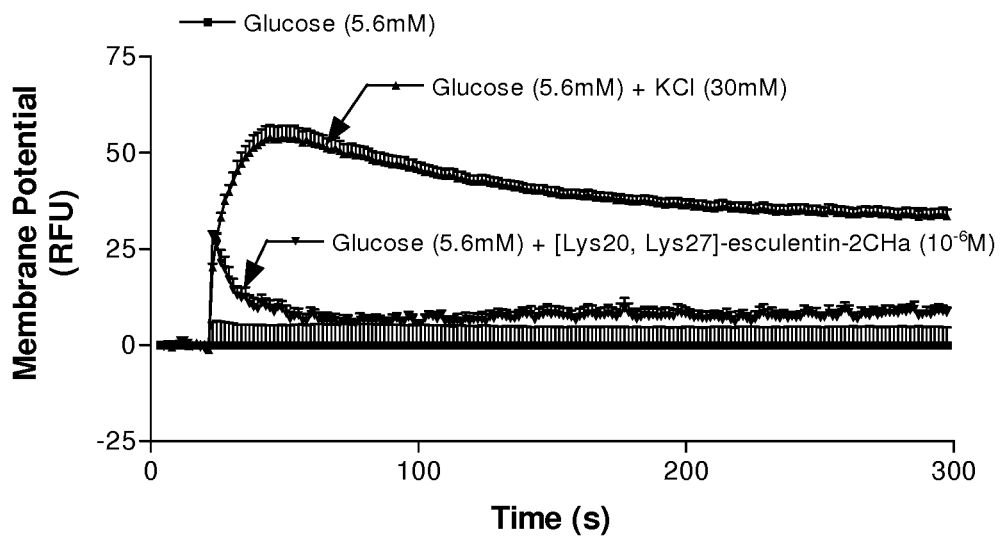
(B)
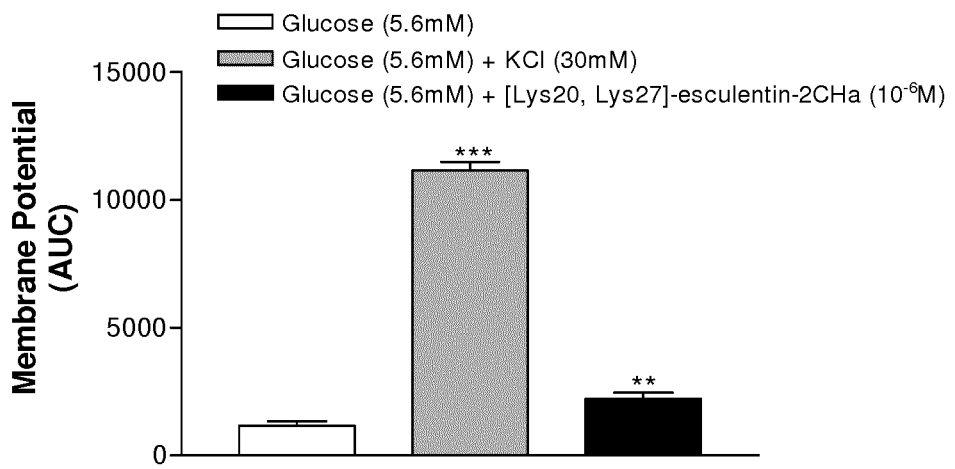

Figure 17
(A)
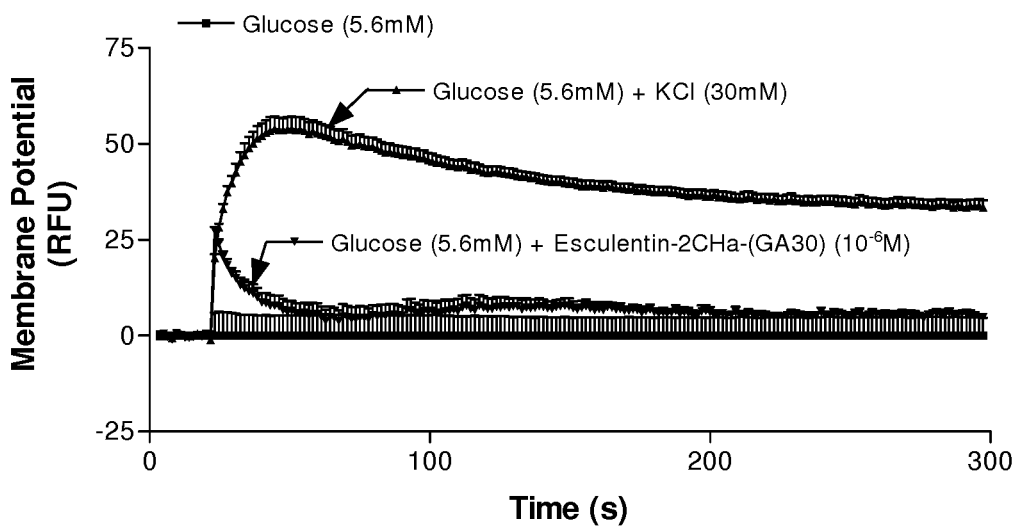
(B)
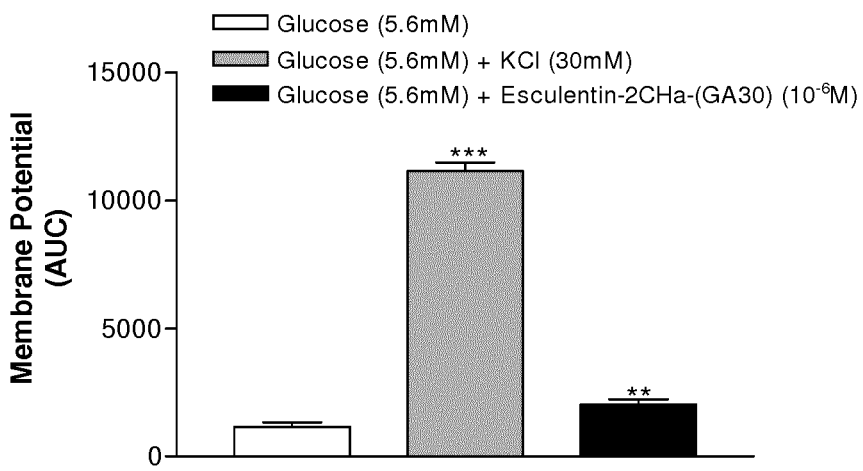

Figure 24
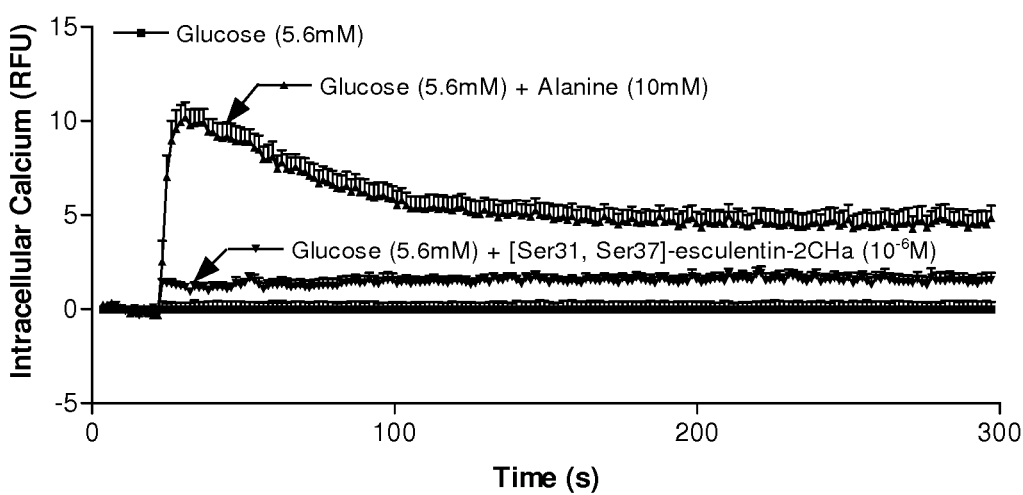
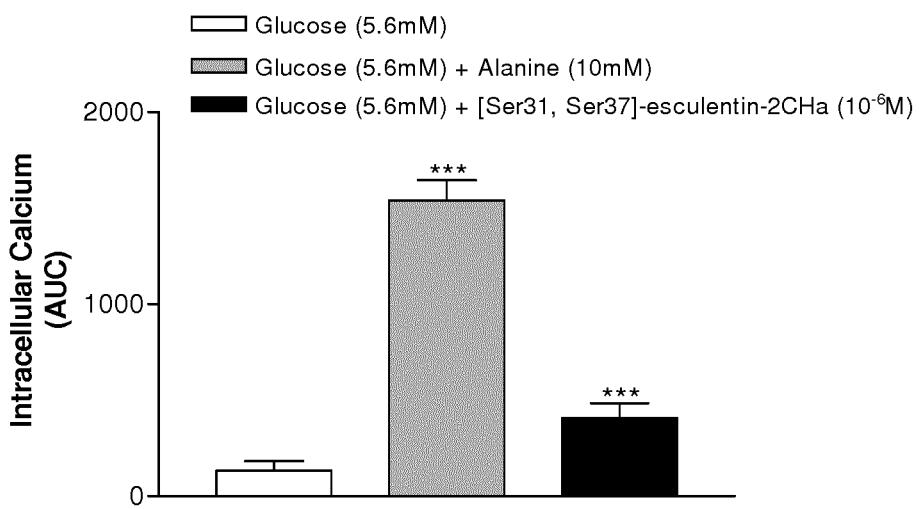

Figure 26
(A)
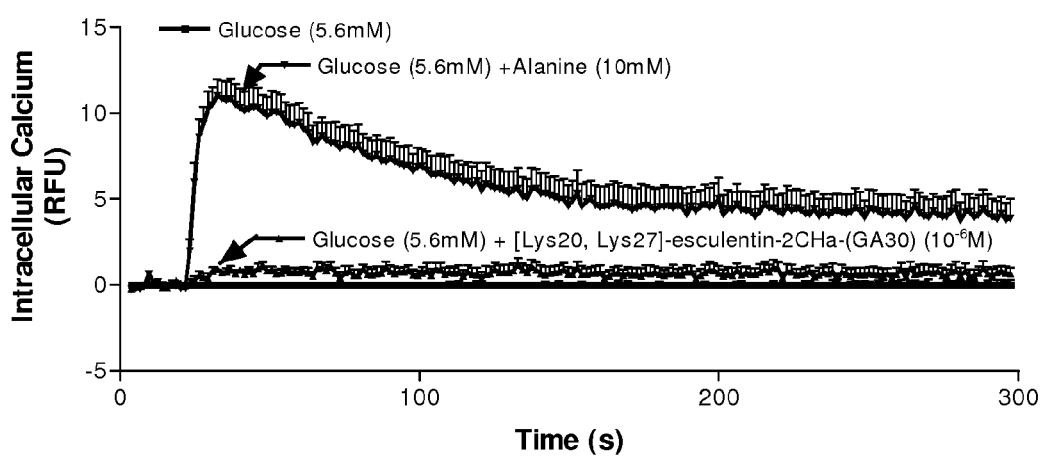
(B)
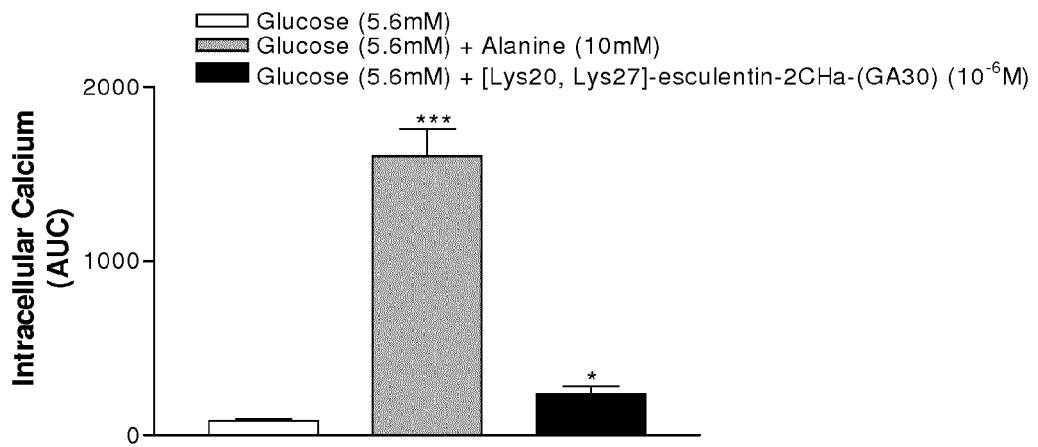

Figure 39

| Name of peptide | Primary sequence |
|---|---|
| Native esculentin-2CHa | GFSSIFRGVAKFASKGLGKDLAKLGVDLVACKISKQC |
| Esculentin-2CHa-(GA30) | GFSSIFRGVAKFASKGLGKDLAKLGVDLVA |
| [D-Arg$^7$]-esculentin-2CHa-(GA30) | GFSSIFrGVAKFASKGLGKDLAKLGVDLVA |
| [D-Lys$^{15}$]-esculentin-2CHa-(GA30) | GFSSIFRGVAKFASkGLGKDLAKLGVDLVA |
| [D-Lys$^{23}$]-esculentin-2CHa-(GA30) | GFSSIFRGVAKFASKGLGKDLAkLGVDLVA |
| [D-Lys$^{15}$,D-Lys$^{23}$]-esculentin-2CHa-(GA30) | GFSSIFRGVAKFASkGLGKDLAkLGVDLVA |
| [D-Arg$^7$, D-Lys$^{15}$,D-Lys$^{23}$]-esculentin-2CHa-(GA30) | GFSSIFrGVAKFASkGLGKDLAkLGVDLVA |
| [L-Orn$^{15}$, L-Orn$^{23}$]-Esculentin-2CHa-(GA30) | GFSSIFRGVAKFASOrnGLGKDLAOrnLGVDLVA |
| Esculentin-2CHa-(GA30)-NH$_2$ | GFSSIFRGVAKFASKGLGKDLAKLGVDLVA-NH$_2$ |
| Lys$^{15}$-octanoate -Esculentin-2CHa-(GA30) | GFSSIFRGVAKFASK(Oct)GLGKDLAKLGVDLVA |
| Lys$^{23}$-octanoate -Esculentin-2CHa-(GA30) | GFSSIFRGVAKFASKGLGKDLAK(Oct)LGVDLVA |
| [Lys$^{20}$,Lys$^{27}$]-esculentin-2CHa-(GA30) | GFSSIFRGVAKFASKGLGKKLAKLGVKLVA |
| [Lys$^{20}$,Lys$^{27}$]-esculentin-2CHa | GFSSIFRGVAKFASKGLGKKLAKLGVKLVACKISKQC |
| [Ser$^{31}$,Ser$^{37}$]-esculentin-2CHa | GFSSIFRGVAKFASKGLGKDLAKLGVDLVASKISKQS |
| [Lys$^{20}$,Lys$^{27}$,Ser$^{31}$,Ser$^{37}$]-esculentin-2CHa | GFSSIFRGVAKFASKGLGKKLAKLGVKLVASKISKQS |

Figure 43
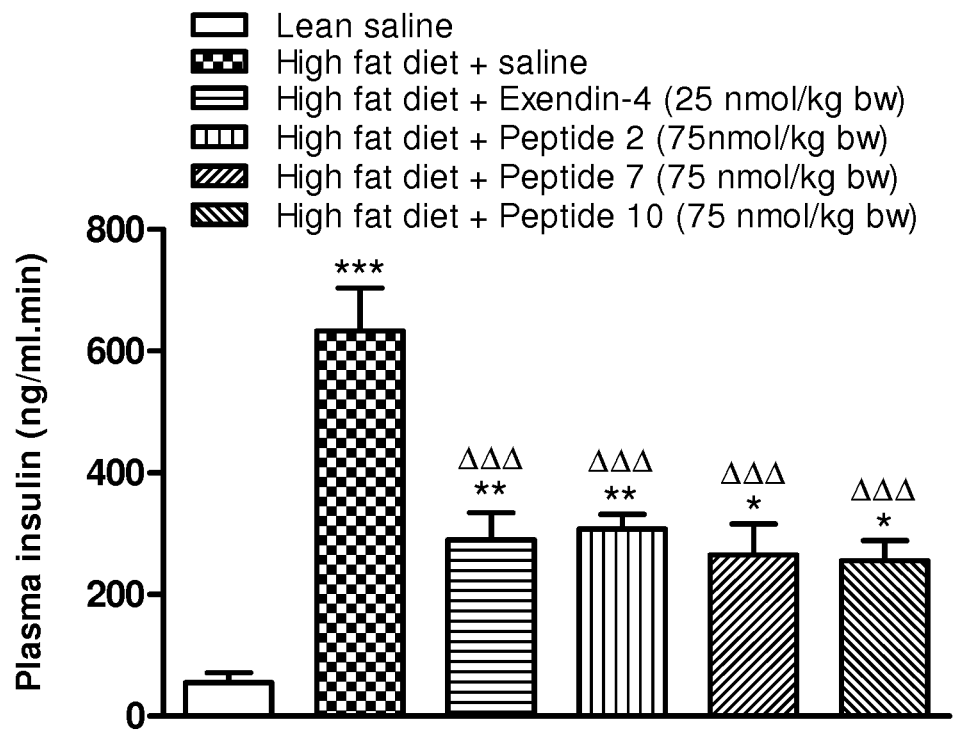
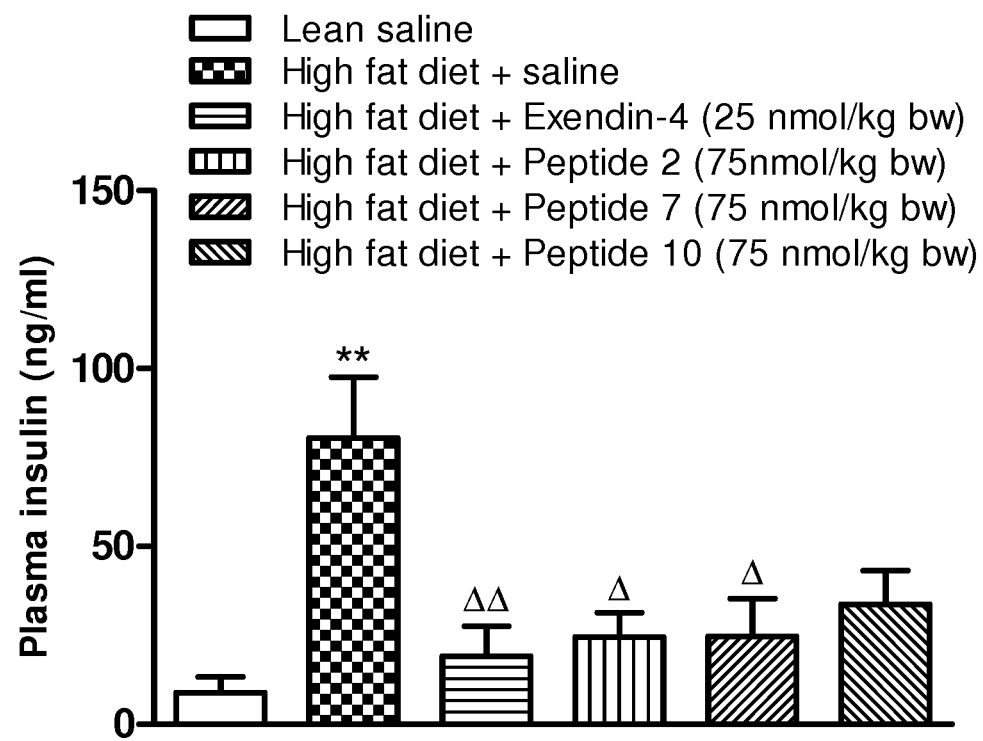

Figure 49
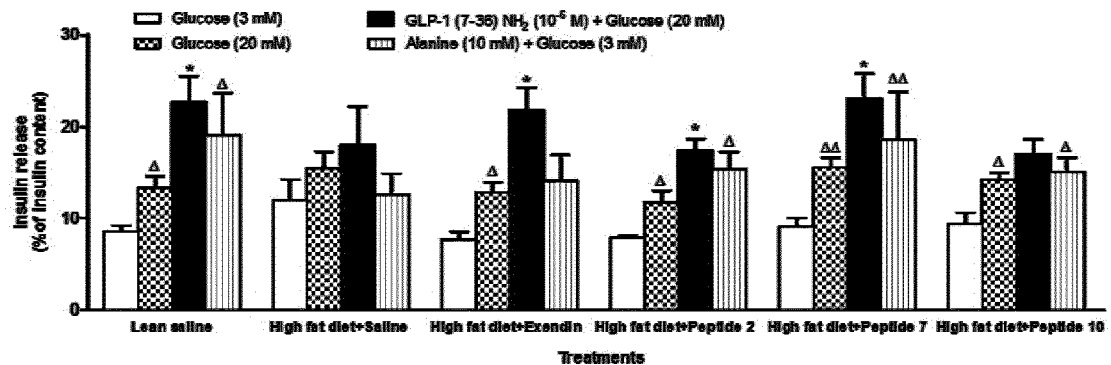
Figure 50A
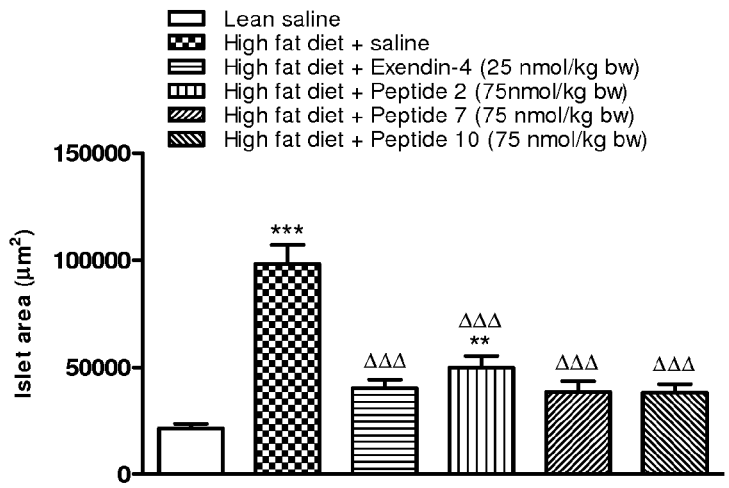
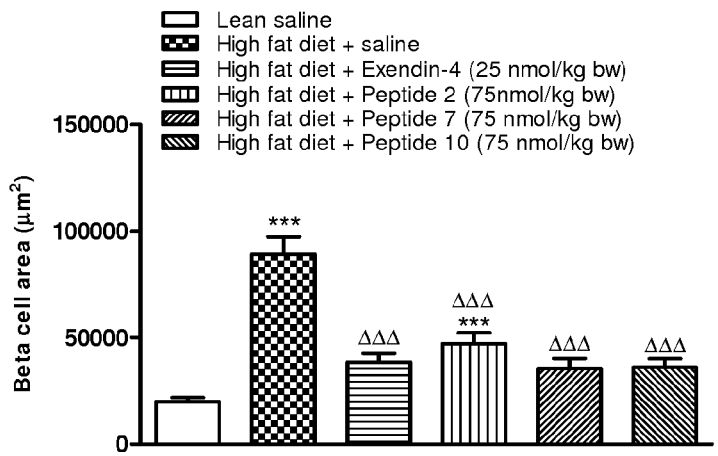

Figure 52B
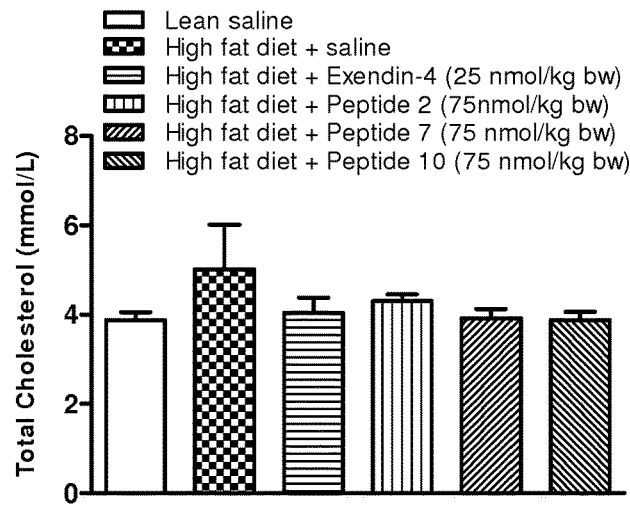
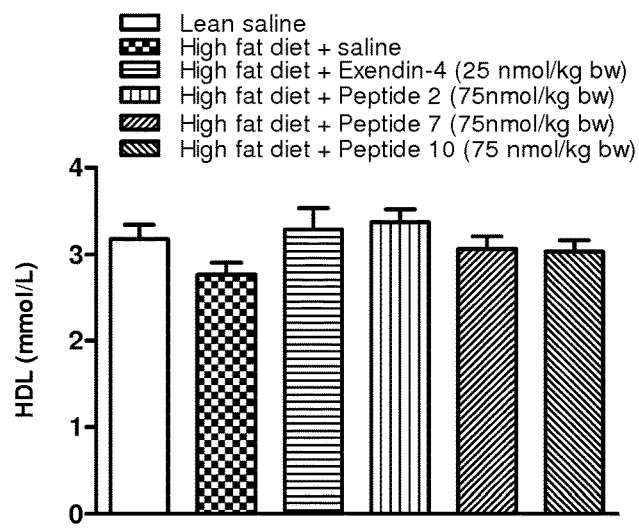
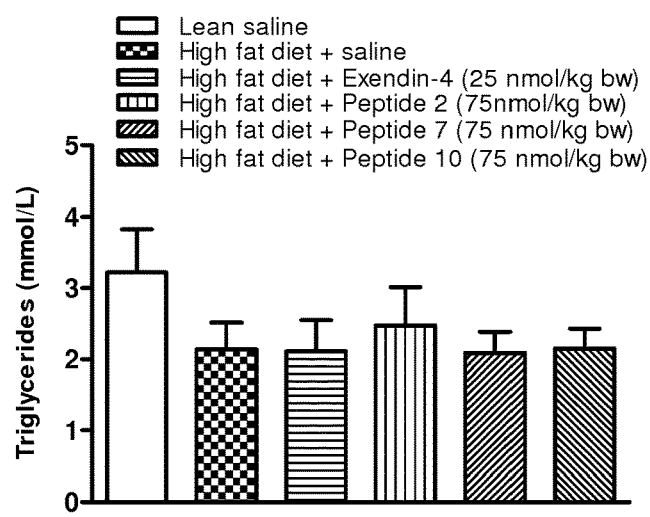

US 10,202,427 B2

ESCULENTIN-2CHA PEPTIDE AND ANALOGUES THEREOF

CROSS REFERENCE TO RELATED APPLICATIONS

This is a § 371 U.S. national stage of international Application No. PCT/EP2015/052094, filed Feb. 2, 2015, which was published in English under PCT Article 21(2), which claims priority to Great Britain Application No. 1401673.7, filed Jan. 31, 2014.

FIELD OF THE INVENTION

This invention relates to an esculentin-2CHa peptide and analogues thereof, and the use each thereof in the treatment of diabetes, for example type 2 diabetes; insulin resistance; obesity, and/or hypercholesterolemia.

BACKGROUND OF THE INVENTION

Currently, there is a global pandemic of diabetes mellitus with an estimated 220 million sufferers worldwide; 3 million of which are presently in the United Kingdom. Worst still, there are close to 1 million yet-to-be-diagnosed cases in the United Kingdom alone, and many more worldwide. Type 2 diabetes constitutes about 95% of all cases of diabetes. As the incidence of the disease increases, so does the cost of its treatment. In the United Kingdom, the cost of diabetes treatment and management of complications arising from the disease accounts for about 10% of the National Health Service (NHS) budget (GBP 9.8 billion). This cost is likely to rise to an estimated GBP 16.9 billion by 2035. Several factors have contributed to the epidemic nature of the disease. These include increased sedentary lifestyle, population growth, and increased incidence of obesity. Defective insulin secretion and action, resulting in elevated plasma glucose, represent major metabolic derangements that characterize type 2 diabetes. Unfortunately, there is no cure yet for the disease, nor is there any therapeutic agent that can reinstate normal glucose metabolism in people suffering from diabetes. Most of the clinically available anti-diabetic drugs have inefficiencies, such as obvious side effects and short half-life. Further, although there are currently several drugs for the treatment of diabetes, none of these therapeutic options has adequately addressed unmet needs in non-insulin treatment of the disease, and there is clearly an unmet need for novel therapeutics agents.

Oral anti-diabetic medications currently used in the treatment of type 2 diabetes include biguanides (such as metformin), sulphonylureas (such as tolbutamide, acetohexamide, tolazamide, chlorpropamide, glipizide, glibenclamide, glimepiride, gliclazide, glycopyramide, and gliquidone), thiazolidinediones (such as rosiglitazone, pioglitazone, and trogiitazone), meglitinides (such as repaglinide and nateglinide) alpha-glucosidase inhibitors (such as miglitol, acarbose, and voglibose) and dipeptidyl peptidase-4 inhibitors (such as vildagliptian, sitagliptian, saxagliptian, linagliptin, allogliptin, and septagliptin). However, for many patients, these oral medications, both in isolation and in combination with one another, are unable to control metabolic derangements that characterize type 2 diabetes. In advanced cases, the use of injectable medication is required (in combination with the oral medication). The above problems associated with type 2 diabetes mean there is an urgent need for alternative treatments for this condition.

SUMMARY OF THE INVENTION

According to a first aspect of the present invention, there is provided an esculentin-2CHa peptide or analogue thereof, comprising at least 30 amino acid residues corresponding to at least the first 30 amino acids from the N-terminal end of the esculentin-2CHa peptide.

Optionally, the peptide or peptide analogue comprises 30 amino acid residues corresponding to at least the first 30 amino acids from the N-terminal end of the esculentin-2CHa peptide. Further optionally, the peptide or peptide analogue consists of 30 amino acid residues corresponding to at least the first 30 amino acids from the N-terminal end of the esculentin-2CHa peptide.

Optionally, the peptide or peptide analogue further comprises at least one amino acid substitution or modification selected from the group comprising, or consisting of:
- an amino acid substitution or modification at position 7;
- an amino acid substitution or modification at position 15;
- an amino acid substitution or modification at position 20;
- an amino acid substitution or modification at position 23;
- an amino acid substitution or modification at position 27; and
- an amino acid substitution or modification at position 30.

Optionally, the peptide or peptide analogue comprises at least 37 amino acid residues corresponding to at least the first 37 amino acids from the N-terminal end of the esculentin-2CHa peptide.

Optionally, the peptide or peptide analogue comprises 37 amino acid residues corresponding to at least the first 37 amino acids from the N-terminal end of the esculentin-2CHa peptide. Further optionally, the peptide or peptide analogue consists of 37 amino acid residues corresponding to at least the first 37 amino acids from the N-terminal end of the esculentin-2CHa peptide.

Optionally, the peptide or peptide analogue further comprises at least one amino acid substitution or modification selected from the group comprising, or consisting of:
- an amino acid substitution or modification at position 31; and
- an amino acid substitution or modification at position 37.

Optionally, the amino acid substitution at position 7 is substitution with the D-isomer of arginine (D-Arg).

Optionally or additionally, the amino acid substitution or modification at position 15 is selected from at least one of the group comprising, or consisting of:
- substitution with the D-isomer of lysine (D-Lys);
- substitution with ornithine, optionally L-ornithine; and
- modification by addition of a fatty acid to the amino acid residue, optionally wherein the fatty acid is a medium-chain fatty acid having 6-12 carbon atoms, further optionally wherein the medium-chain fatty acid is a C-8 fatty acid, still further optionally wherein the C-8 fatty acid is octanoate.

Optionally or additionally, the amino acid substitution at position 20 is substitution with lysine (Lys).

Optionally or additionally, the amino acid substitution or modification at position 23 is selected from at least one of the group comprising, or consisting of:
- substitution with the D-isomer of lysine (D-Lys);
- substitution with ornithine, optionally L-ornithine; and
- modification by addition of a fatty acid to the amino acid residue, optionally wherein the fatty acid is a medium-chain fatty acid having 6-12 carbon atoms, further optionally wherein the medium-chain fatty acid is a C-8 fatty acid, still further optionally wherein the C-8 fatty acid is octanoate.

Optionally or additionally, the amino acid substitution at position 27 is substitution with lysine (Lys).

Optionally or additionally, the amino acid modification at position 30 is addition of an amide group.

Optionally or additionally, the amino acid substitution at position 31 is substitution with serine (Ser).

Optionally or additionally, the amino acid substitution at position 37 is substitution with serine (Ser).

Optionally, the peptide or peptide analogue comprises 30 amino acid residues corresponding to the first 30 amino acids from the N-terminal end of the esculentin-2CHa peptide and an amino acid substitution or modification at position 7. Further optionally, the amino acid substitution or modification at position 7 is substitution with the D-isomer of arginine (D-Arg). Still further optionally, the peptide or peptide analogue consists of 30 amino acid residues corresponding to the first 30 amino acids from the N-terminal end of the esculentin-2CHa peptide and an amino acid substitution or modification at position 7. Still further optionally, the amino acid substitution or modification at position 7 is substitution with the D-isomer of arginine (D-Arg).

Optionally, the peptide or peptide analogue comprises 30 amino acid residues corresponding to the first 30 amino acids from the N-terminal end of the esculentin-2CHa peptide and an amino acid substitution or modification at position 15. Further optionally, the amino acid substitution or modification at position 15 is substitution with the D-isomer of lysine (D-Lys). Still further optionally, the peptide or peptide analogue consists of 30 amino acid residues corresponding to the first 30 amino acids from the N-terminal end of the esculentin-2CHa peptide and an amino acid substitution or modification at position 15. Still further optionally, the amino acid substitution or modification at position 15 is substitution with the D-isomer of lysine (D-Lys).

Optionally or additionally, the peptide or peptide analogue comprises 30 amino acid residues corresponding to the first 30 amino acids from the N-terminal end of the esculentin-2CHa peptide and an amino acid substitution or modification at position 23. Further optionally, the amino acid substitution or modification at position 23 is substitution with the D-isomer of lysine (D-Lys). Still further optionally, the peptide or peptide analogue consists of 30 amino acid residues corresponding to the first 30 amino acids from the N-terminal end of the esculentin-2CHa peptide and an amino acid substitution or modification at position 23. Still further optionally, the amino acid substitution or modification at position 23 is substitution with the D-isomer of lysine (D-Lys).

Optionally, the peptide or peptide analogue comprises 30 amino acid residues corresponding to the first 30 amino acids from the N-terminal end of the esculentin-2CHa peptide and at least one of an amino acid substitution or modification at position 15 and an amino acid substitution or modification at position 23. Further optionally, the amino acid substitution or modification at position 15 is substitution with the D-isomer of lysine (D-Lys). Alternatively or additionally, the amino acid substitution or modification at position 23 is substitution with the D-isomer of lysine (D-Lys). Still further optionally, the peptide or peptide analogue consists of 30 amino acid residues corresponding to the first 30 amino acids from the N-terminal end of the esculentin-2CHa peptide and at least one of an amino acid substitution or modification at position 15 and an amino acid substitution or modification at position 23. Still further optionally, the amino acid substitution or modification at position 15 is substitution with the D-isomer of lysine (D-Lys). Alternatively or additionally, the amino acid substitution or modification at position 23 is substitution with the D-isomer of lysine (D-Lys).

Optionally, the peptide or peptide analogue comprises 30 amino acid residues corresponding to the first 30 amino acids from the N-terminal end of the esculentin-2CHa peptide and at least one of an amino acid substitution or modification at position 7; an amino acid substitution or modification at position 15; and an amino acid substitution or modification at position 23. Further optionally, the amino acid substitution or modification at position 7 is substitution with the D-isomer of arginine (D-Arg); the amino acid substitution or modification at position 15 is substitution with the D-isomer of lysine (D-Lys); and the amino acid substitution or modification at position 23 is substitution with the D-isomer of lysine (D-Lys). Still further optionally, the peptide or peptide analogue consists of 30 amino acid residues corresponding to the first 30 amino acids from the N-terminal end of the esculentin-2CHa peptide and at least one of an amino acid substitution or modification at position 7; an amino acid substitution or modification at position 15; and an amino acid substitution or modification at position 23. Still further optionally, the amino acid substitution or modification at position 7 is substitution with the D-isomer of arginine (D-Arg); the amino acid substitution or modification at position 15 is substitution with the D-isomer of lysine (D-Lys); and the amino acid substitution or modification at position 23 is substitution with the D-isomer of lysine (D-Lys).

Optionally, the peptide or peptide analogue comprises 30 amino acid residues corresponding to the first 30 amino acids from the N-terminal end of the esculentin-2CHa peptide and at least one of an amino acid substitution or modification at position 15 and an amino acid substitution or modification at position 23. Further optionally, the amino acid substitution or modification at position 15 is substitution with ornithine, optionally L-ornithine. Alternatively or additionally, the amino acid substitution or modification at position 23 is substitution with ornithine, optionally L-ornithine. Still further optionally, the peptide or peptide analogue consists of 30 amino acid residues corresponding to the first 30 amino acids from the N-terminal end of the esculentin-2CHa peptide and at least one of an amino acid substitution or modification at position 15 and an amino acid substitution or modification at position 23. Still further optionally, the amino acid substitution or modification at position 15 is substitution with ornithine, optionally L-ornithine. Alternatively or additionally, the amino acid substitution or modification at position 23 is substitution with ornithine, optionally L-ornithine.

Optionally, the peptide or peptide analogue comprises 30 amino acid residues corresponding to the first 30 amino acids from the N-terminal end of the esculentin-2CHa peptide and an amino acid modification at position 30. Further optionally, the amino acid modification at position 30 is addition of an amide group. Still further optionally, the peptide or peptide analogue consists of 30 amino acid residues corresponding to the first 30 amino acids from the N-terminal end of the esculentin-2CHa peptide and an amino acid modification at position 30. Further optionally, the amino acid modification at position 30 is addition of an amide group.

Optionally, the peptide or peptide analogue comprises 30 amino acid residues corresponding to the first 30 amino acids from the N-terminal end of the esculentin-2CHa peptide and an amino acid substitution or modification at position 15. Further optionally, the amino acid substitution or modification at position 15 is modification by addition of a fatty acid to the amino acid residue, optionally wherein the fatty acid is a medium-chain fatty acid having 6-12 carbon atoms, further optionally wherein the medium-chain fatty acid is a C-8 fatty acid, still further optionally wherein the C-8 fatty acid is octanoate. Still further optionally, the peptide or peptide analogue consists of 30 amino acid residues corresponding to the first 30 amino acids from the N-terminal end of the esculentin-2CHa peptide and an amino acid substitution or modification at position 15. Further optionally, the amino acid substitution or modification at position 15 is modification by addition of a fatty acid to the amino acid residue, optionally wherein the fatty acid is a medium-chain fatty acid having 6-12 carbon atoms, further optionally wherein the medium-chain fatty acid is a C-8 fatty acid, still further optionally wherein the C-8 fatty acid is octanoate.

Optionally, the peptide or peptide analogue comprises 30 amino acid residues corresponding to the first 30 amino acids from the N-terminal end of the esculentin-2CHa peptide and an amino acid substitution or modification at position 23. Further optionally, the amino acid substitution or modification at position 23 is modification by addition of a fatty acid to the amino acid residue, optionally wherein the fatty acid is a medium-chain fatty acid having 6-12 carbon atoms, further optionally wherein the medium-chain fatty acid is a C-8 fatty acid, still further optionally wherein the C-8 fatty acid is octanoate. Still further optionally, the peptide or peptide analogue consists of 30 amino acid residues corresponding to the first 30 amino acids from the N-terminal end of the esculentin-2CHa peptide and an amino acid substitution or modification at position 23. Further optionally, the amino acid substitution or modification at position 23 is modification by addition of a fatty acid to the amino acid residue, optionally wherein the fatty acid is a medium-chain fatty acid having 6-12 carbon atoms, further optionally wherein the medium-chain fatty acid is a C-8 fatty acid, still further optionally wherein the C-8 fatty acid is octanoate.

Optionally, the peptide or peptide analogue comprises 30 amino acid residues corresponding to the first 30 amino acids from the N-terminal end of the esculentin-2CHa peptide and at least one of an amino acid substitution or modification at position 20 and an amino acid substitution or modification at position 27. Further optionally, the amino acid substitution or modification at position 20 is substitution with lysine (Lys). Alternatively or additionally, the amino acid substitution or modification at position 27 is substitution with lysine (Lys). Still further optionally, the peptide or peptide analogue consists of 30 amino acid residues corresponding to the first 30 amino acids from the N-terminal end of the esculentin-2CHa peptide and at least one of an amino acid substitution or modification at position 20 and an amino acid substitution or modification at position 27. Still further optionally, the amino acid substitution or modification at position 20 is substitution with lysine (Lys). Alternatively or additionally, the amino acid substitution or modification at position 27 is substitution with lysine (Lys).

Optionally, the peptide or peptide analogue comprises 37 amino acid residues corresponding to the first 37 amino acids from the N-terminal end of the esculentin-2CHa peptide and at least one of an amino acid substitution or modification at position 20 and an amino acid substitution or modification at position 27. Further optionally, the amino acid substitution or modification at position 20 is substitution with lysine (Lys). Alternatively or additionally, the amino acid substitution or modification at position 27 is substitution with lysine (Lys). Still further optionally, the peptide or peptide analogue consists of 37 amino acid residues corresponding to the first 37 amino acids from the N-terminal end of the esculentin-2CHa peptide and at least one of an amino acid substitution or modification at position 20 and an amino acid substitution or modification at position 27. Still further optionally, the amino acid substitution or modification at position 20 is substitution with lysine (Lys). Alternatively or additionally, the amino acid substitution or modification at position 27 is substitution with lysine (Lys).

Optionally, the peptide or peptide analogue comprises 37 amino acid residues corresponding to the first 37 amino acids from the N-terminal end of the esculentin-2CHa peptide and at least one of an amino acid substitution or modification at position 31 and an amino acid substitution or modification at position 37. Further optionally, the amino acid substitution or modification at position 31 is substitution with serine (Ser). Alternatively or additionally, the amino acid substitution or modification at position 37 is substitution with serine (Ser). Still further optionally, the peptide or peptide analogue consists of 37 amino acid residues corresponding to the first 37 amino acids from the N-terminal end of the esculentin-2CHa peptide and at least one of an amino acid substitution or modification at position 31 and an amino acid substitution or modification at position 37. Still further optionally, the amino acid substitution or modification at position 31 is substitution with serine (Ser). Alternatively or additionally, the amino acid substitution or modification at position 37 is substitution with serine (Ser).

Optionally, the peptide or peptide analogue comprises 37 amino acid residues corresponding to the first 37 amino acids from the N-terminal end of the esculentin-2CHa peptide and at least one of an amino acid substitution or modification at position 20, an amino acid substitution or modification at position 27, an amino acid substitution or modification at position 31, and an amino acid substitution or modification at position 37. Further optionally, the amino acid substitution or modification at position 20 is substitution with lysine (Lys). Alternatively or additionally, the amino acid substitution or modification at position 27 is substitution with lysine (Lys). Further optionally, the amino acid substitution or modification at position 31 is substitution with serine (Ser). Alternatively or additionally, the amino acid substitution or modification at position 37 is substitution with serine (Ser). Still further optionally, the peptide or peptide analogue consists of 37 amino acid residues corresponding to the first 37 amino acids from the N-terminal end of the esculentin-2CHa peptide and at least one of an amino acid substitution or modification at position 20, an amino acid substitution or modification at position 27, an amino acid substitution or modification at position 31, and an amino acid substitution or modification at position 37. Further optionally, the amino acid substitution or modification at position 20 is substitution with lysine (Lys). Alternatively or additionally, the amino acid substitution or modification at position 27 is substitution with lysine (Lys). Further optionally, the amino acid substitution or modification at position 31 is substitution with serine (Ser). Alternatively or additionally, the amino acid substitution or modification at position 37 is substitution with serine (Ser).

According to a second aspect of the present invention, there is provided a pharmaceutical composition comprising the esculentin-2CHa peptide or analogue thereof according to the first aspect of the invention. Optionally, the pharmaceutical composition further comprises a pharmaceutically acceptable carrier. Further optionally, the peptide or peptide analogue is in the form of a pharmaceutically acceptable salt.

According to a third aspect of the present invention, there is provided an esculentin-2CHa peptide or analogue thereof according to the first aspect of the invention, or a pharmaceutical composition according to the second aspect of the invention, for use in the treatment of diabetes, optionally type 2 diabetes, insulin resistance, obesity, and/or hypercholesterolemia.

Optionally, use comprises administration of an esculentin-2CHa peptide or analogue thereof according to the first aspect of the invention, or a pharmaceutical composition according to the second aspect of the invention.

Optionally or additionally, use comprises administration of a pharmaceutically effective amount of esculentin-2CHa peptide or analogue thereof according to the first aspect of the invention, or a pharmaceutical composition according to the second aspect of the invention.

Further optionally, use comprises administration of an esculentin-2CHa peptide or analogue thereof according to the first aspect of the invention, or a pharmaceutical composition according to the second aspect of the invention to a subject.

Still further optionally, use comprises administration of an esculentin-2CHa peptide or analogue thereof according to the first aspect of the invention, or a pharmaceutical composition according to the second aspect of the invention to a human subject.

Optionally, use comprises at least daily administration of an esculentin-2CHa peptide or analogue thereof according to the first aspect of the invention, or a pharmaceutical composition according to the second aspect of the invention.

Optionally, use comprises daily administration of an esculentin-2CHa peptide or analogue thereof according to the first aspect of the invention, or a pharmaceutical composition according to the second aspect of the invention.

Alternatively, use comprises twice daily administration of an esculentin-2CHa peptide or analogue thereof according to the first aspect of the invention, or a pharmaceutical composition according to the second aspect of the invention.

Optionally or additionally, use comprises administration of 75 nmol/kg body weight of an esculentin-2CHa peptide or analogue thereof according to the first aspect of the invention, or a pharmaceutical composition according to the second aspect of the invention.

According to a fourth aspect of the present invention, there is provided use of an esculentin-2CHa peptide or analogue thereof according to the first aspect of the invention, or a pharmaceutical composition according to the second aspect of the invention, for the manufacture of a medicament for the treatment diabetes, optionally type 2 diabetes, insulin resistance, obesity, and/or hypercholesterolemia.

According to a fifth aspect of the present invention, there is provided a method of treating diabetes, optionally type 2 diabetes, insulin resistance, and/or obesity; the method comprising administering a pharmaceutically acceptable amount of an esculentin-2CHa peptide or analogue thereof according to the first aspect of the invention, or a pharmaceutical composition according to the second aspect of the invention, to a subject suffering from diabetes, optionally type 2 diabetes, insulin resistance, obesity, and/or hypercholesterolemia.

Optionally, the method comprises administering a pharmaceutically acceptable amount of an esculentin-2CHa peptide or analogue thereof according to the first aspect of the invention, or a pharmaceutical composition according to the second aspect of the invention, to a human subject suffering from diabetes, optionally type 2 diabetes, insulin resistance, obesity, and/or hypercholesterolemia.

Optionally, the method comprises administering an esculentin-2CHa peptide or analogue thereof according to the first aspect of the invention, or a pharmaceutical composition according to the second aspect of the invention at least daily.

Optionally, the method comprises administering an esculentin-2CHa peptide or analogue thereof according to the first aspect of the invention, or a pharmaceutical composition according to the second aspect of the invention daily.

Alternatively, the method comprises administering an esculentin-2CHa peptide or analogue thereof according to the first aspect of the invention, or a pharmaceutical composition according to the second aspect of the invention twice daily.

Optionally or additionally, the method comprises administering 75 nmol/kg body weight of an esculentin-2CHa peptide or analogue thereof according to the first aspect of the invention, or a pharmaceutical composition according to the second aspect of the invention.

For the purposes of the present specification, it is understood that this invention is not limited to the specific methods, treatment regimens, or particular procedures, which as such may vary. Moreover, the terminology used herein is for the purpose of describing particular embodiments and is not intended to be limiting.

As referred to herein, the esculentin-2CHa peptide of the invention corresponds to amino acids 4-40 of the peptide identified by accession number ACZ44708 (version: ACZ44708.1; GI:269818985).

In the present application, the position of the first amino acid of the esculentin-2CHa peptide according to the invention is termed "position 1", and corresponds to the fourth amino acid of the peptide sequence of accession number ACZ44708. Thus, when referring to a particular amino acid position in the present application, for example the amino acid at position 7, it is intended to mean the consecutive position of the amino acid, for example the seventh amino acid identified starting from the fourth amino acid of the peptide sequence of accession number ACZ44708.

The term "substitution" is used herein to describe the replacement of an amino acid residue in a polypeptide chain with another natural or synthetic amino acid, or with an isomer of the amino acid residue. The term "modification" is used herein to describe the physical or chemical modification of an amino acid residue, or alternatively, the replacement of an amino acid with a modified version of the amino acid.

The term "polypeptide" is used herein synonymously with the term peptide.

By the term "subject", is meant an individual. Optionally, the subject is a mammal. Further optionally, the subject is a human.

By the term "hypercholesterolemia" is meant a disease or disorder having or exhibiting abnormal cholesterol levels and which can include cardiovascular disease, coronary heart disease, atherosclerosis, myocardial infarction (heart attack), stroke, and/or peripheral vascular disease.

BRIEF DESCRIPTION OF THE DRAWINGS

The embodiments of the present invention will now be described, by way of non-limiting example, with reference to the accompanying drawings, in which:

FIG. 2 illustrates the dose-dependent effects of [Lys20, Lys27]-Esculentin-2CHa on insulin (A) and LDH (B) release from BRIN-BD11 cells. Values are mean±SEM with n=8 for insulin and n=6 for LDH. *P<0.001, P<0.01 and *<0.05 compared to glucose (5.6 mM) alone;

FIG. 16 illustrates the effects of [Lys20, Lys27]-esculentin-2CHa on membrane potential in BRIN-BD11 cells expressed as (A) RFU and (B) area under the curve. Values are Mean±SEM (n=6). *P<0.001, P<0.01 compared to 5.6 mM glucose alone;

FIG. 17 illustrates the effects of esculentin-2CHa-(GA30) on membrane potential in BRIN-BD11 cells expressed as (A) RFU and (B) area under the curve. Values are Mean±SEM (n=6). *P<0.001, P<0.01 compared to 5.6 mM glucose alone;

FIG. 24 illustrates the effects of [Ser31, Ser37]-esculentin-2CHa on intracellular calcium in BRIN-BD11 cells expressed as (A) RFU and (B) area under the curve. Values are Mean±SEM (n=8). ***P<0.001 compared to 5.6 mM glucose alone;

FIG. 26 illustrates the effects of [Lys20, Lys27]-esculentin-2CHa-(GA30) on intracellular calcium in BRIN-BD11 cells expressed as (A) RFU and (B) area under the curve. Values are Mean±SEM (n=6). *P<0.05, ***P<0.001 compared to 5.6 mM glucose alone;

FIG. 39 illustrates the amino acid sequences of the esculentin-2CHa peptide, and analogues thereof, of the invention. "r" represents D-Arginine; "k" represents D-Lysine; "Orn" represents L-Ornithine; "NH$_2$" represents an amide group; "K(Oct)" represents a Lysine residue modified by the addition of octanoate;

Figure 41:
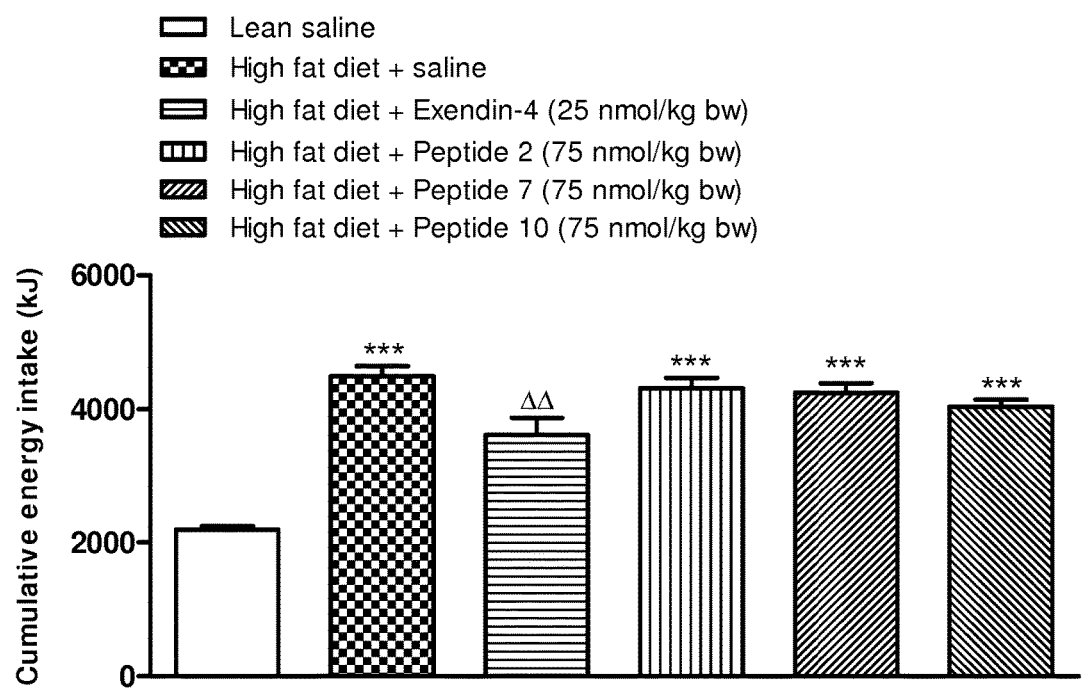
Figure 42:
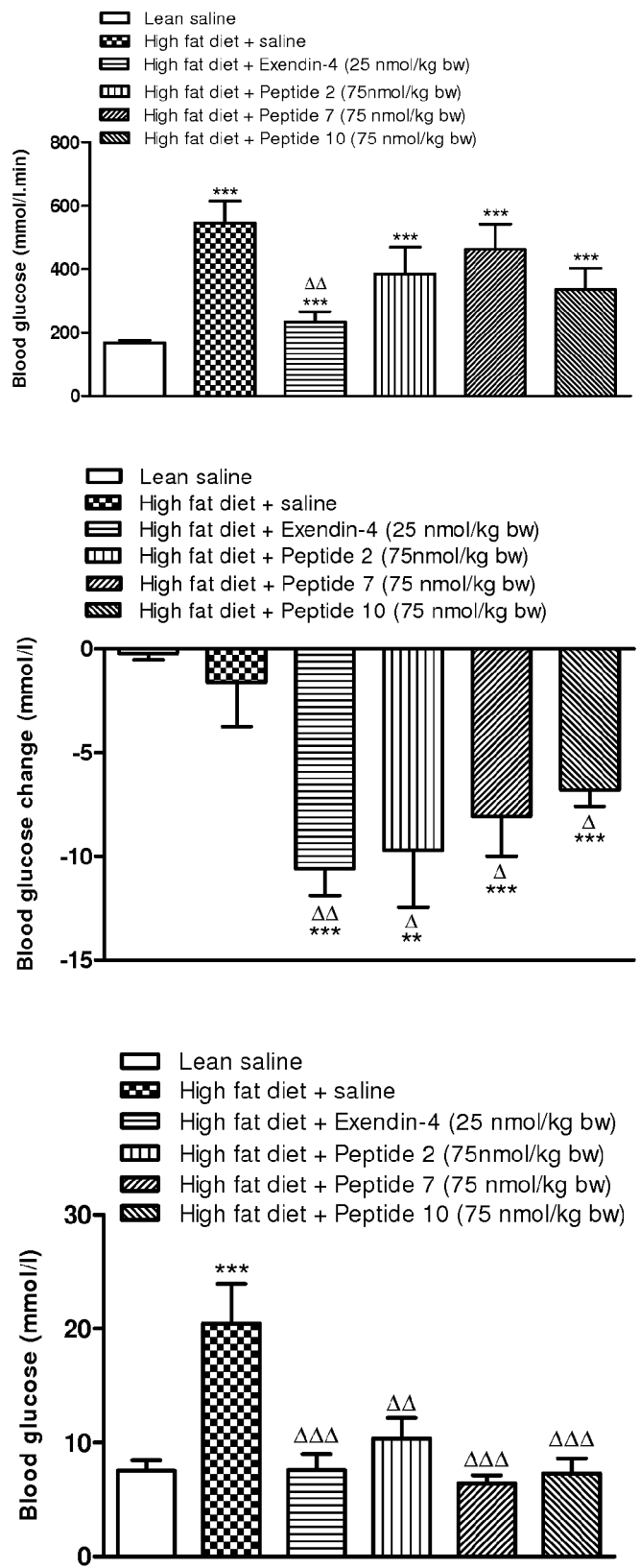
Figure 44:
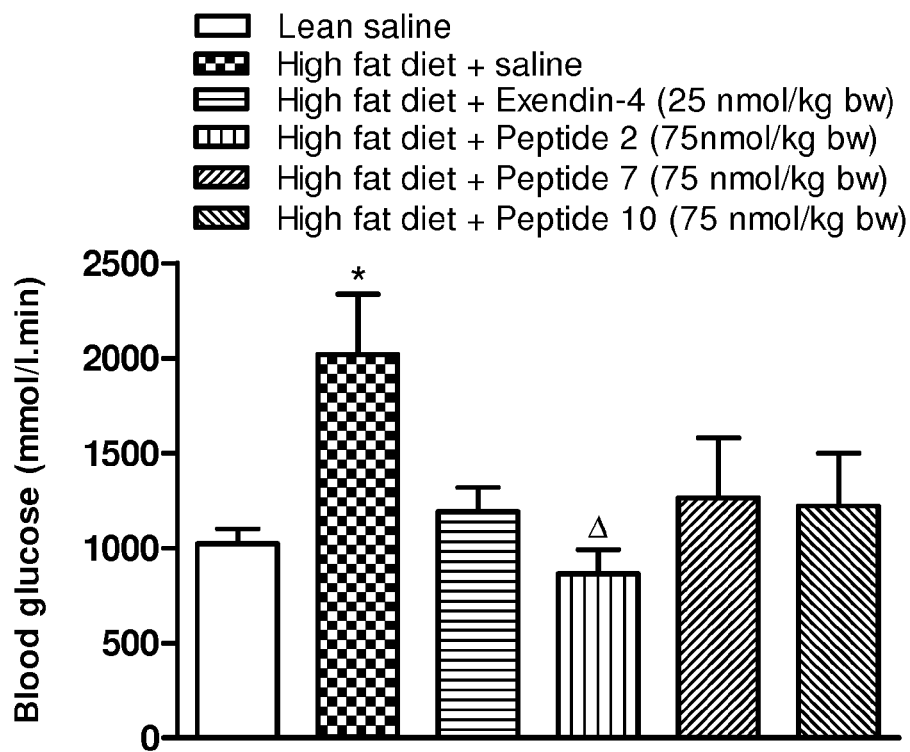
Figure 45:
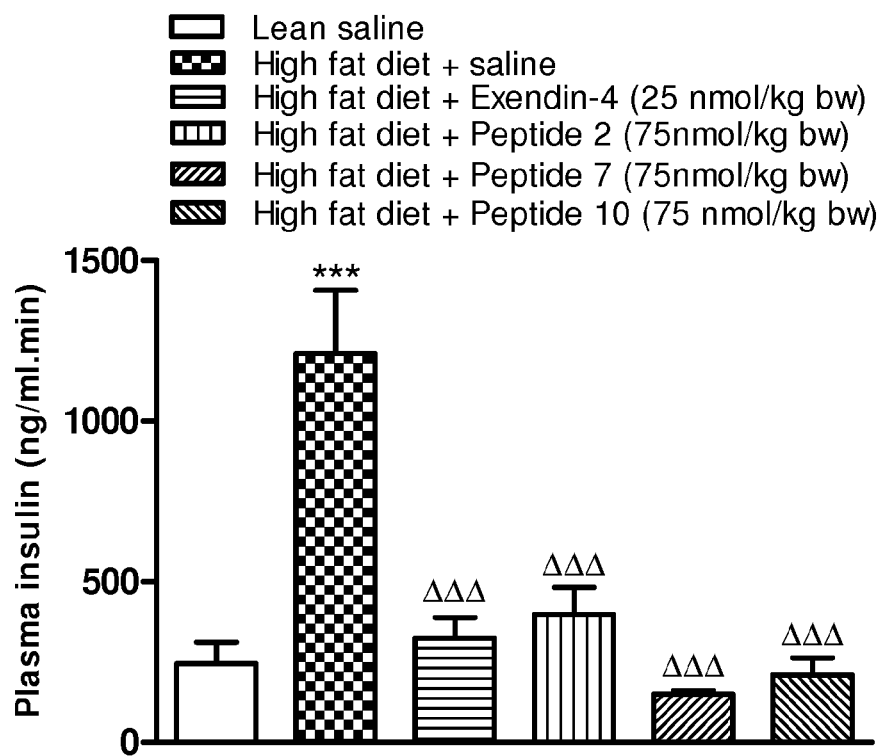
Figure 46:
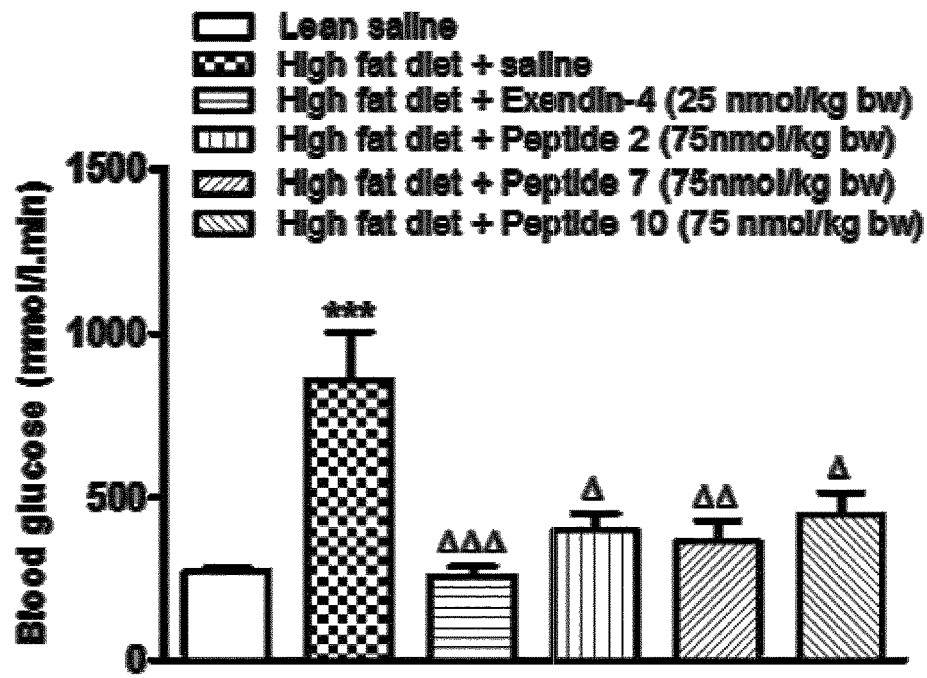
Figure 47:
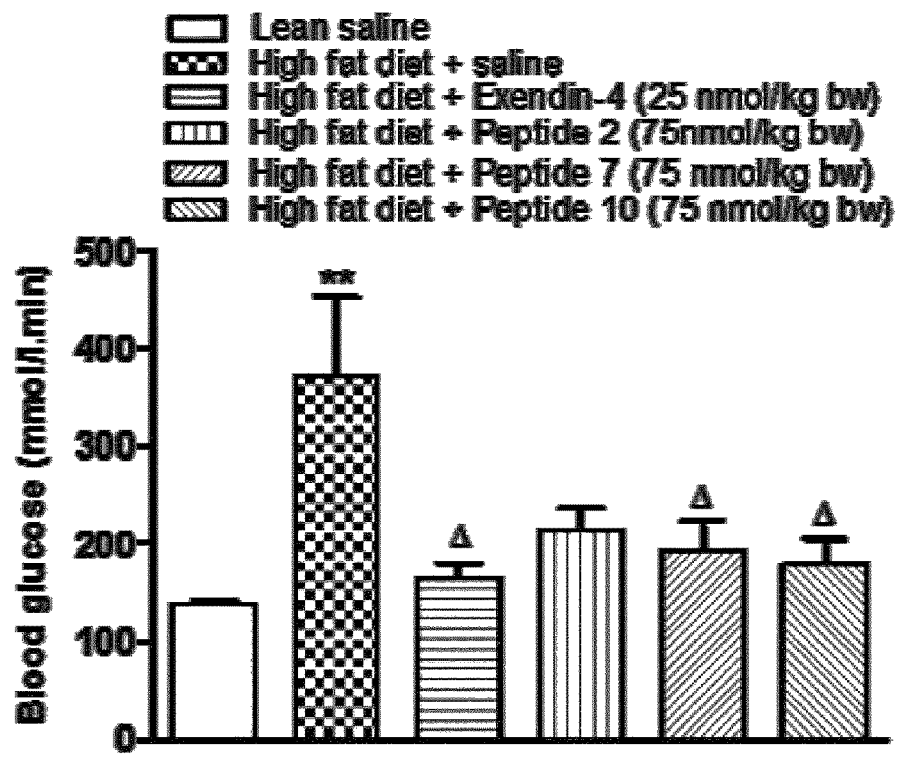
Figure 48:
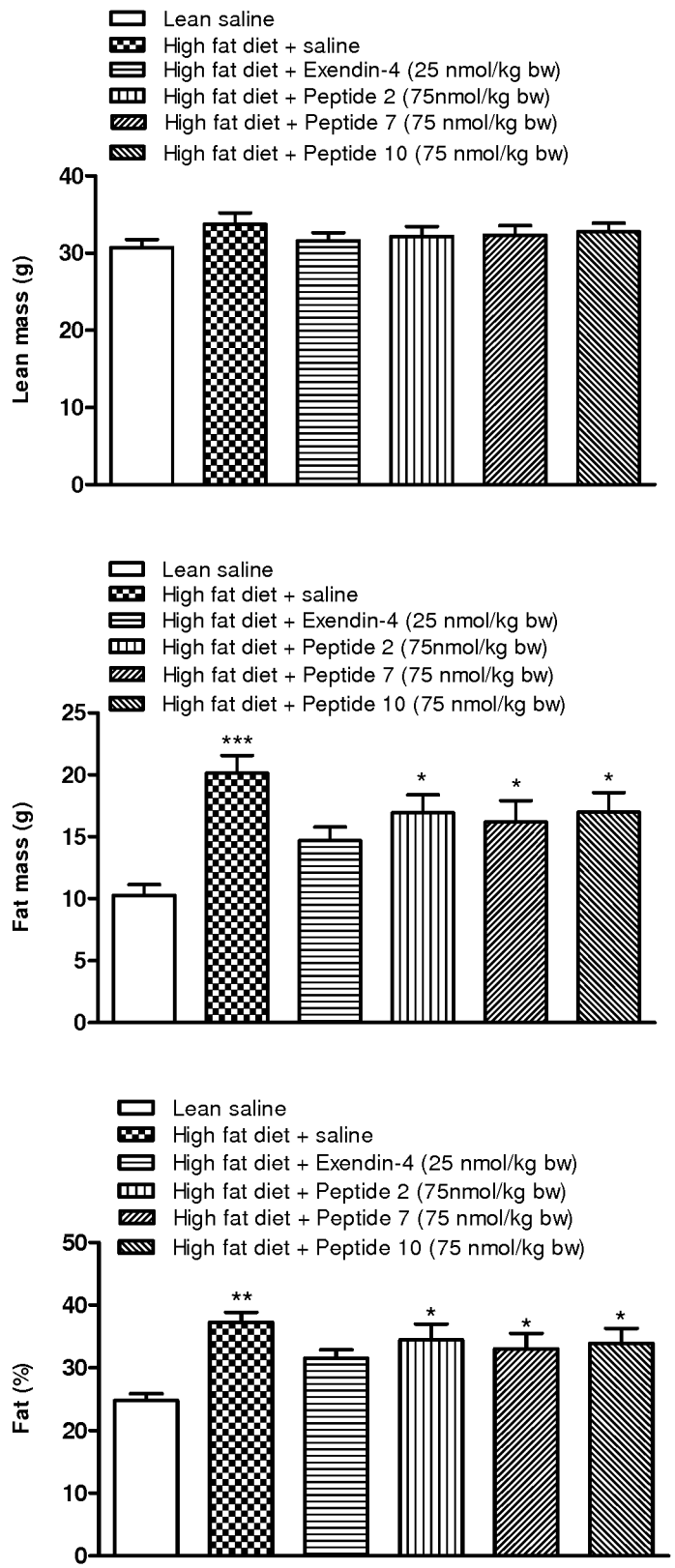
Figure 50B:
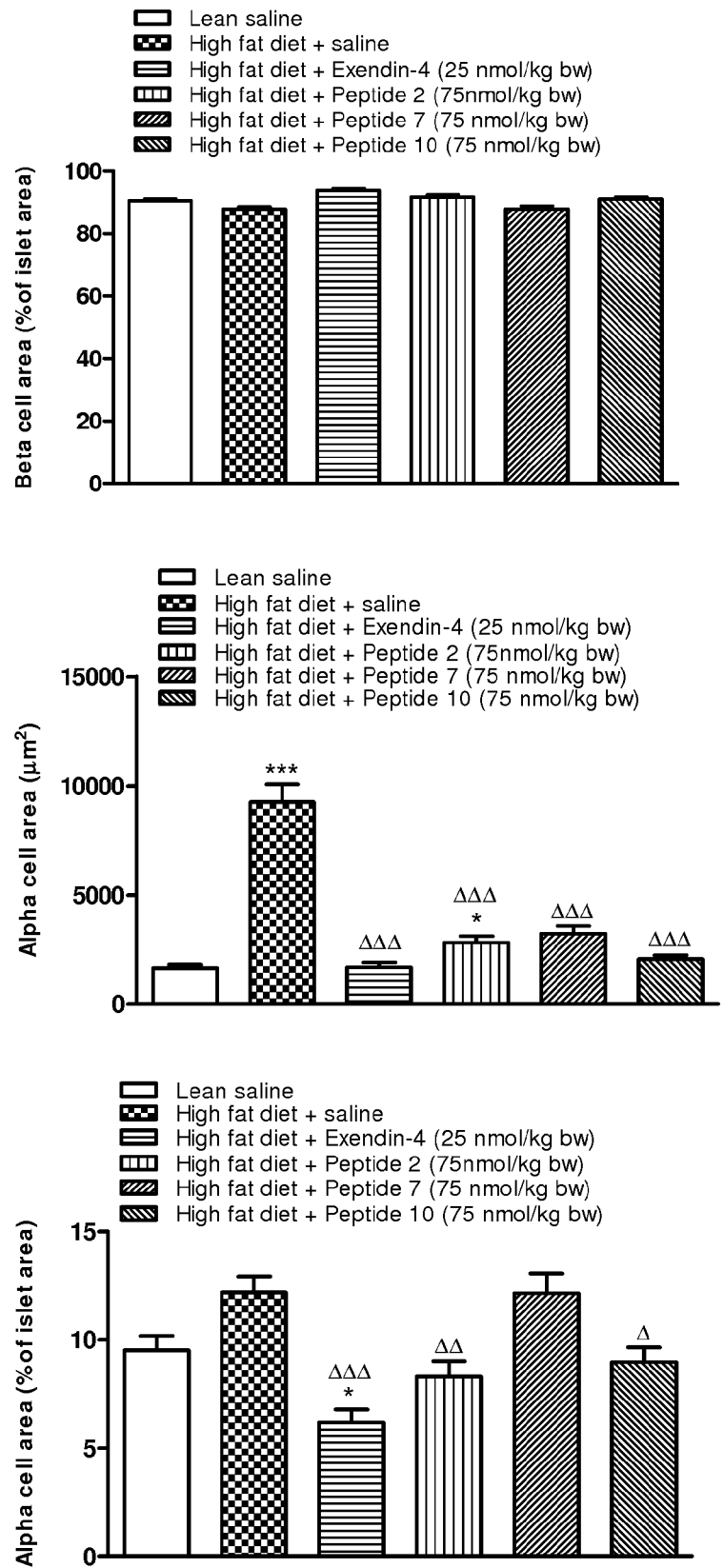
Figure 51:
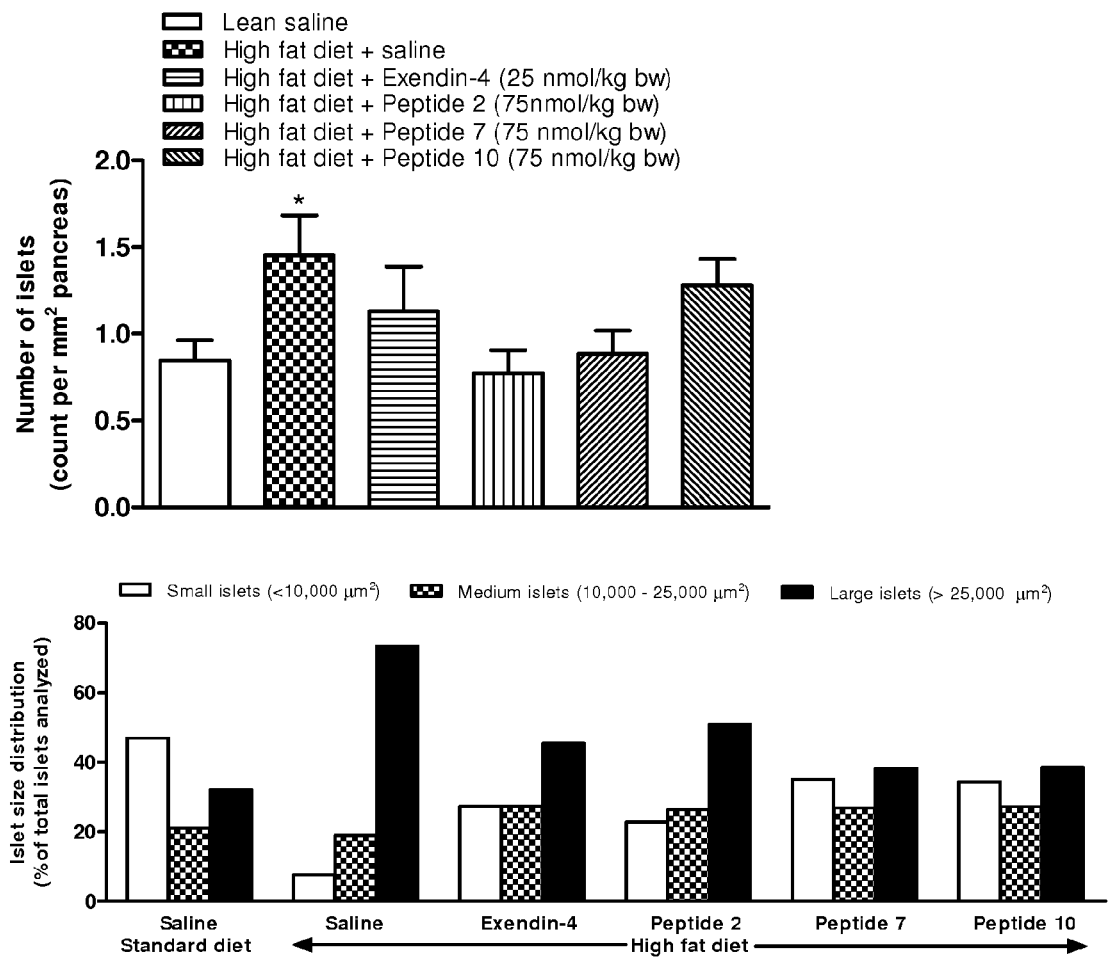
Figure 52A:
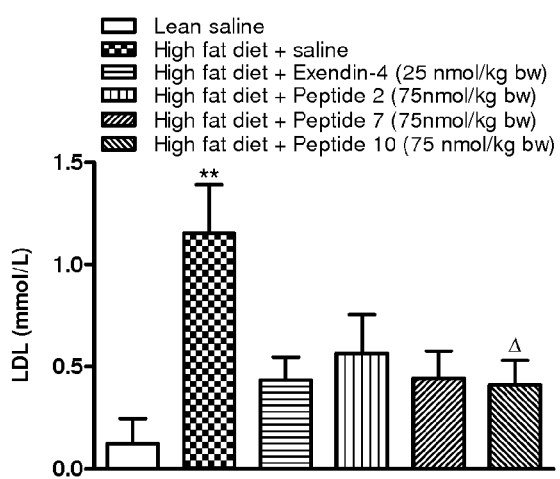

FIG. 41 illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on energy intake of Swiss TO mice on high fat diet. Values are mean±SEM (n=6 to 8). **p<0.01 compared to lean saline Δp<0.05, ΔΔΔp<0.001 compared to high fat diet saline control;

FIG. 42 illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on blood glucose of Swiss TO mice on high fat diet. D—Blood glucose (mmol/l.min), E—Blood glucose change, F—Terminal blood glucose. Values are mean±SEM (n=6 to 8). p<0.01, *p<0.001 compared to lean saline Δp<0.05, ΔΔp<0.01, ΔΔΔp<0.001 compared to high fat diet saline control;

FIG. 43 illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on plasma insulin of Swiss TO mice on high fat diet. D—Plasma insulin (ng/ml.min), E—Terminal plasma insulin. Values are mean±SEM (n=6 to 8). *p<0.05, p<0.01, *p<0.001 compared to lean saline Δp<0.05, ΔΔp<0.01, ΔΔΔp<0.001 compared to high fat diet saline control;

FIG. 44 illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on glucose tolerance of Swiss TO mice on high fat diet; Values are mean±SEM (n=6 to 8). *p<0.05 compared to lean saline Δp<0.05 compared to high fat diet saline control;

FIG. 45 illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on plasma insulin of Swiss TO mice on high fat diet; Values are mean±SEM (n=6 to 8). *p<0.05, p<0.01, *p<0.001 compared to lean saline Δp<0.05, ΔΔp<0.01, ΔΔΔp<0.001 compared to high fat diet saline control;

FIG. 46 illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on insulin sensitivity of Swiss TO mice on high fat diet. Values are mean±SEM (n=6 to 8). *p<0.05, p<0.01, *p<0.001 compared to lean saline Δp<0.05, ΔΔp<0.01, ΔΔΔp<0.001 compared to high fat diet saline control;

FIG. 47 illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on 24 h blood glucose profile of Swiss TO mice on high fat diet. Values are mean±SEM (n=6 to 8). *p<0.05, p<0.01, *p<0.001 compared to lean saline. Δp<0.05 compared to high fat diet saline control;

FIG. 48 illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on lean, 10 fat mass and fat (%) of Swiss TO mice on high fat diet. Values are mean±SEM (n=6 to 8). *p<0.05, p<0.01, *p<0.001 compared to lean saline;

FIG. 49 illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on insulin release from islets isolated from Swiss TO mice on high fat diet. Values are mean±SEM (n =4). *p<0.05 compared to glucose (20 mM). Δp<0.05, ΔΔp<0.01 compared to glucose (3 mM);

FIGS. 50A & 50B illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on pancreatic islet morphometry (Islet, beta and alpha cell areas) of Swiss TO mice on high fat diet. Values are mean±SEM (n =6 to 8 mice, ~150 islets were analysed). *p<0.05, p<0.01, *p<0.001 compared to lean saline Δp<0.05, ΔΔp<0.01, ΔΔΔp<0.001 compared to high fat diet saline control;

FIG. 51 illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on pancreatic islet morphometry (Number of islets and islet size distribution) of Swiss TO mice on high fat diet. Values are mean±SEM (n =6 to 8 mice, ~150 islets were analysed). *p<0.05 compared to lean saline; and FIGS. 52A & 52B illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on lipid profile of Swiss TO mice on high fat diet. Values are mean±SEM (n=5). *p<0.05 compared to lean saline. Δp<0.05 compared to high fat diet saline control.

The Sequence Listing is submitted as an ASCII text file [9206-97447-01_Sequence_Listing.txt, Jul. 29, 2016, 5.57 KB], which is incorporated by reference herein.

Materials and Methods

Determination of Insulin-Releasing and Cytotoxic Activities

BRIN-BD11 cells (Public Health England; Cat. No: 10033003) were grown at 37° C. in an atmosphere of 5% $CO_2$ and 95% air in RPMI-1640 tissue culture medium containing 10% (v/v) fetal calf serum, antibiotics (100 U/ml penicillin, 0.1 mg/ml streptomycin) and 11.1 mM glucose as previously described (Marenah et al, 2004; Conlon et al, 2008; and Mechkarska et al, 2011). The cells were pre-incubated for 40 min at 37° C. in 1.0 ml Krebs Ringer bicarbonate (KRB) buffer, pH 7.4 supplemented with either 5.6 mM or 16.7 mM glucose and 0.1% (w/v) bovine serum albumin (Conlon et al, 2008). Incubations with synthetic peptides ($10^{-12}$-$3\times10^{-6}$ M; n =8) were performed for 20 min at 37° C. using the same buffer. After incubation, aliquots of cell supernatant were removed for insulin radioimmunoassay as described by Flatt and Bailey (1981).

In order to determine cytotoxicity, BRIN-BD11 cells were seeded into 24-multiwell plates and allowed to attach during overnight culture at 37° C. Prior to the test, cells were pre-incubated for 40 min at 37° C. in KRB buffer supplemented with 5.6 mM glucose (1.0 ml). Test incubations with synthetic peptides (0.1-3 μM; n =4) were performed for 20 min at 37° C. Lactate dehydrogenase (LDH) concentrations in the cell supernatants were measured using a CytoTox96 nonradioactive cytotoxicity assay kit (Promega, Madison, Wis., USA) according to the manufacturer's protocol.

Investigation of Cellular Mechanism of Actions

Cellular mechanism of actions of synthetic peptides was investigated by measuring insulin-release from BRIN-DB11 cells in the presence or absence of synthetic peptides ($10^{-6}$M) and known modulators of insulin-release. These additional incubations were carried in (a) medium supplemented with 16.7 mM glucose, (b) calcium-free medium supplemented with 5.6 mM glucose, (c) medium containing 5.6 mM glucose and diazoxide (300 mM), (d) medium containing 5.6 mM glucose and verapamil (50 mM), and (e)

medium supplemented with 16.7 mM glucose and 30 mM KCl. Cells were incubated for 20 min at 37° C. and insulin concentrations in cell supernatants were measured by radioimmunoassay (Flatt and Bailey (1981)).

Intracellular Calcium ($[Ca^{2+}]_i$) and Membrane Potential Studies

Changes in membrane potential and $[Ca^{2+}]_i$ were determined fluorimetrically using monolayers of BRIN-BD11 cells as previously described by Miguel et al (2004) and Abdel-Wahab et al (2007) using a membrane potential assay kit or a $Ca^{2+}$ assay kit (Molecular Devices, Sunnyvale, Calif., USA) according to the manufacturer's recommended protocols. Data were acquired using a FlexStation scanning fluorimeter with integrated fluid transfer workstation (Molecular Devices). The cells were incubated at 37° C. for 10 min with synthetic peptides at a concentration of 1 µM. Control incubations in the presence of 5.6 mM glucose only, 30 mM KCl, and 10 mM alanine were also carried out.

In Vivo Studies

All animal experiments were carried out in accordance with the UK Animals (Scientific Procedures) Act 1986 and EC Directive 86/609/EEC for animal experiments. For acute in vivo glucose tolerance studies, age-matched groups (n=6) of overnight fasted male NIH Swiss TO mice received an intraperitoneal injection of either glucose alone (32% w/v) or in combination with synthetic peptides (75 nmol/kg body weight). All solutions were administered in 0.9% NaCl (5 ml/kg body weight). Blood samples were collected as previously described (Abdel-Wahab et al, 2010) at the times indicated in FIGS. 27-38. Blood glucose concentrations were measured by Bayer Ascencia Blood glucose meter and plasma insulin concentrations were measured by radioimmunoassay as described by Flatt and Bailey (1981). For chronic in vivo studies, male NIH Swiss TO mice were fed high fat diet or standard diet from 8 weeks of age to 27 weeks of age. Peptides were administered twice daily for 28 days. No adverse effects were observed following administration of the peptide. Parameters including body weight, energy intake, blood glucose and plasma insulin levels were monitored once in three days for 28 days. Body weight and energy intake were measured by weighing mice and food weights respectively. At the end of the study, to determine glucose tolerance, glucose (18 mmol/kg bw) was injected (i.p) to overnight fasted mice and blood glucose levels were monitored at 0, 15, 30, 60 and 90 minutes. To determine insulin sensitivity, insulin (25 U/kg bw) was injected and blood glucose levels were monitored at 0, 15, 30 and 60 minutes. To determine blood glucose profile over a period of 24 h, blood glucose levels were monitored at 0 (before peptide administration), 2, 4, 8 (before peptide administration) and 24 h (before peptide administration). Lean and fat mass were determined by DXA scanning and terminal blood and tissues were collected for ex vivo studies including pancreatic islet morphology, hormone content, lipid profile and islet function.

HPLC

Peptides were suspended in a solution containing (0.1%) (v/v) TFA/water before injection into a Aeris PEPTIDE 3.6 u XB-C18 reversed-phase HPLC column (phenomenex, UK). The column was equilibrated with 0.1% (v/v) TFA/water at a flow rate of 1.0 ml/min. The concentration of acetonitrile in the eluting solvent was raised using linear gradients from 0 to 28% acetonitrile over 10 min, to 56% over 20 min and from 56% to 70% over 5 min. Absorbance was monitored at 214 nm and 280 nm. Peaks were collected for analysis by mass spectrometry.

Mass Spectrometry

For mass spectrometry analysis, peaks collected from reversed phase HPLC were mixed with matrix solution (10 mg/ml α-cyano-4-hydroxycinnamic acid) in acetonitrile/ethanol (1:1) and placed on sample plate. After drying at room temperature, the samples were analysed using a Voyager DE-PRO instrument (Applied Biosystems, Forster City, USA) operated in reflection mode with delayed extraction at an accelerating voltage of 20 kV in the ion source. The mass-to-charge ratio (m/z) versus peak intensity was recorded.

EXAMPLES

Example 1—In Vitro Effects on Insulin Release and Mechanism of Action

Figure 1:
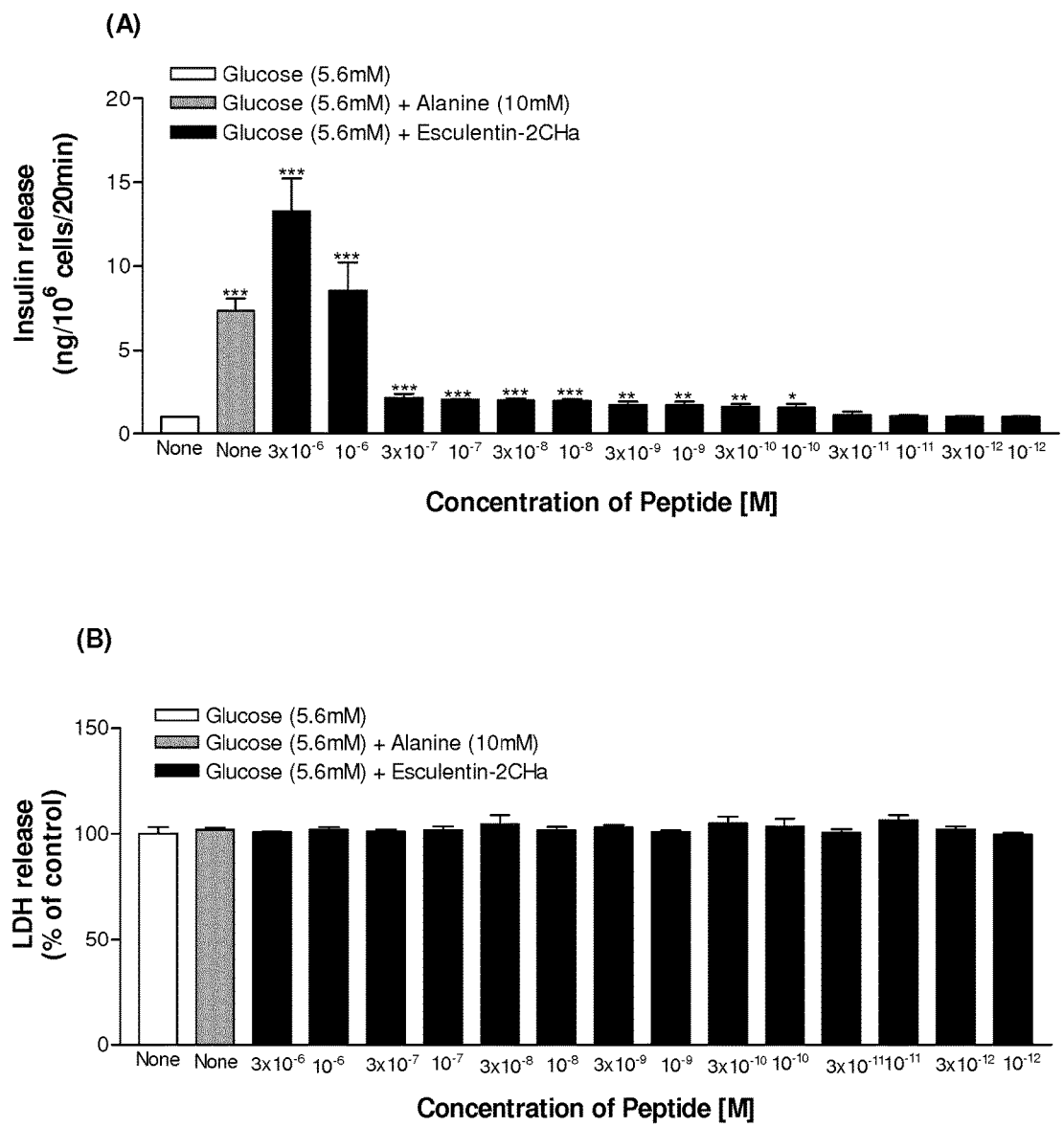
FIG. 1 illustrates the dose-dependent effects of Esculentin-2CHa on insulin (A) and LDH (B) release from BRIN- BD11 cells. Values are mean±SEM with n=8 for insulin and n=6 for LDH. *P<0.001, P<0.01 and *<0.05 compared to glucose (5.6 mM) alone.
Figure 3:
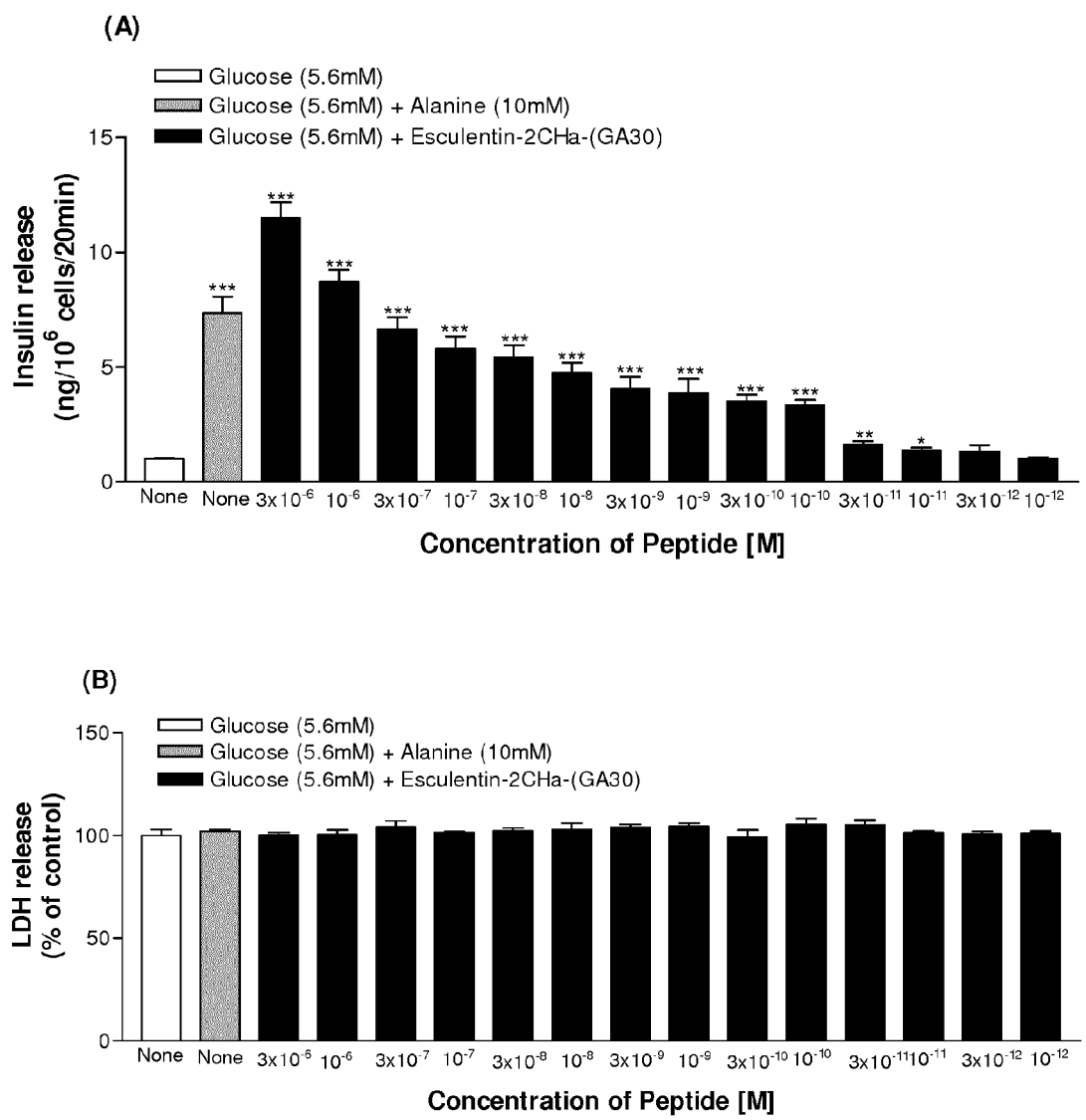
FIG. 3 illustrates the dose-dependent effects of Esculentin-2CHa-(GA30) on insulin (A) and LDH (B) release from BRIN-BD11 cells. Values are mean±SEM with n=8 for insulin and n=6 for LDH. *P<0.001, P<0.01 and *<0.05 compared to glucose (5.6 mM) alone.
Figure 4:
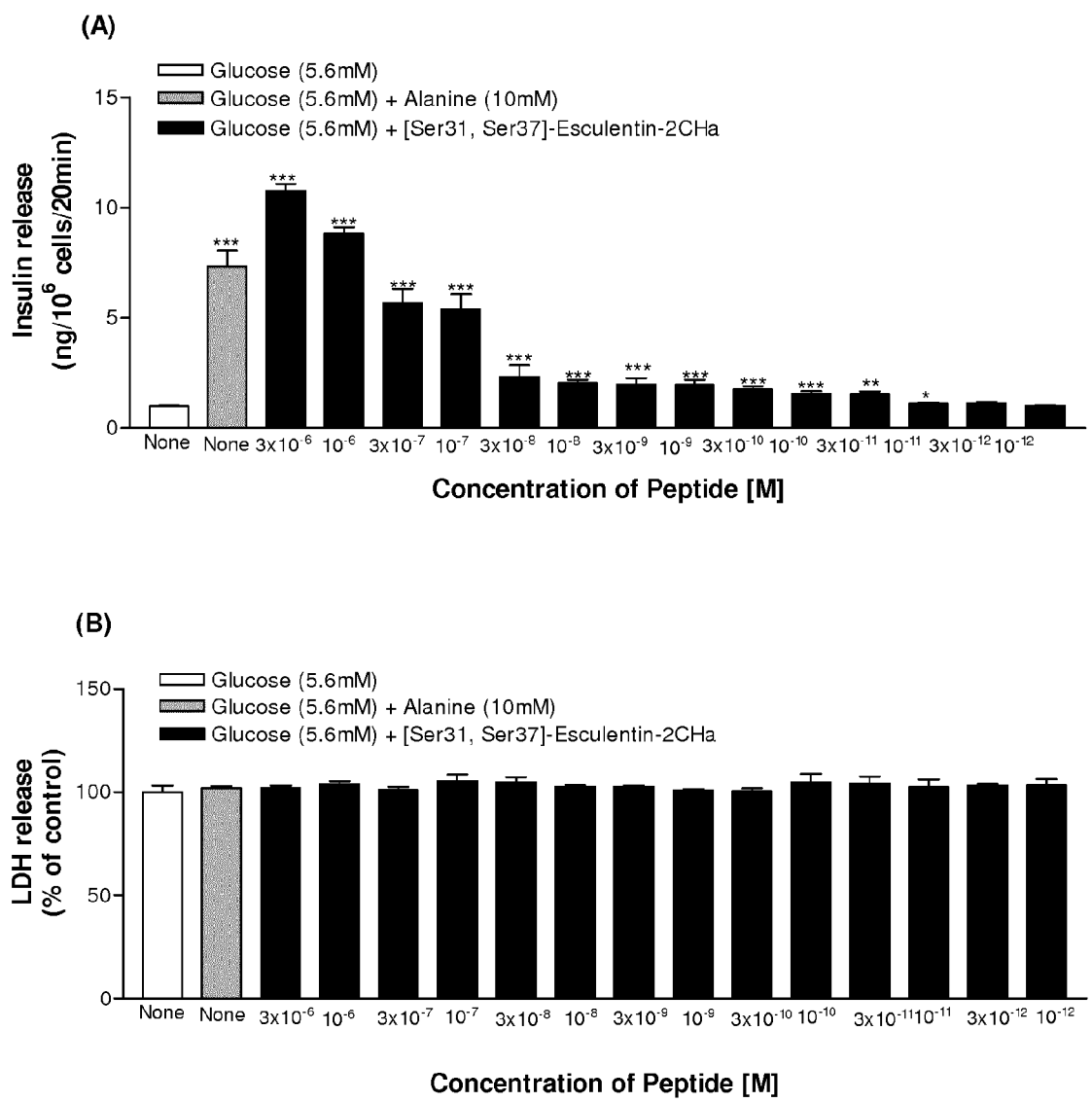
FIG. 4 illustrates the dose-dependent effects of [Ser31, Ser37]-Esculentin-2CHa on insulin (A) and LDH (B) release from BRIN-BD11 cells. Values are mean±SEM with n=8 for insulin and n=6 for LDH. *P<0.001, P<0.01 and *P<0.05 compared to glucose (5.6 mM) alone.
Figure 5:
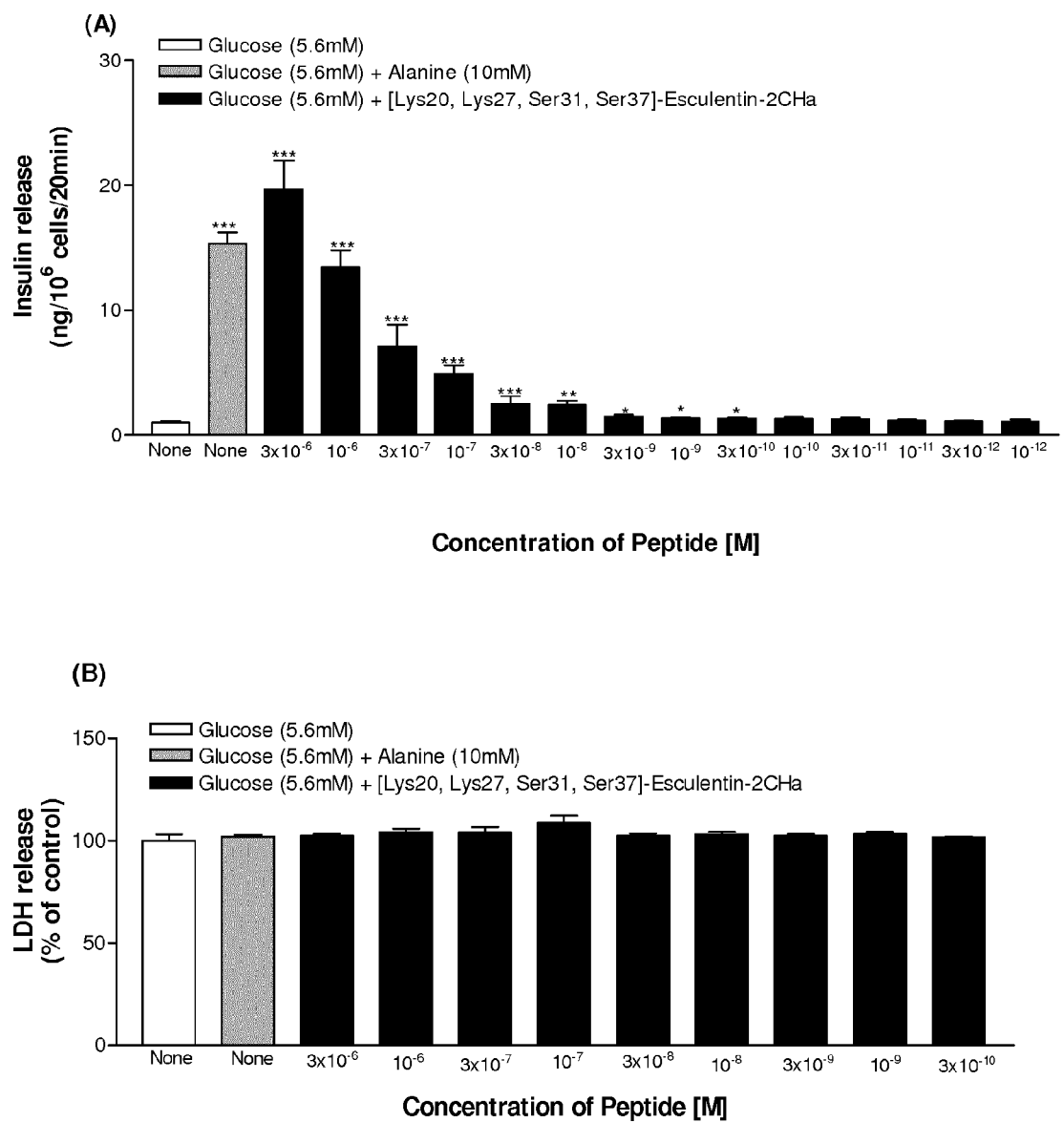
FIG. 5 illustrates the dose-dependent effects of [Lys20, Lys27, Ser31, Ser37]-Esculentin-2CHa on insulin (A) and LDH (B) release from BRIN-BD11 cells. Values are mean±SEM with n=8 for insulin and n=6 for LDH. *P<0.001, P<0.01 and *P<0.05 compared to glucose (5.6 mM) alone.
Figure 6:
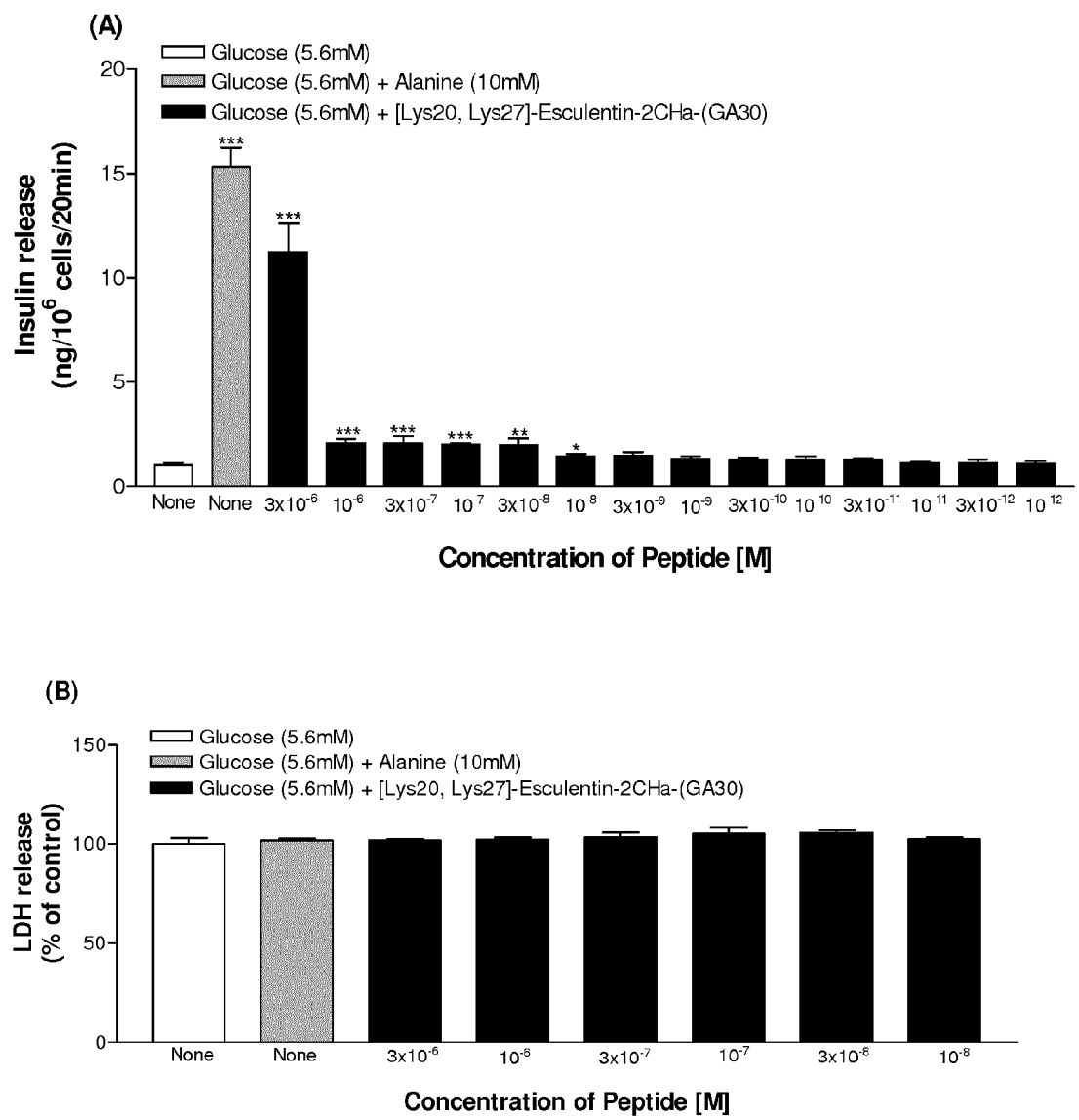
FIG. 6 illustrates the dose-dependent effects of [Lys20, Lys27]-Esculentin-2CHa-(GA30) on insulin (A) and LDH (B) release from BRIN-BD11 cells. Values are mean±SEM with n=8 for insulin and n=6 for LDH. *P<0.001, P<0.01 and *P<0.05 compared to glucose (5.6 mM) alone.
Figure 7:
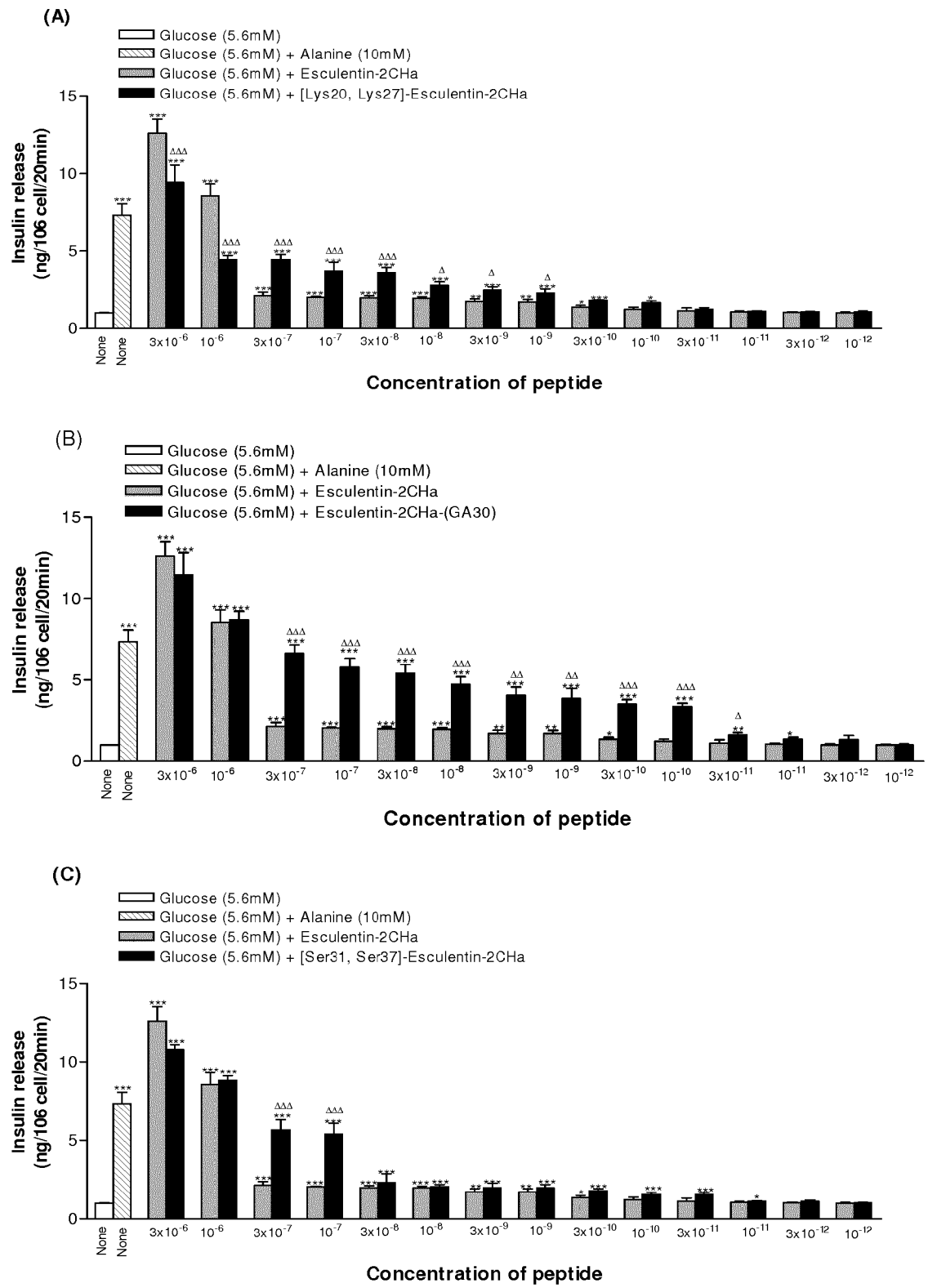
FIG. 7 illustrates the comparative effects of native esculentin-2CHa and its esculentin-2CHa-(GA30), [Lys20, Lys27]- and [Ser31, Ser37]-analogues on insulin release from BRIN-BD11 cells. Values are mean±SEM with n=8 for insulin. *P<0.001, P<0.01 and *P<0.05 compared to glucose (5.6 mM) alone. ΔΔΔP<0.001, ΔΔP<0.01 and ΔP<0.05 compared to respective incubation with esculentin-2Cha.
Figure 8:
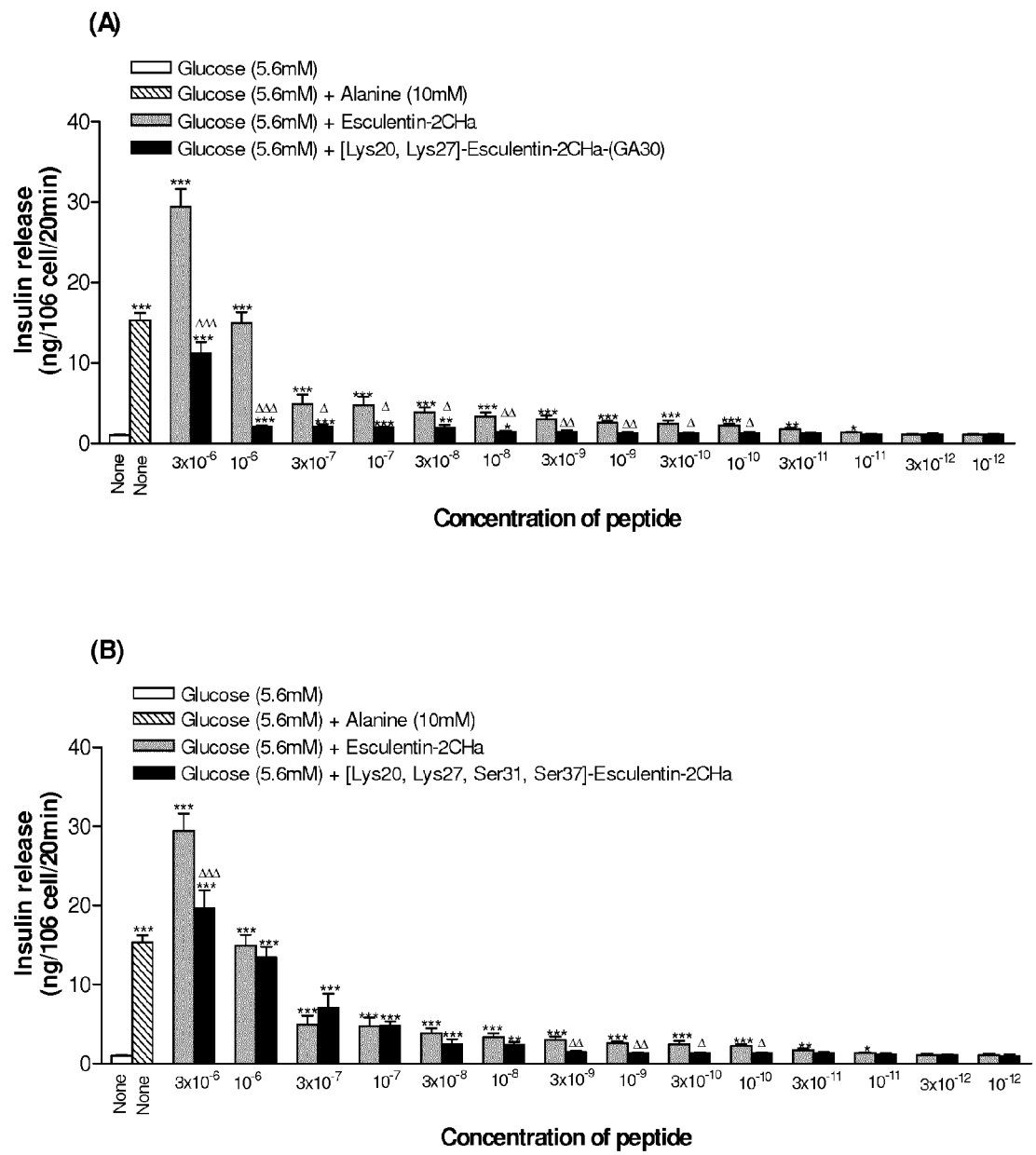
FIG. 8 illustrates the comparative effects of native esculentin-2Cha and its [Lys20, Lys27]-esculentin-(GA30) and [Lys20, Lys27, Ser31, Ser37]-analogues on insulin release from BRIN-BD11 cells. Values are mean±SEM with n=8 for insulin. *P<0.001, P<0.01 and *P<0.05 compared to glucose (5.6 mM) alone. ΔΔΔP<0.001, ΔΔP<0.01 and ΔP<0.05 compared to respective incubation with esculentin-2Cha.
Figure 9:
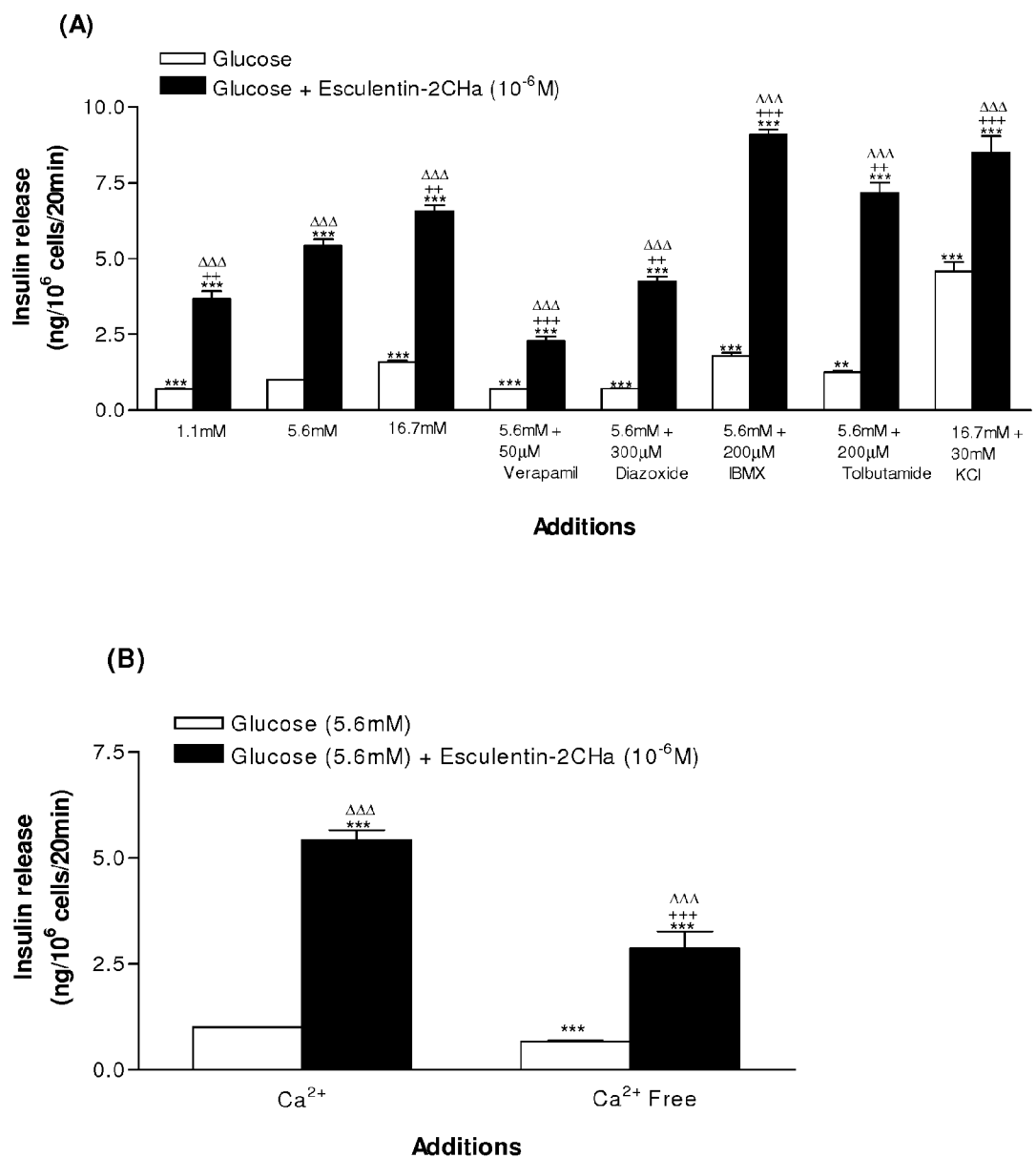
FIG. 9 illustrates the effects of esculentin-2CHa on insulin release from BRIN-BD11 cells in the presence or absence of known modulators of insulin secretion (A) and extracellular calcium (B). Values are Mean±SEM (n=6). *P<0.05, P<0.01, *P<0.001 compared to 5.6 mM glucose alone (A) in the presence of extracellular calcium (B). +P<0.05, ++P<0.01, +++P<0.001 compared to 5.6 mM glucose in the presence of the peptide (A) and in the presence of extracellular calcium (B). ΔP<0.05, ΔΔP<0.01, ΔΔΔP<0.001 compared to respective incubation in the absence of the peptide.
Figure 10:
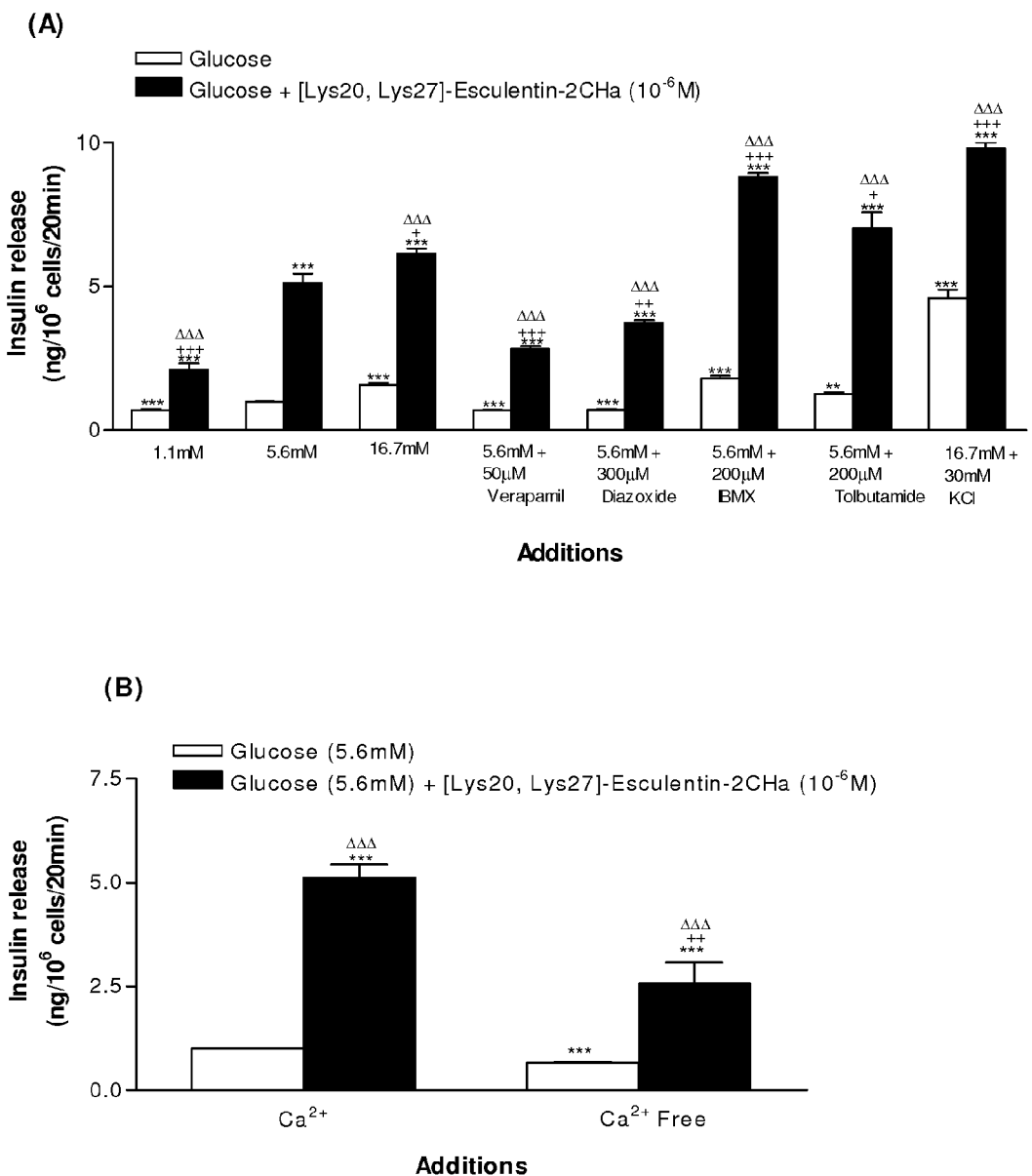
FIG. 10 illustrates the effects of [Lys20, Lys27]-esculentin-2CHa on insulin release from BRIN-BD11 cells in the presence or absence of known modulators of insulin secretion (A) and extracellular calcium (B). Values are Mean±SEM (n=6). *P<0.05, P<0.01, *P<0.001 compared to 5.6 mM glucose alone (A) in the presence of extracellular calcium (B). +P<0.05, ++P<0.01, +++P<0.001 compared to 5.6 mM glucose in the presence of the peptide (A) and in the presence of extracellular calcium (B). ΔP<0.05, ΔΔP<0.01, ΔΔΔP<0.001 compared to respective incubation in the absence of the peptide.
Figure 11:
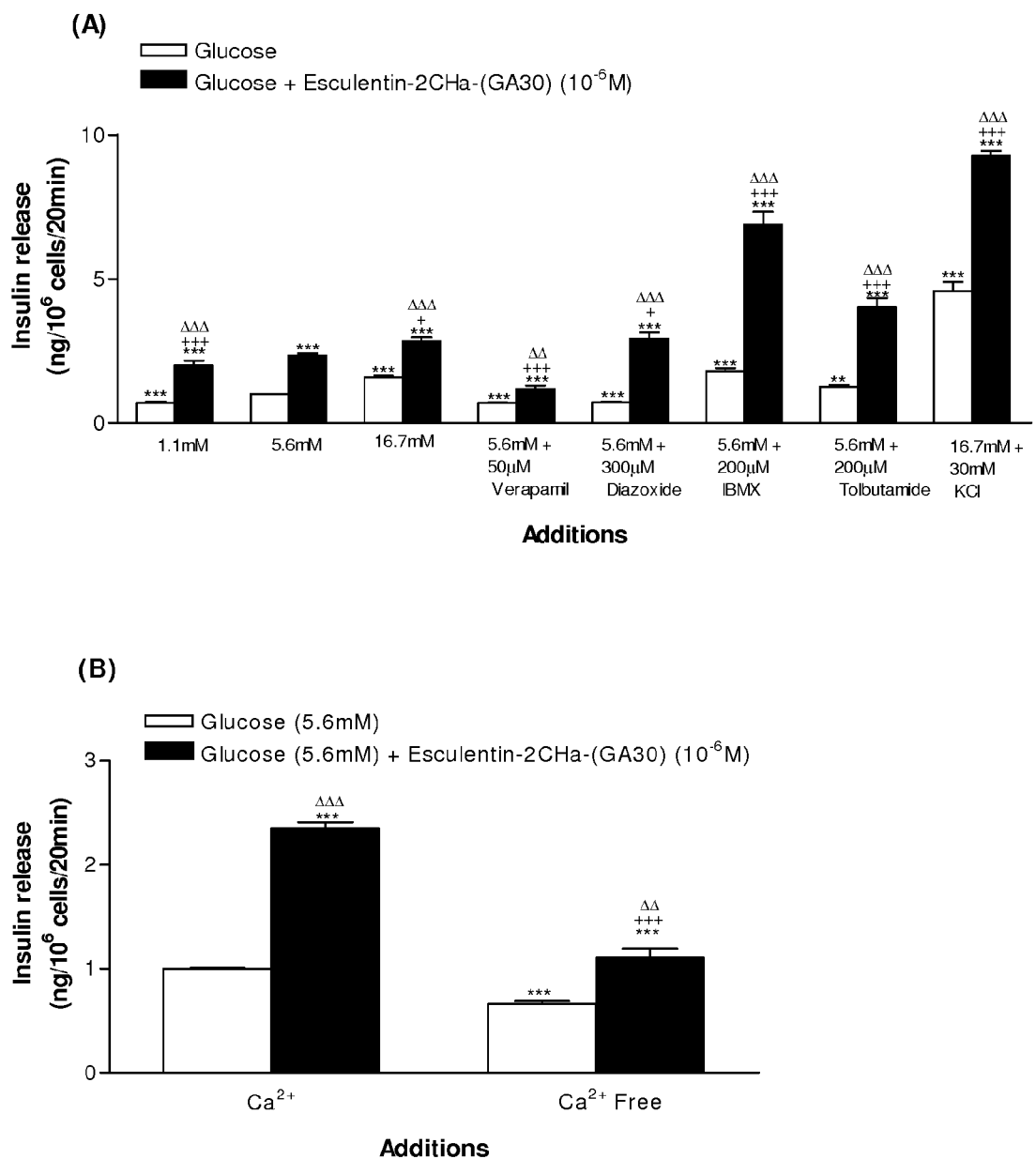
FIG. 11 illustrates the effects of esculentin-2CHa-(GA30) on insulin release from BRIN-BD11 cells in the presence or absence of known modulators of insulin secretion (A) and extracellular calcium (B). Values are Mean±SEM (n=6). *P<0.05, P<0.01, *P<0.001 compared to 5.6 mM glucose alone (A) in the presence of extracellular calcium (B). +P<0.05, ++P<0.01, +++P<0.001 compared to 5.6 mM glucose in the presence of the peptide (A) and in the presence of extracellular calcium (B); ΔP<0.05, ΔΔP<0.01, ΔΔΔP<0.001 compared to respective incubation in the absence of the peptide.
Figure 12:
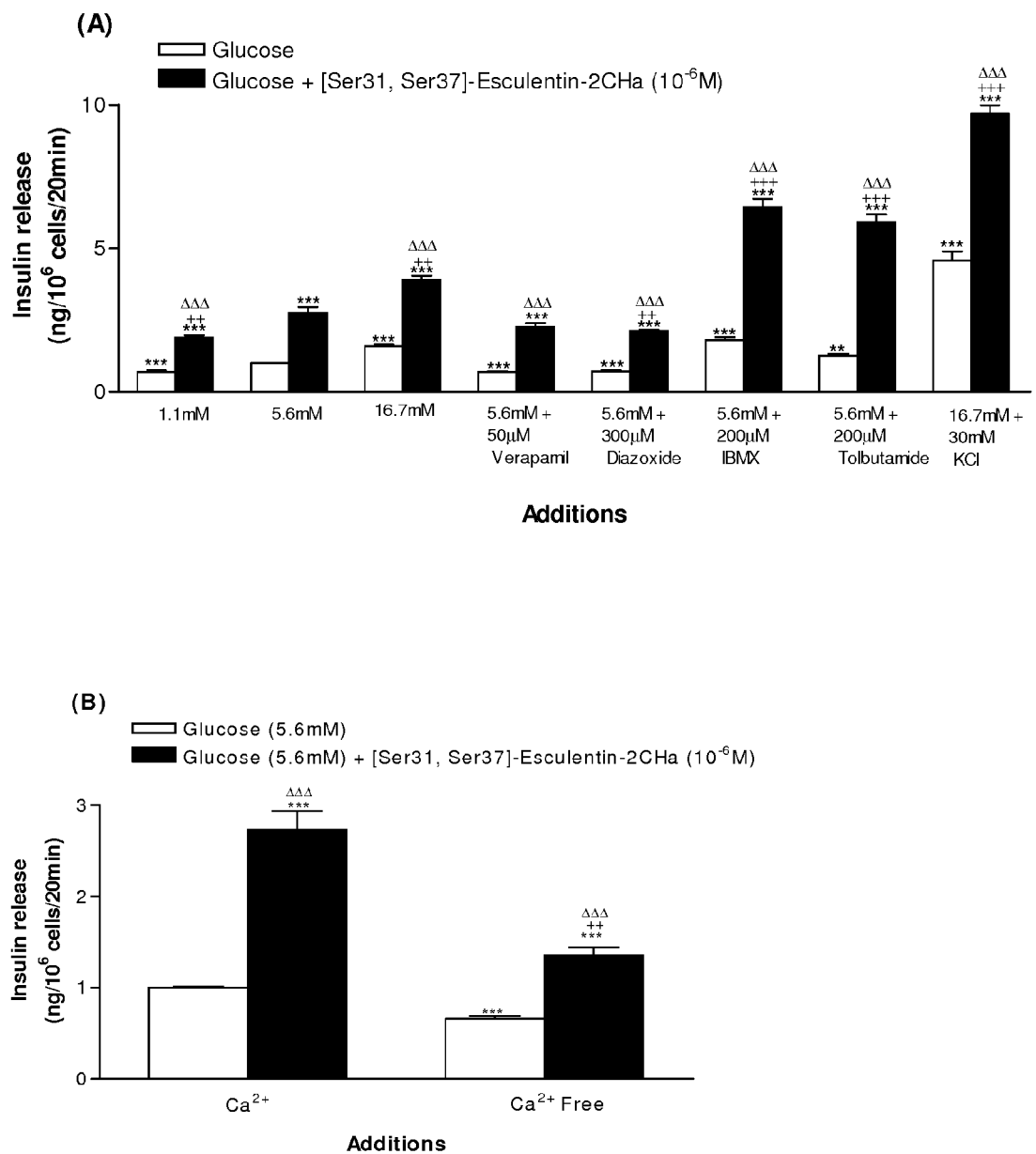
FIG. 12 illustrates the effects of [Ser31, Ser37]-esculentin-2CHa on insulin release from BRIN-BD11 cells in the presence or absence of known modulators of insulin secretion (A) and extracellular calcium (B). Values are Mean±SEM (n=6). *P<0.05, P<0.01, *P<0.001 compared to 5.6 mM glucose alone (A) in the presence of extracellular calcium (B). +P<0.05, ++P<0.01, +++P<0.001 compared to 5.6 mM glucose in the presence of the peptide (A) and in the presence of extracellular calcium (B). ΔP<0.05, ΔΔP<0.01, ΔΔΔP<0.001 compared to respective incubation in the absence of the peptide.
Figure 13:
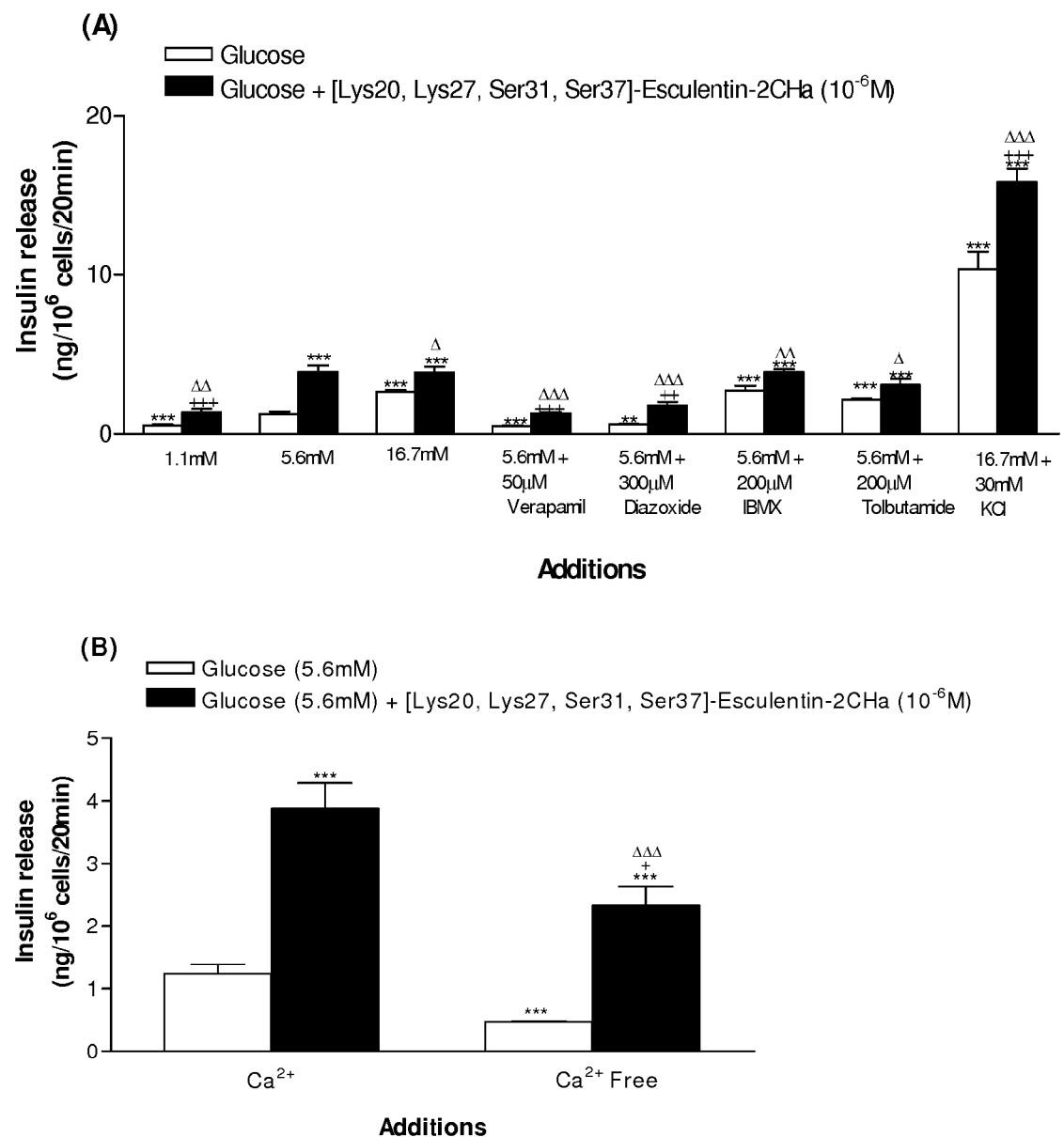
FIG. 13 illustrates the effects of [Lys20, Lys27, Ser31, Ser37]-esculentin-2CHa on insulin release from BRIN-BD11 cells in the presence or absence of known modulators of insulin secretion (A) and extracellular calcium (B). Values are Mean±SEM (n=6). *P<0.05, P<0.01, *P<0.001 compared to 5.6 mM glucose alone (A) in the presence of extracellular calcium (B). +P<0.05, ++P<0.01, +++P<0.001 compared to 5.6 mM glucose in the presence of the peptide (A) and in the presence of extracellular calcium (B). ΔP<0.05, ΔΔP<0.01, ΔΔΔP<0.001 compared to respective incubation in the absence of the peptide.
Figure 14:
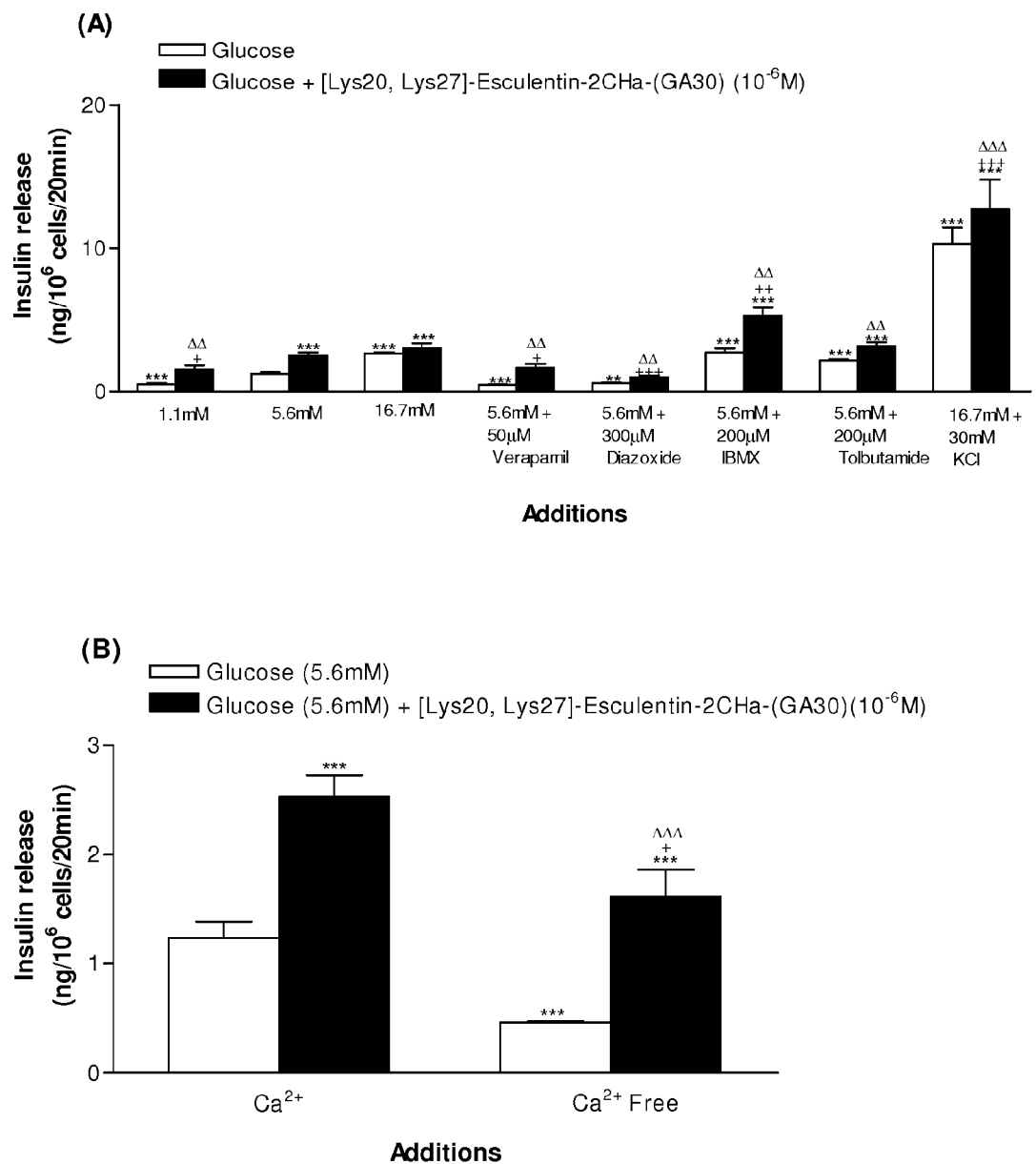
FIG. 14 illustrates the effects of [Lys20, Lys27]-esculentin-2CHa-(GA30) on insulin release from BRIN-BD11 cells in the presence or absence of known modulators of insulin secretion (A) and extracellular calcium (B). Values are Mean±SEM (n=6). *P<0.05, P<0.01, *P<0.001 compared to 5.6 mM glucose alone (A) in the presence of extracellular calcium (B). +P<0.05, ++P<0.01, +++P<0.001 compared to 5.6 mM glucose in the presence of the peptide (A) and in the presence of extracellular calcium (B). ΔP<0.05, ΔΔP<0.01, ΔΔΔP<0.001 compared to respective incubation in the absence of the peptide.
Figure 15:
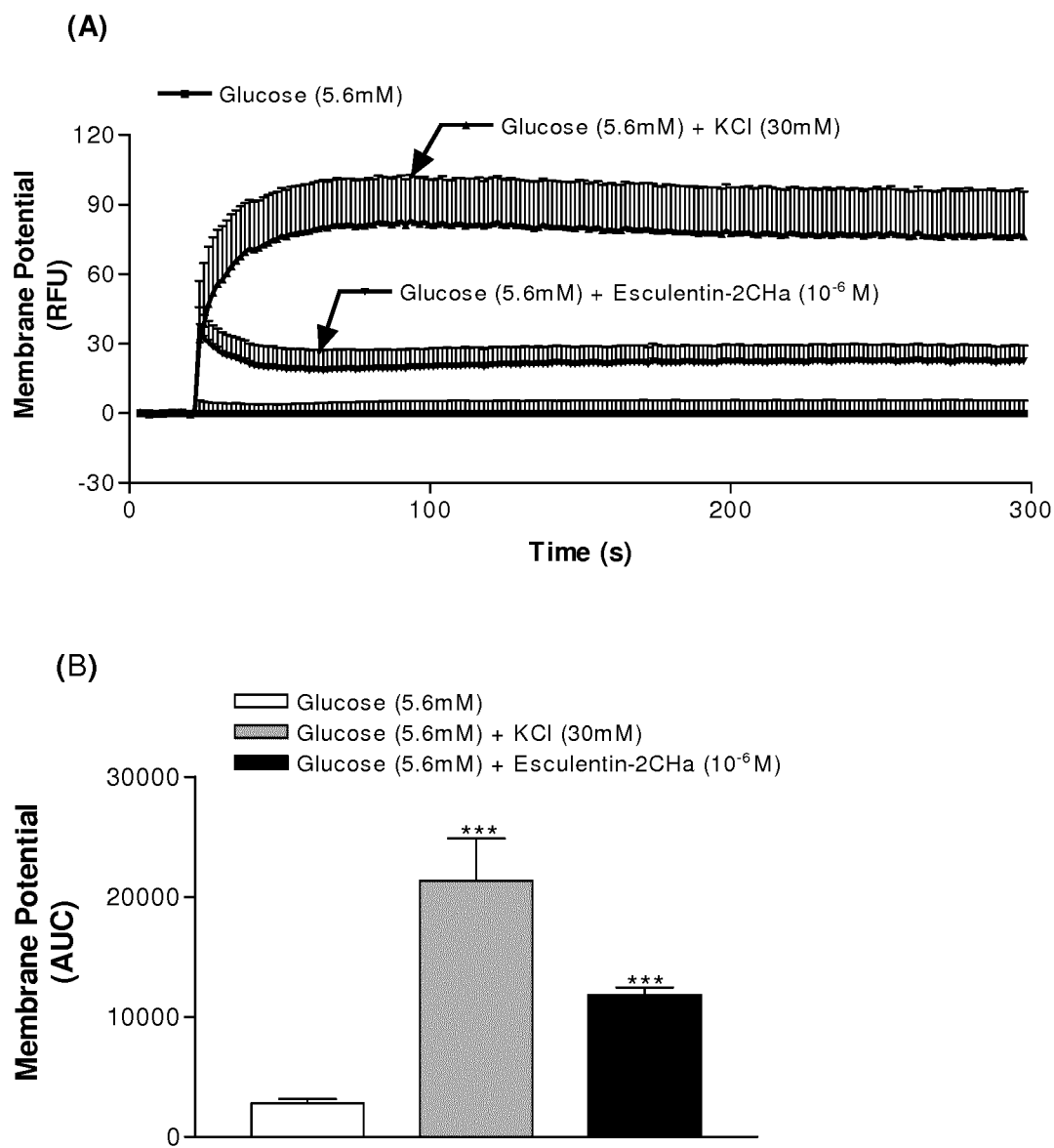
FIG. 15 illustrates the effects of esculentin-2CHa on membrane potential in BRIN-BD11 cells expressed as (A) RFU and (B) area under the curve. Values are Mean±SEM (n=6). *P<0.001, P<0.01 compared to 5.6 mM glucose alone.
Figure 18:
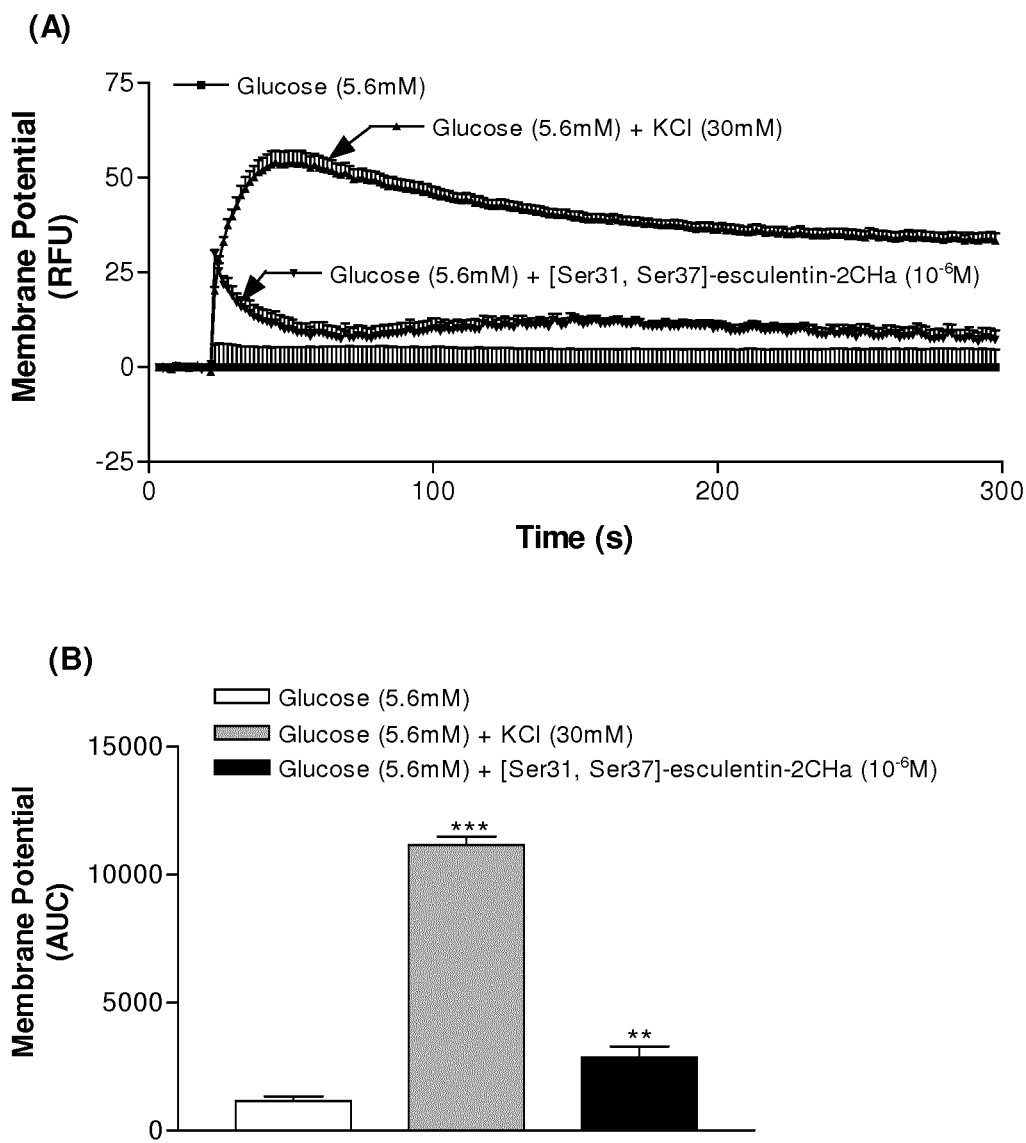
FIG. 18 illustrates the effects of [Ser31, Ser37]-esculentin-2CHa on membrane potential in BRIN-BD11 cells expressed as (A) RFU and (B) area under the curve. Values are Mean±SEM (n=6). *P<0.001, P<0.01 compared to 5.6 mM glucose alone.
Figure 19:
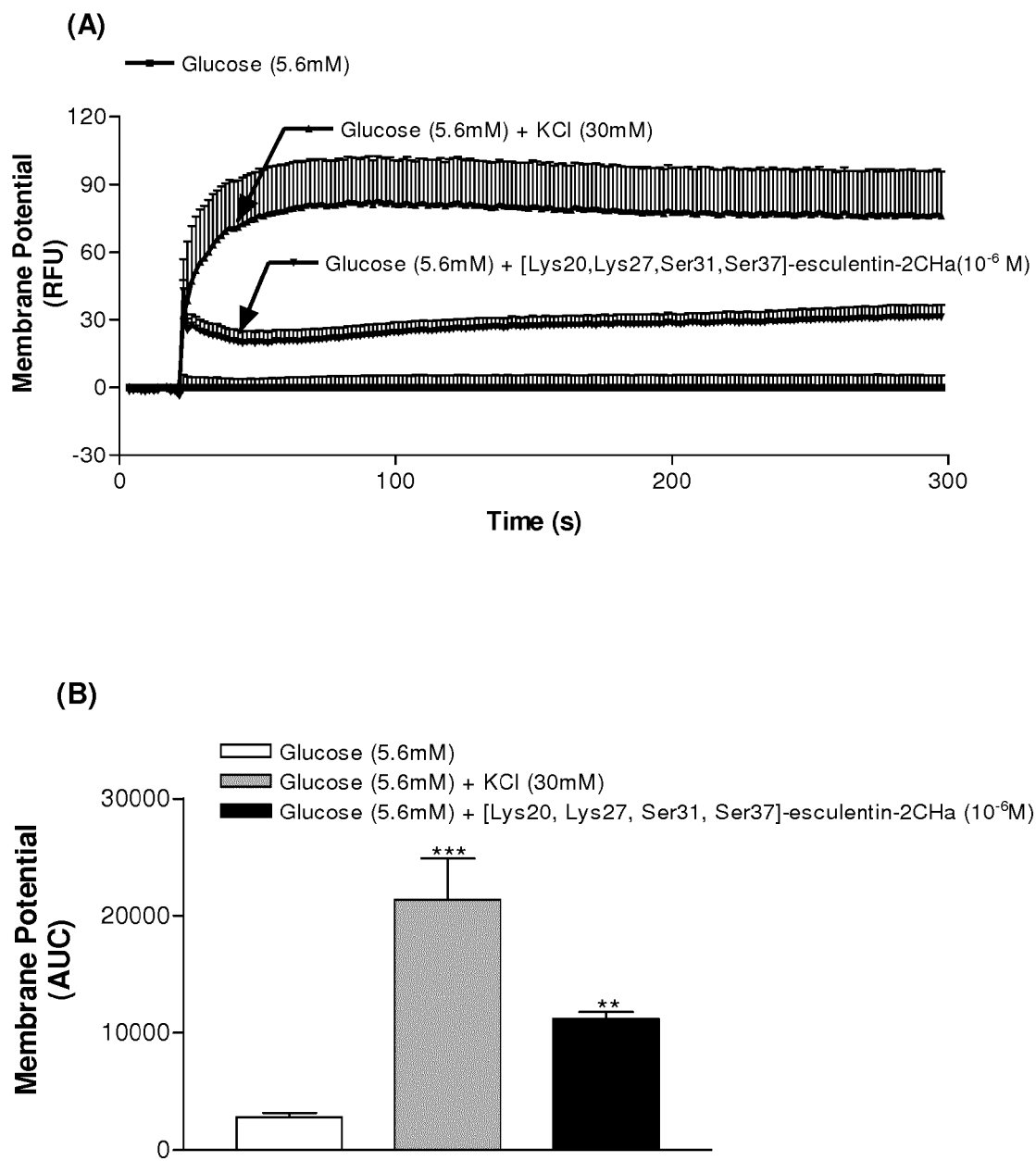
FIG. 19 illustrates the effects of [Lys20, Lys27, Ser31, Ser37]-esculentin-2CHa on membrane potential in BRIN-BD11 cells expressed as (A) RFU and (B) area under the curve. Values are Mean±SEM (n=6). *P<0.001, P<0.01 compared to 5.6 mM glucose alone.
Figure 20:
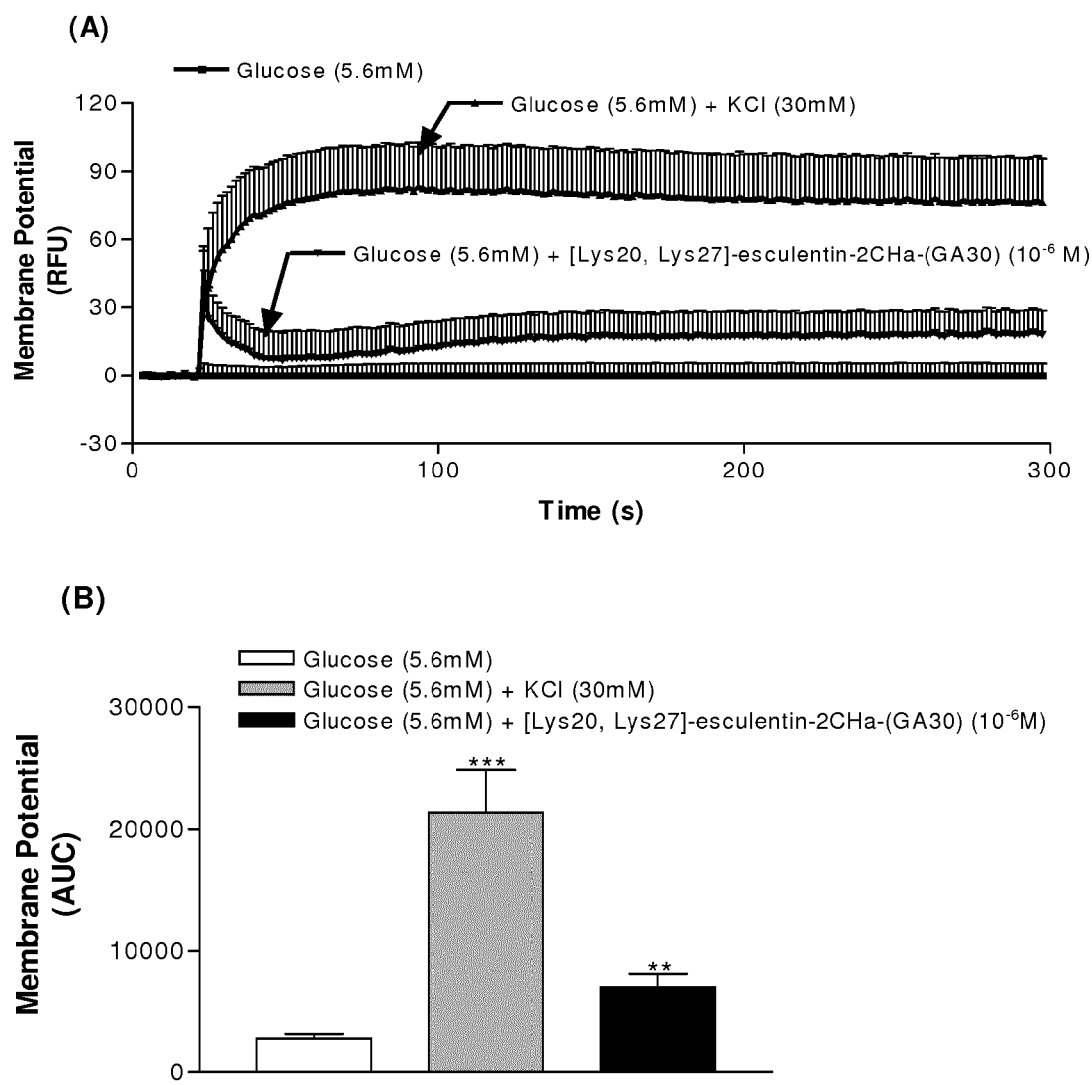
FIG. 20 illustrates the effects of [Lys20, Lys27]-esculentin-2CHa-(GA30) on membrane potential in BRIN-BD11 cells expressed as (A) RFU and (B) area under the curve. Values are Mean±SEM (n=6). *P<0.001, P<0.01 compared to 5.6 mM glucose alone.
Figure 21:
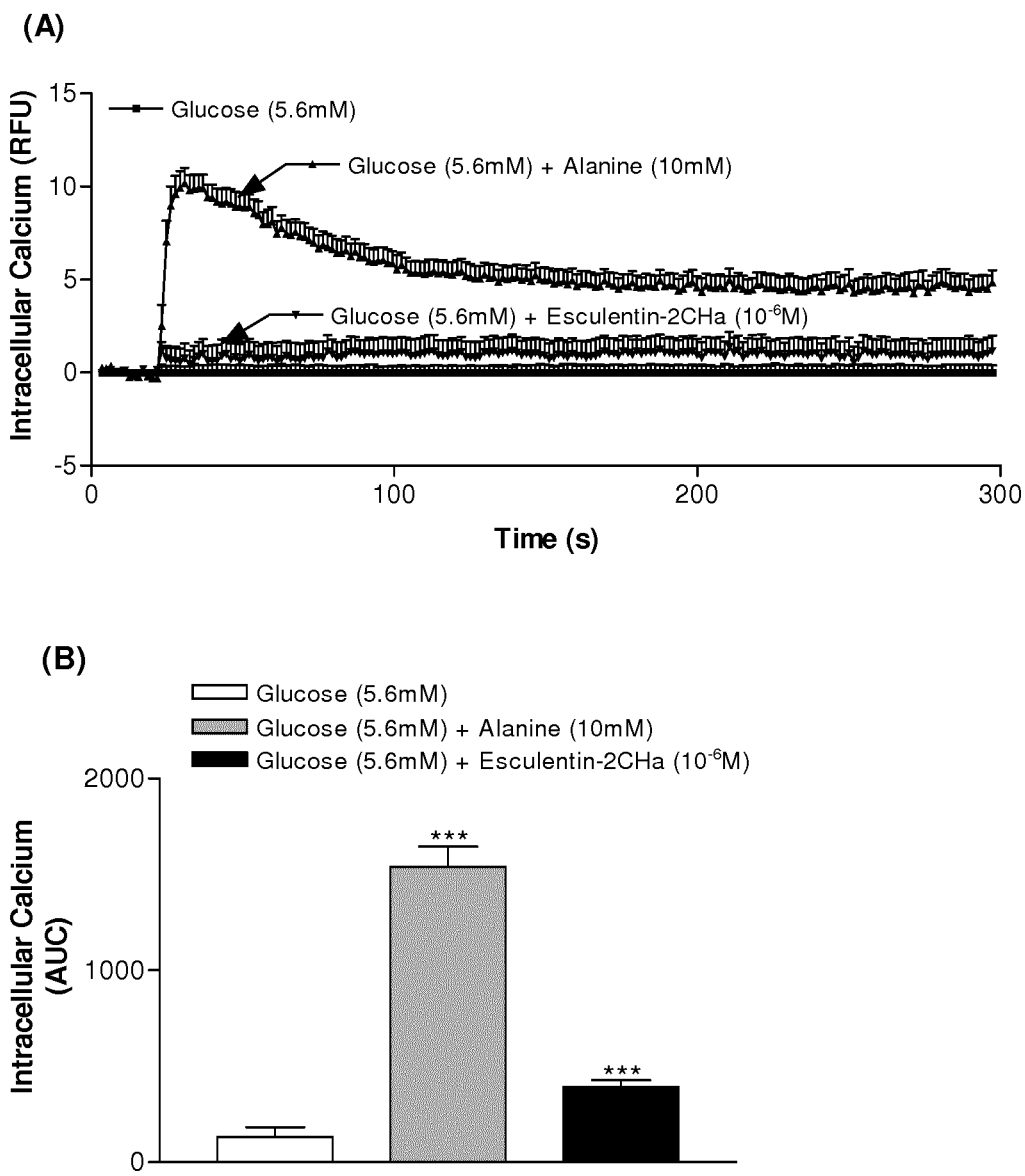
FIG. 21 illustrates the effects of esculentin-2CHa on intracellular calcium in BRIN-BD11 cells expressed as (A) RFU and (B) area under the curve. Values are Mean±SEM (n=8). ***P<0.001 compared to 5.6 mM glucose alone.
Figure 22:
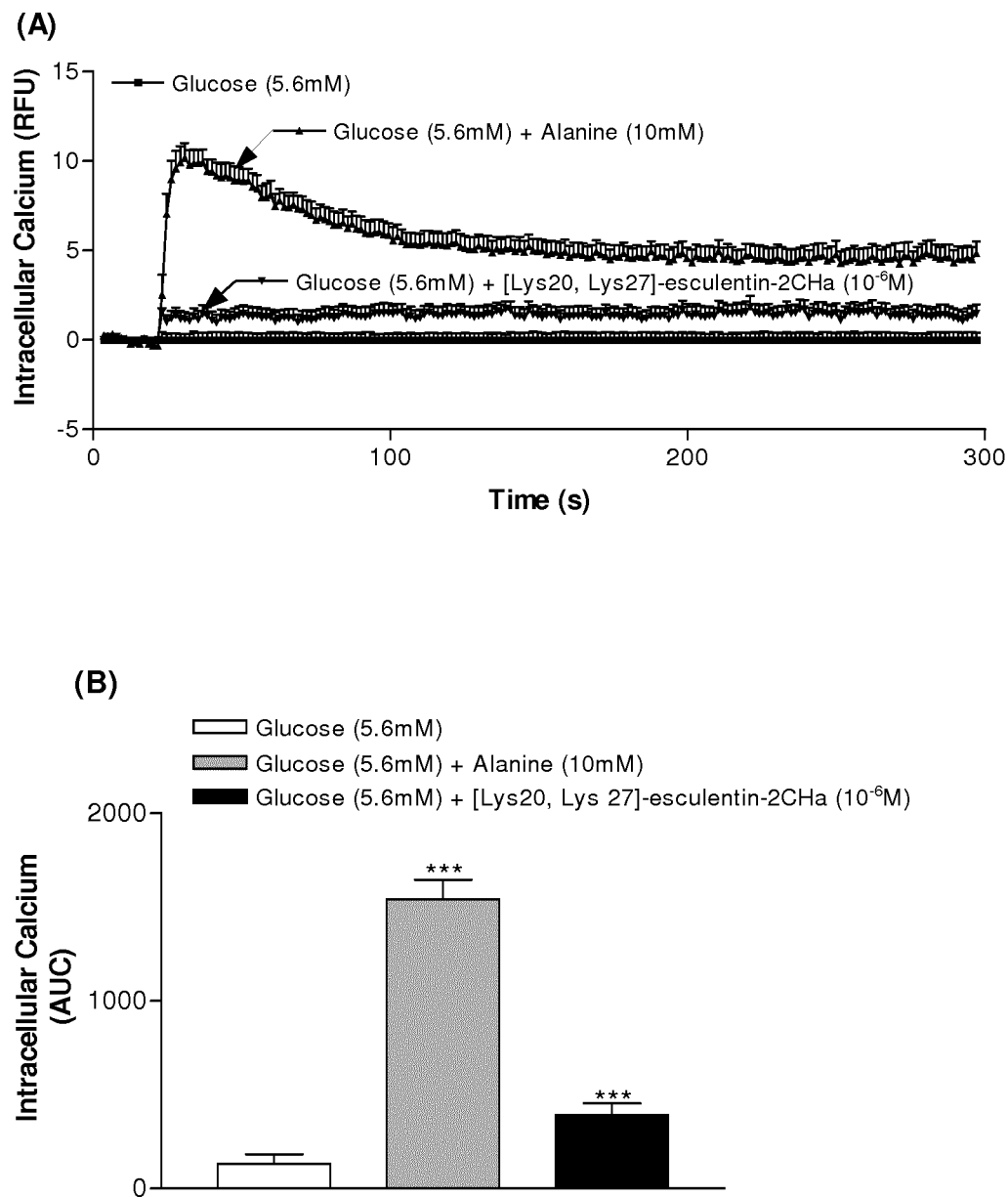
FIG. 22 illustrates the effects of [Lys20, Lys27]-esculentin-2CHa on intracellular calcium in BRIN-BD11 cells expressed as (A) RFU and (B) area under the curve. Values are Mean±SEM (n=8). ***P<0.001 compared to 5.6 mM glucose alone.
Figure 23:
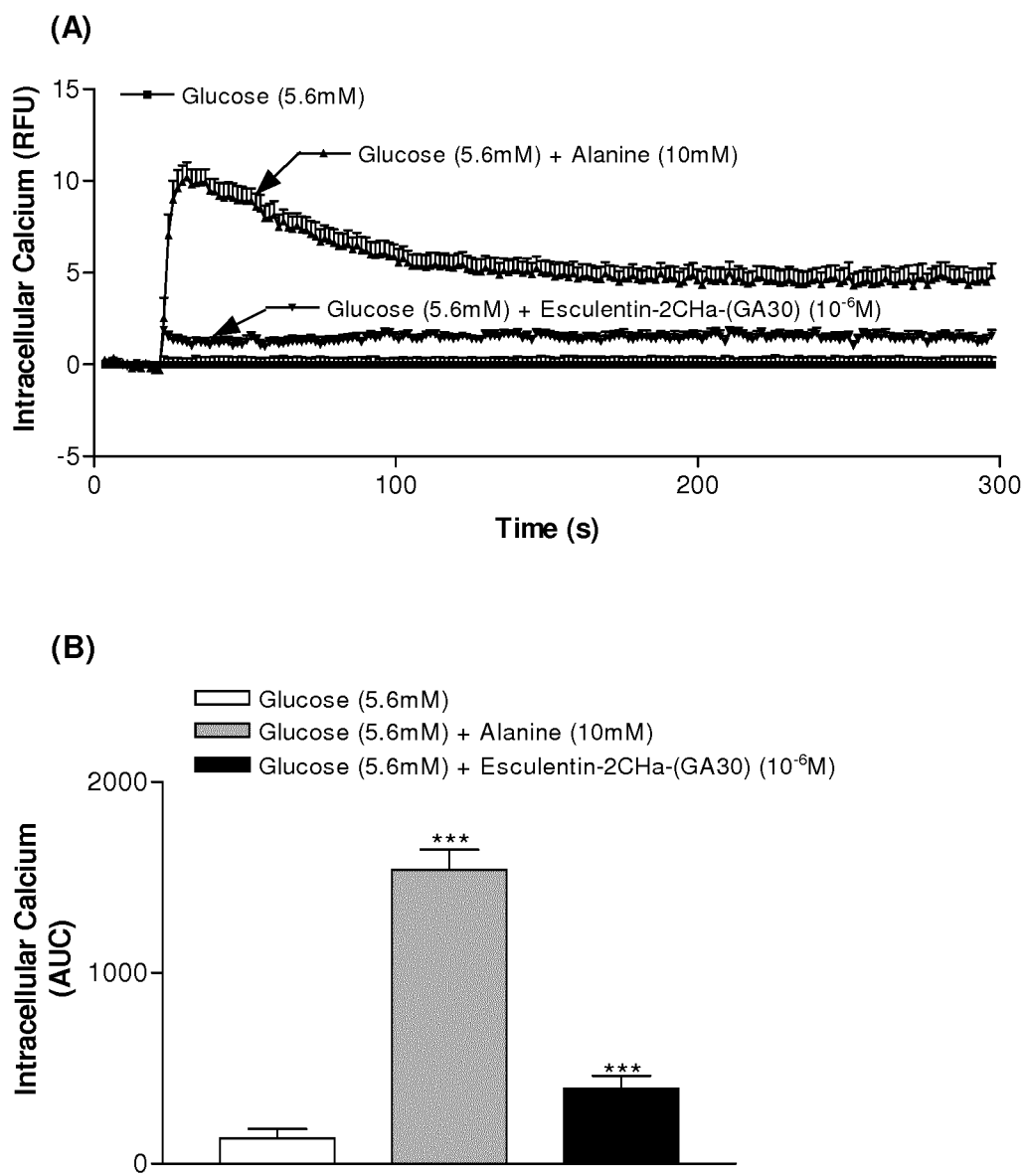
FIG. 23 illustrates the effects of esculentin-2CHa-(GA30) on intracellular calcium in BRIN-BD11 cells expressed as (A) RFU and (B) area under the curve. Values are Mean±SEM (n=8). ***P<0.001 compared to 5.6 mM glucose alone.
Figure 25:
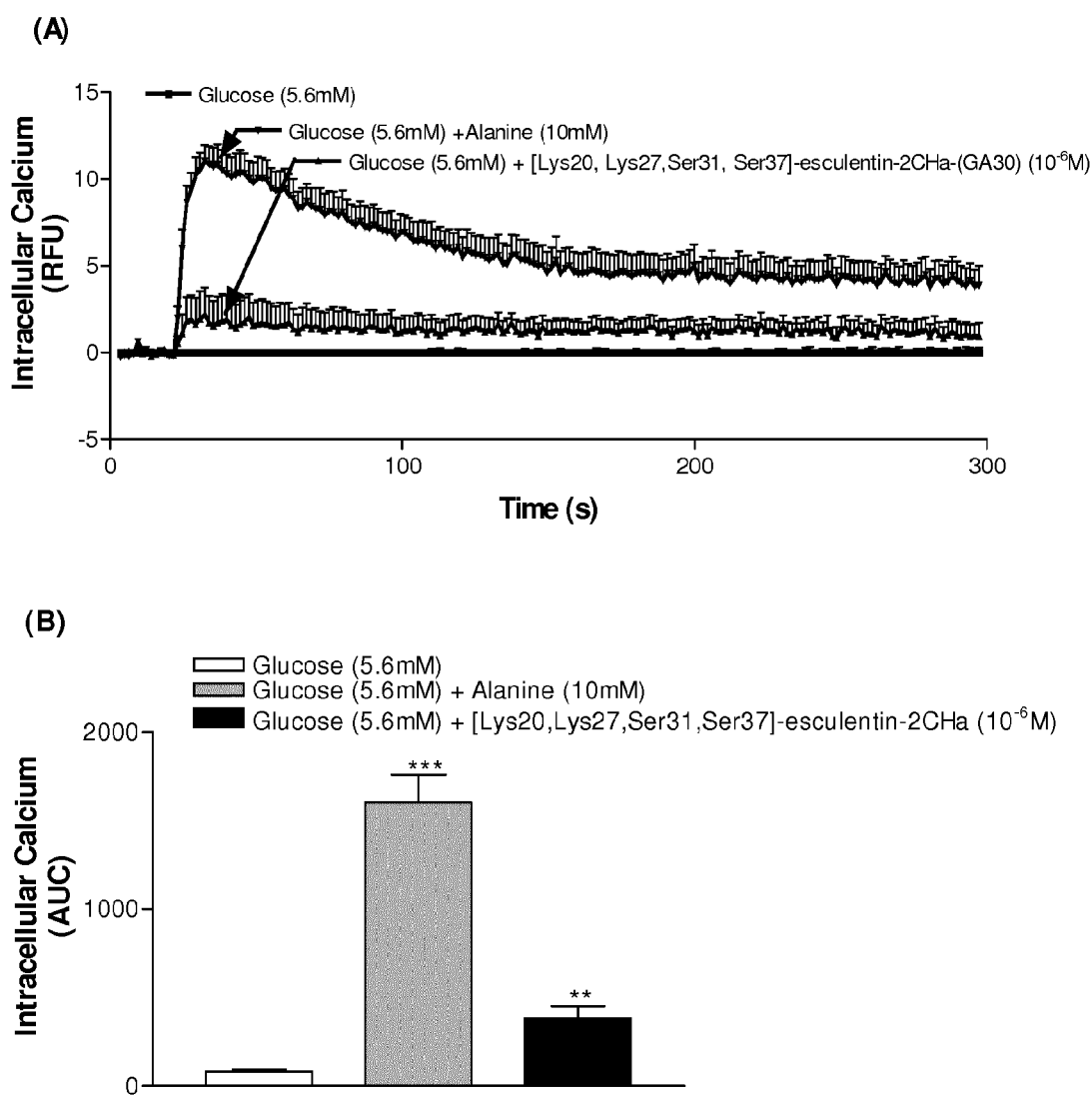
FIG. 25 illustrates the effects of [Lys20, Lys27, Ser31, Ser37]-esculentin-2CHa on intracellular calcium in BRIN-BD11 cells expressed as (A) RFU and (B) area under the curve. Values are Mean±SEM (n=6). P<0.01, *P<0.001 compared to 5.6 mM glucose alone.
Figure 27:
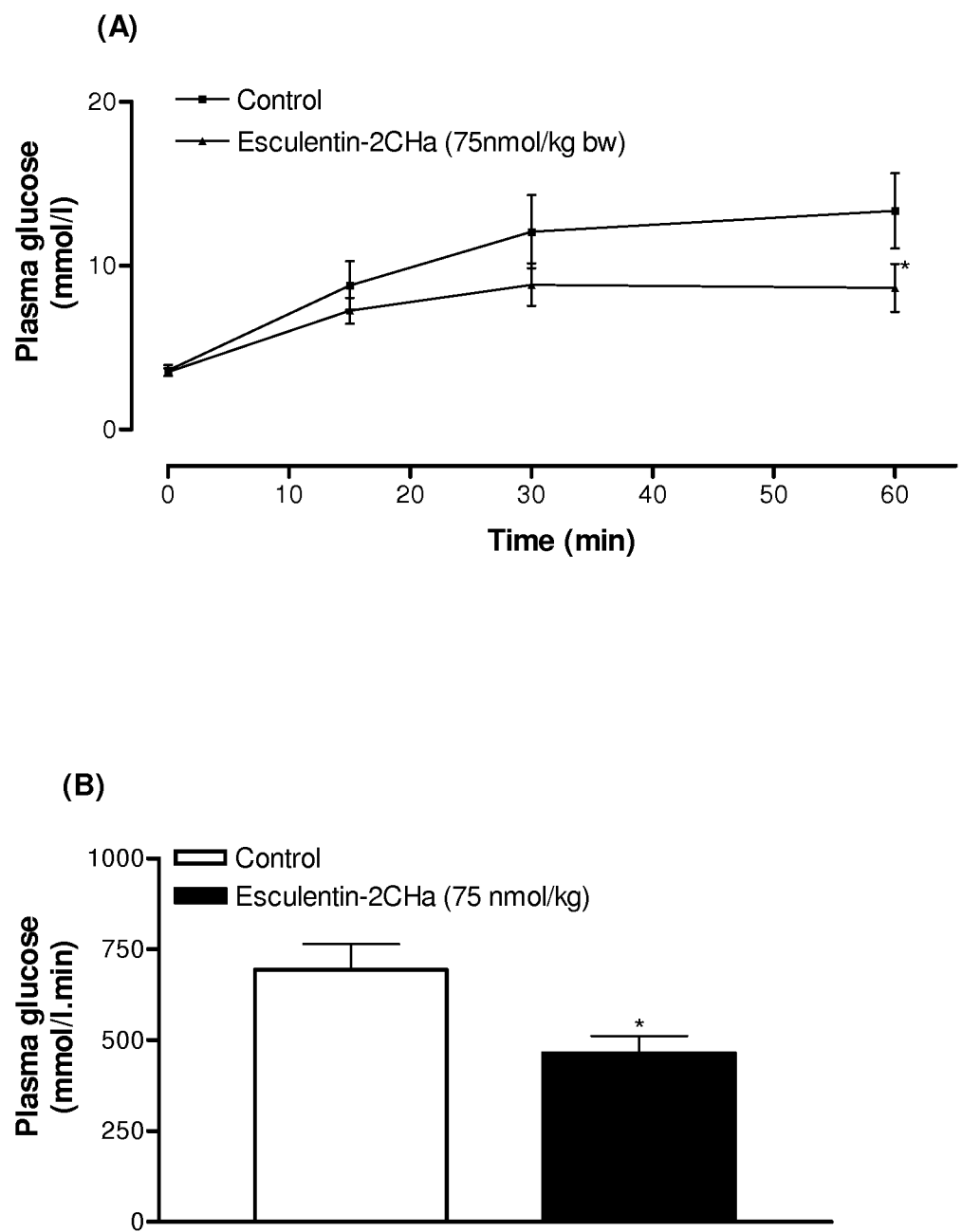
FIG. 27 illustrates the effects of esculentin-2CHa on acute glucose tolerance in lean Swiss TO mice expressed as (A) line graph and (B) area under the curve. Plasma glucose was measured prior to and after intraperitoneal injection of glucose (180 mmol) alone (control) or in combination with peptide (75 nmol/kg bw). Values are Mean±SEM for 8 mice. *P<0.05 compared control.
Figure 28:
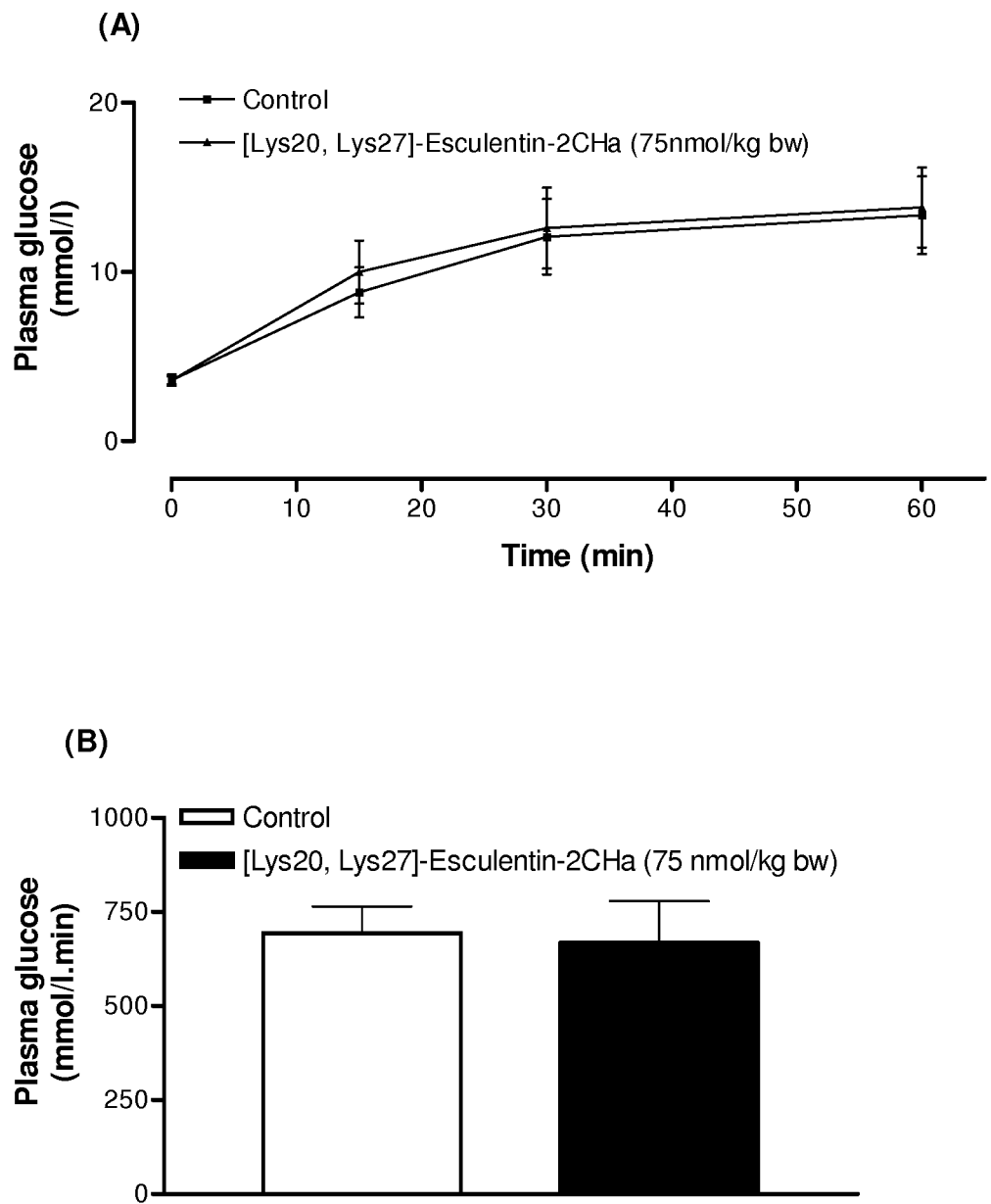
FIG. 28 illustrates the effects of [Lys20, Lys27]-esculentin-2CHa on acute glucose tolerance in lean Swiss TO mice expressed as (A) line graph and (B) area under the curve. Plasma glucose was measured prior to and after intraperitoneal injection of glucose (180 mmol) alone (control) or in combination with peptide (75 nmol/kg bw). Values are Mean±SEM for 8 mice.
Figure 29:
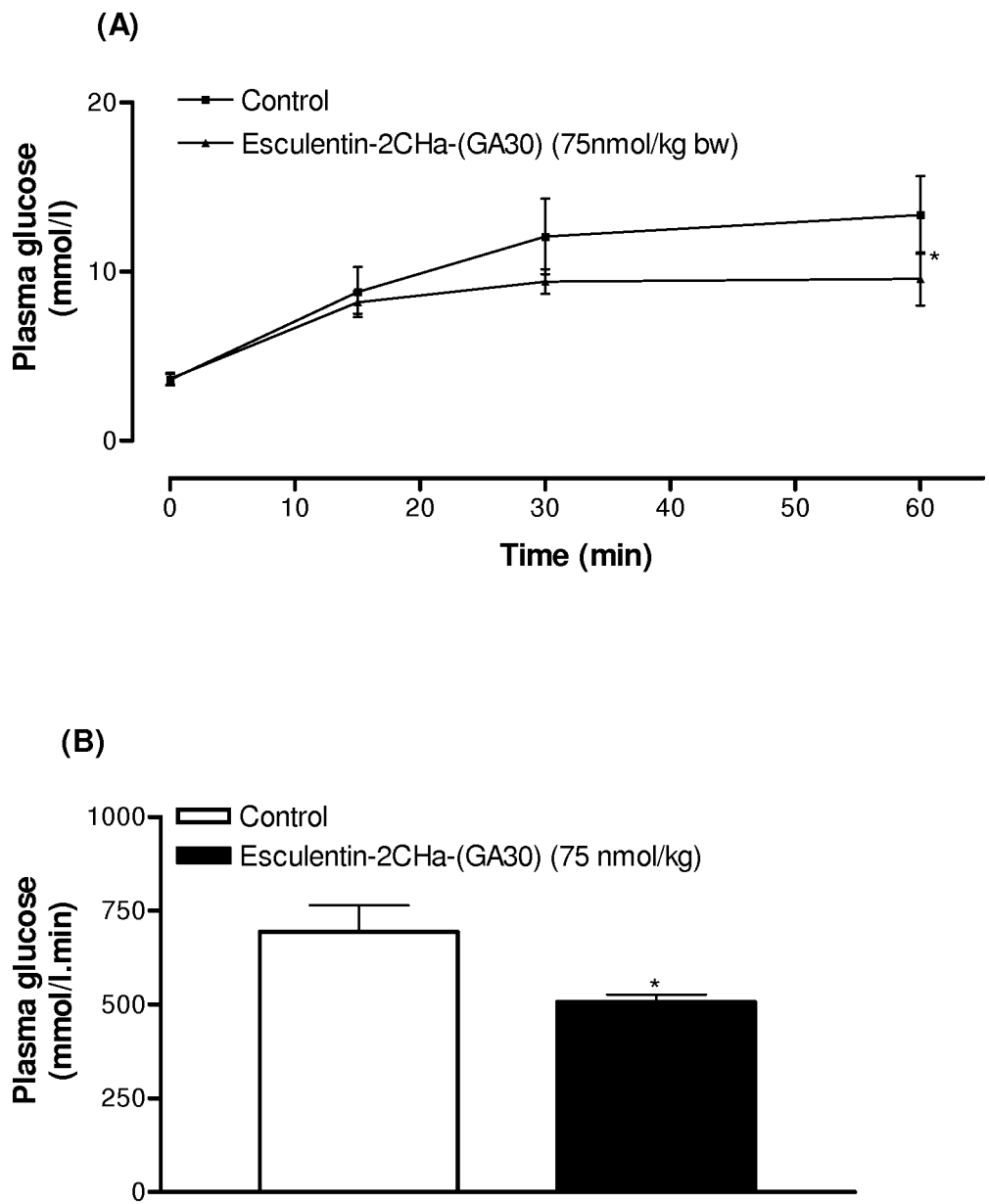
FIG. 29 illustrates the effects of esculentin-2CHa-(GA30) on acute glucose tolerance in lean Swiss TO mice expressed as (A) line graph and (B) area under the curve. Plasma glucose was measured prior to and after intraperitoneal injection of glucose (180 mmol) alone (control) or in combination with peptide (75 nmol/kg bw). Values are Mean±SEM for 8 mice. *P<0.05 compared to control.
Figure 30:
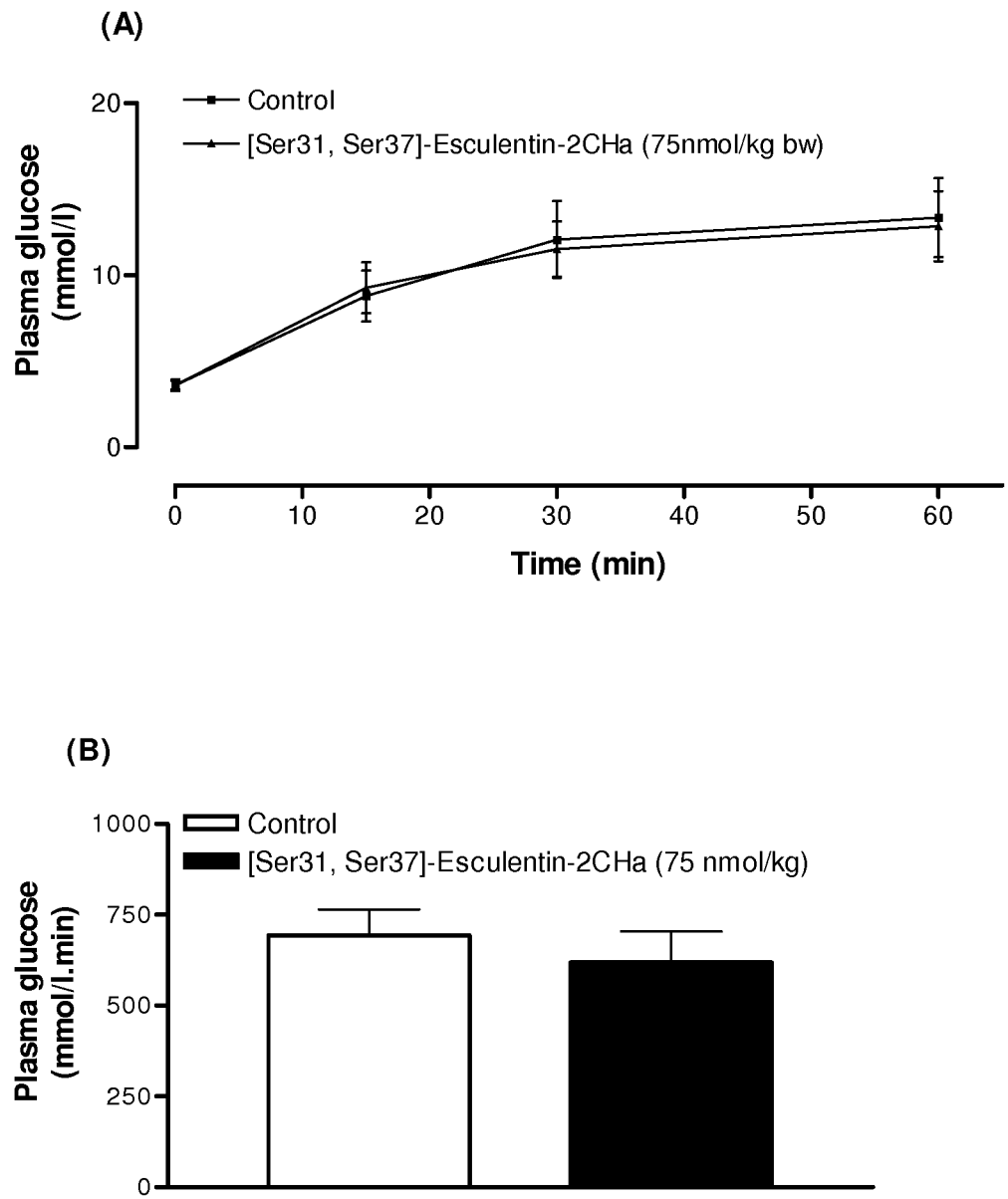
FIG. 30 illustrates the effects of [Ser31, Ser7]-esculentin-2CHa on acute glucose tolerance in lean Swiss TO mice expressed as (A) line graph and (B) area under the curve. Plasma glucose was measured prior to and after intraperitoneal injection of glucose (180 mmol) alone (control) or in combination with peptide (75 nmol/kg bw). Values are Mean±SEM for 8 mice.
Figure 31:
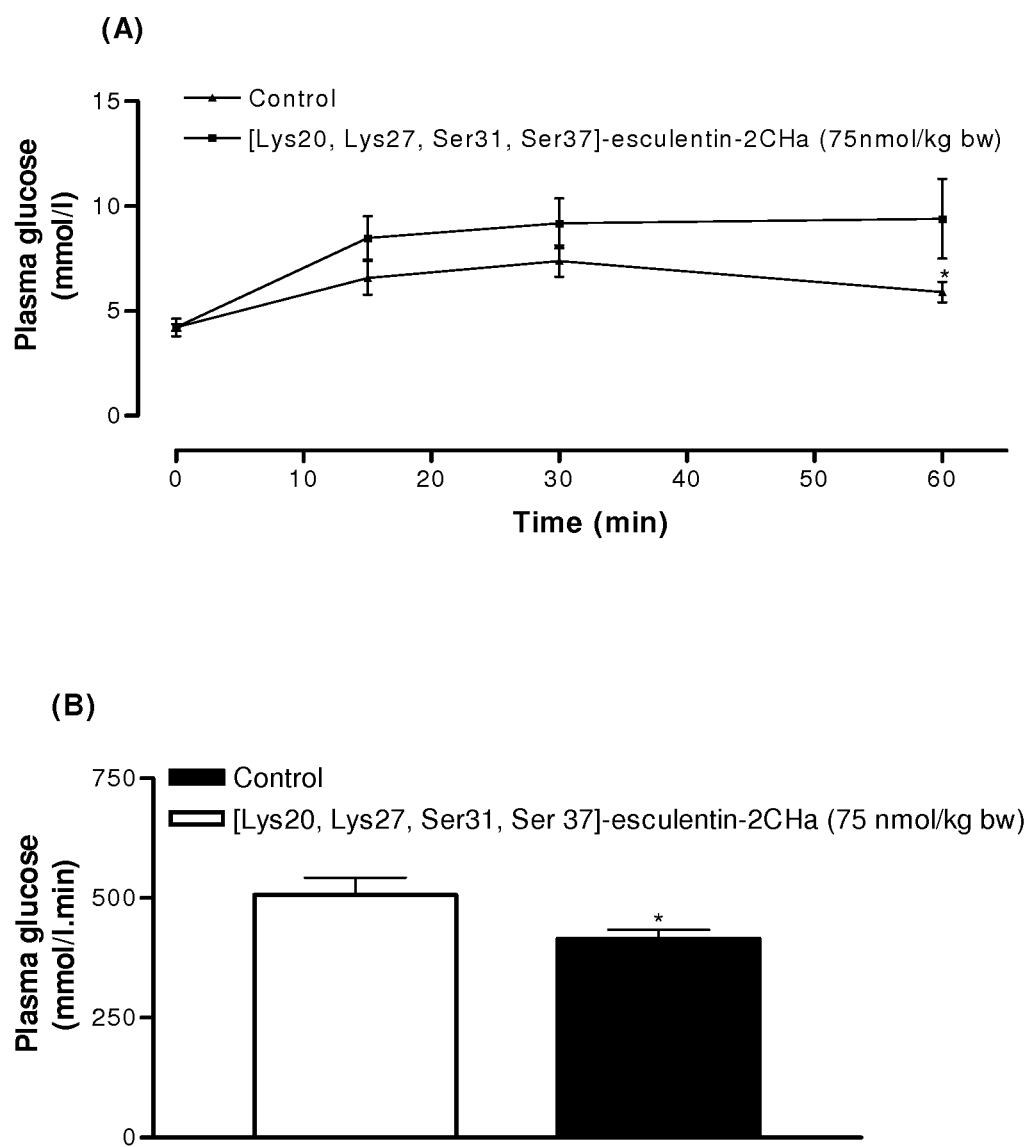
FIG. 31 illustrates the effects of [Lys20, Lys27, Ser31, Ser37]-esculentin-2CHa-(GA30) on acute glucose tolerance in lean Swiss TO mice expressed as (A) line graph and (B) area under the curve. Plasma glucose was measured prior to and after intraperitoneal injection of glucose (180 mmol) alone (control) or in combination with peptide (75 nmol/kg bw). Values are Mean±SEM for 8 mice. *P<0.05 compared to mice in control group.
Figure 32:
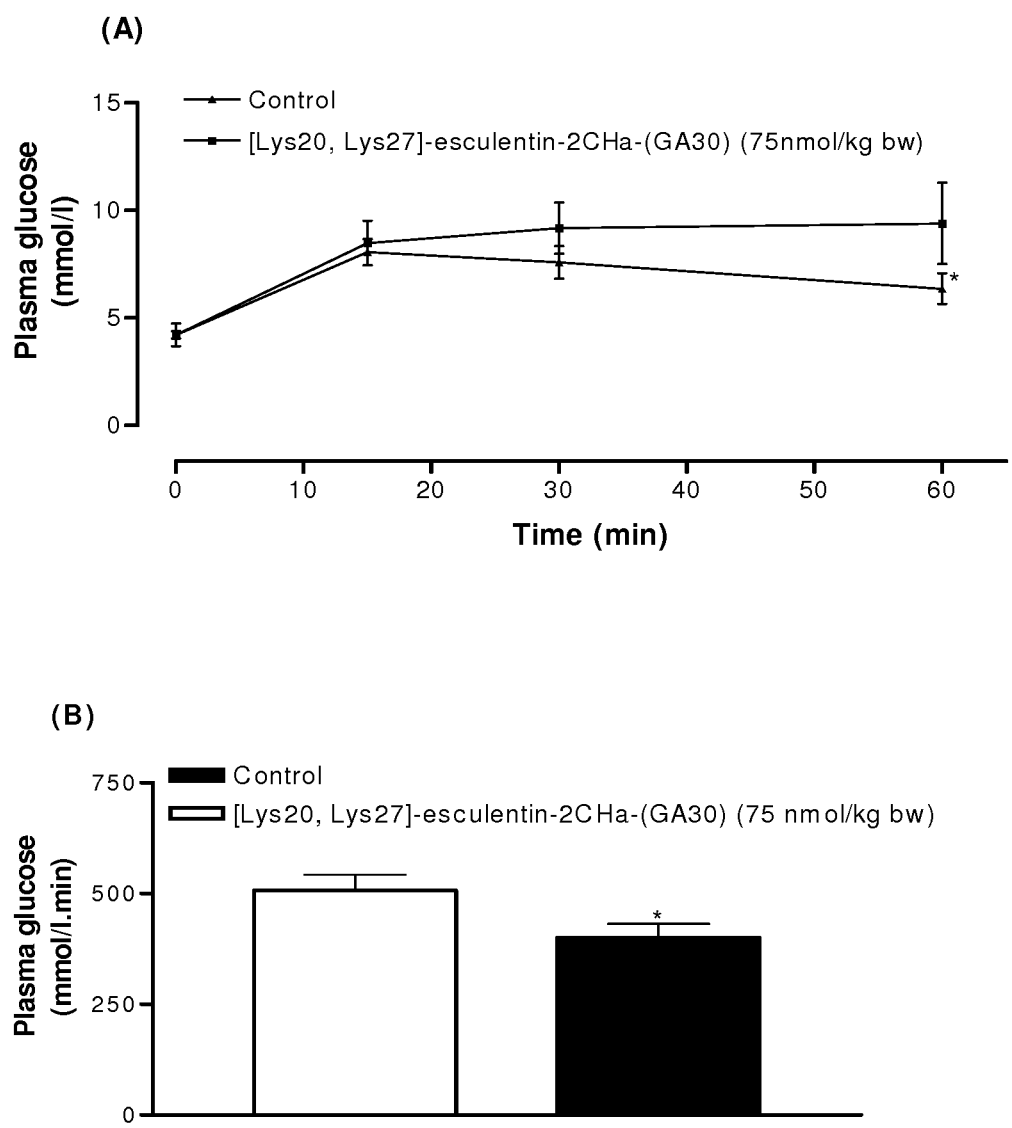
FIG. 32 illustrates the effects of [Lys20, Lys27]-esculentin-2CHa-(GA30) on acute glucose tolerance in lean Swiss TO mice expressed as (A) line graph and (B) area under the curve. Plasma glucose was measured prior to and after intraperitoneal injection of glucose (180 mmol) alone (control) or in combination with peptide (75 nmol/kg bw). Values are Mean±SEM for 8 mice. *P<0.05 compared to mice in control group.
Figure 33:
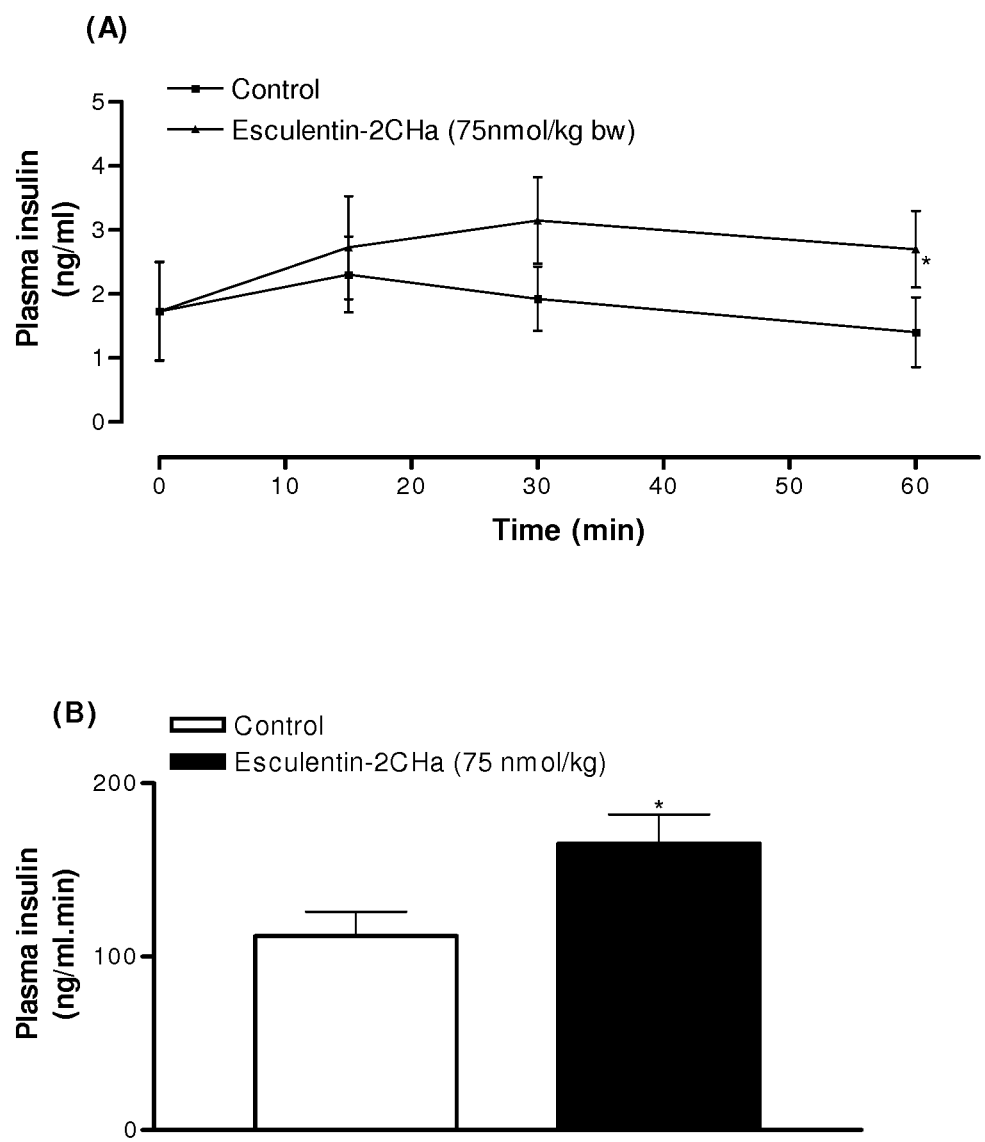
FIG. 33 illustrates the effects of esculentin-2CHa on plasma insulin in lean Swiss TO mice expressed as (A) line graph and (B) area under the curve. Plasma insulin was measured prior to and after intraperitoneal injection of glucose (180 mmol) alone (control) or in combination with peptide (75 nmol/kg bw). Values are Mean±SEM for 8 mice. *P<0.05 compared control.
Figure 34:
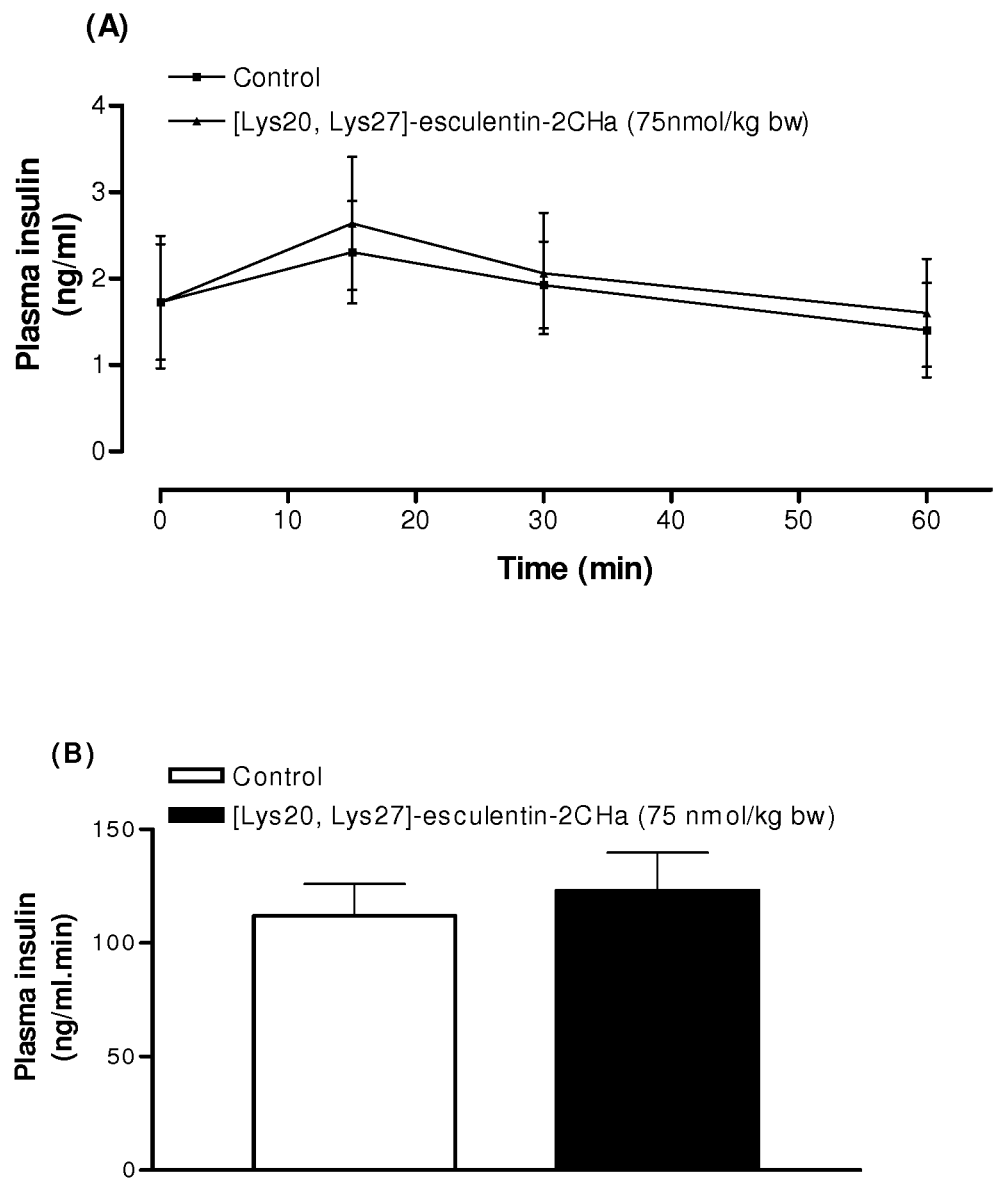
FIG. 34 illustrates the effects of [Lys20, Lys27]-esculentin-2CHa on plasma insulin in lean Swiss TO mice expressed as (A) line graph and (B) area under the curve. Plasma insulin was measured prior to and after intraperitoneal injection of glucose (180 mmol) alone (control) or in combination with peptide (75 nmol/kg bw). Values are Mean±SEM for 8 mice.
Figure 35:
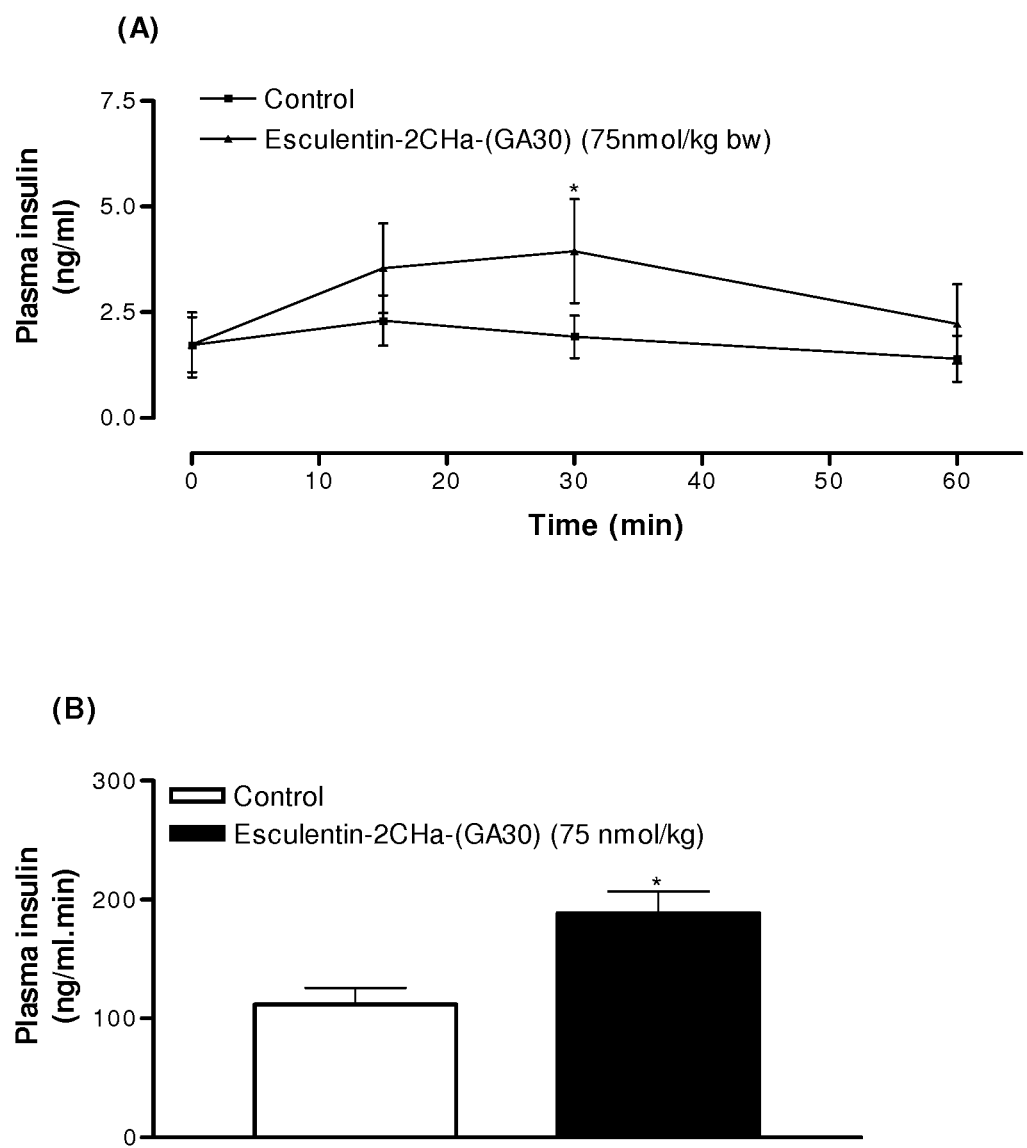
FIG. 35 illustrates the effects of esculentin-2CHa-(GA30) on plasma insulin in lean Swiss TO mice expressed as (A) line graph and (B) area under the curve. Plasma insulin was measured prior to and after intraperitoneal injection of glucose (180 mmol) alone (control) or in combination with peptide (75 nmol/kg bw). Values are Mean±SEM for 8 mice. **P<0.01 compared control.
Figure 36:
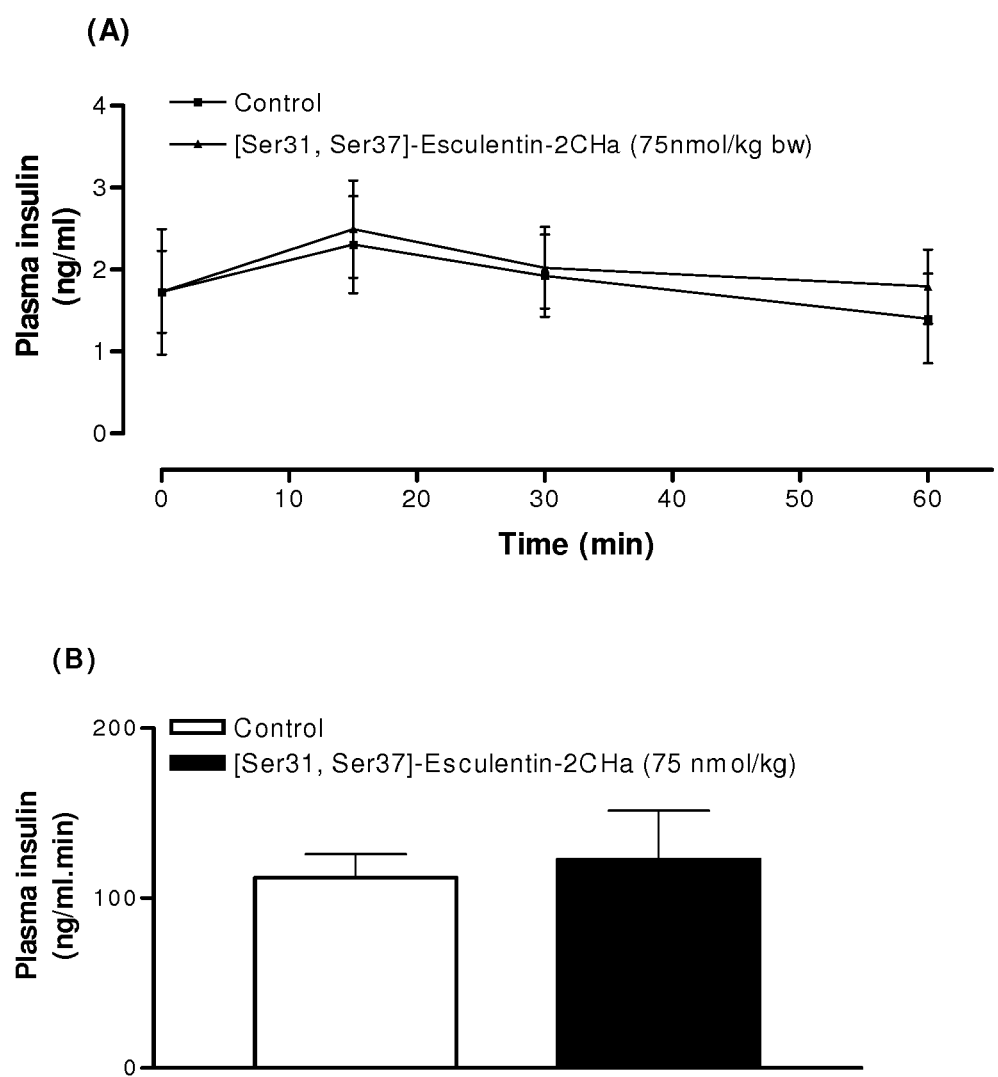
FIG. 36 illustrates the effects of [Ser31, Ser37]-esculentin-2CHa on plasma insulin in lean Swiss TO mice expressed as (A) line graph and (B) area under the curve. Plasma insulin was measured prior to and after intraperitoneal injection of glucose (180 mmol) alone (control) or in combination with peptide (75 nmol/kg bw). Values are Mean±SEM for 8 mice.
Figure 37:
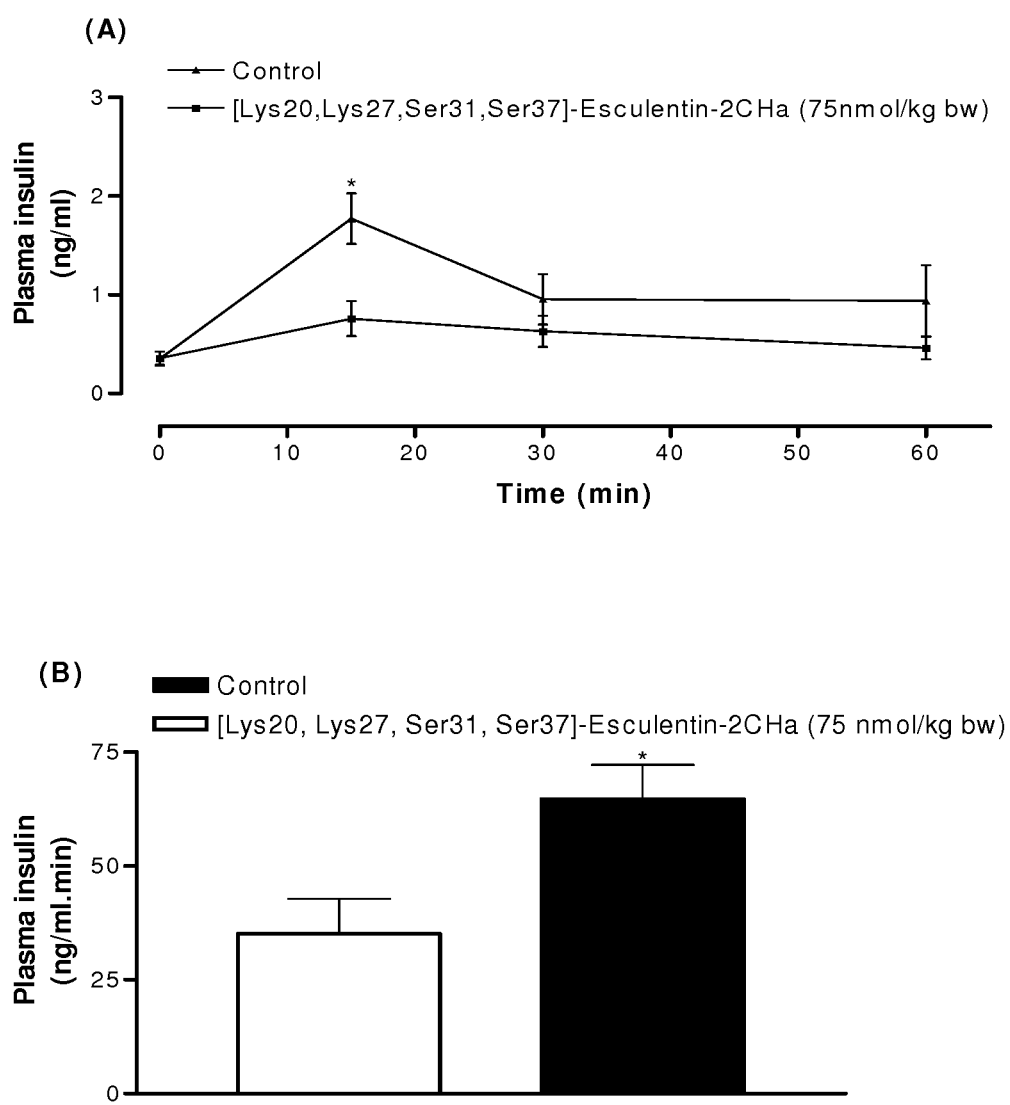
FIG. 37 illustrates the effects of [Lys20, Lys27, Ser31, Ser37]-esculentin-2CHa on plasma insulin in lean Swiss TO mice expressed as (A) line graph and (B) area under the curve. Plasma insulin was measured prior to and after intraperitoneal injection of glucose (180 mmol) alone (control) or in combination with peptide (75 nmol/kg bw). Values are Mean±SEM for 8 mice. *P<0.05 compared to control.
Figure 38:
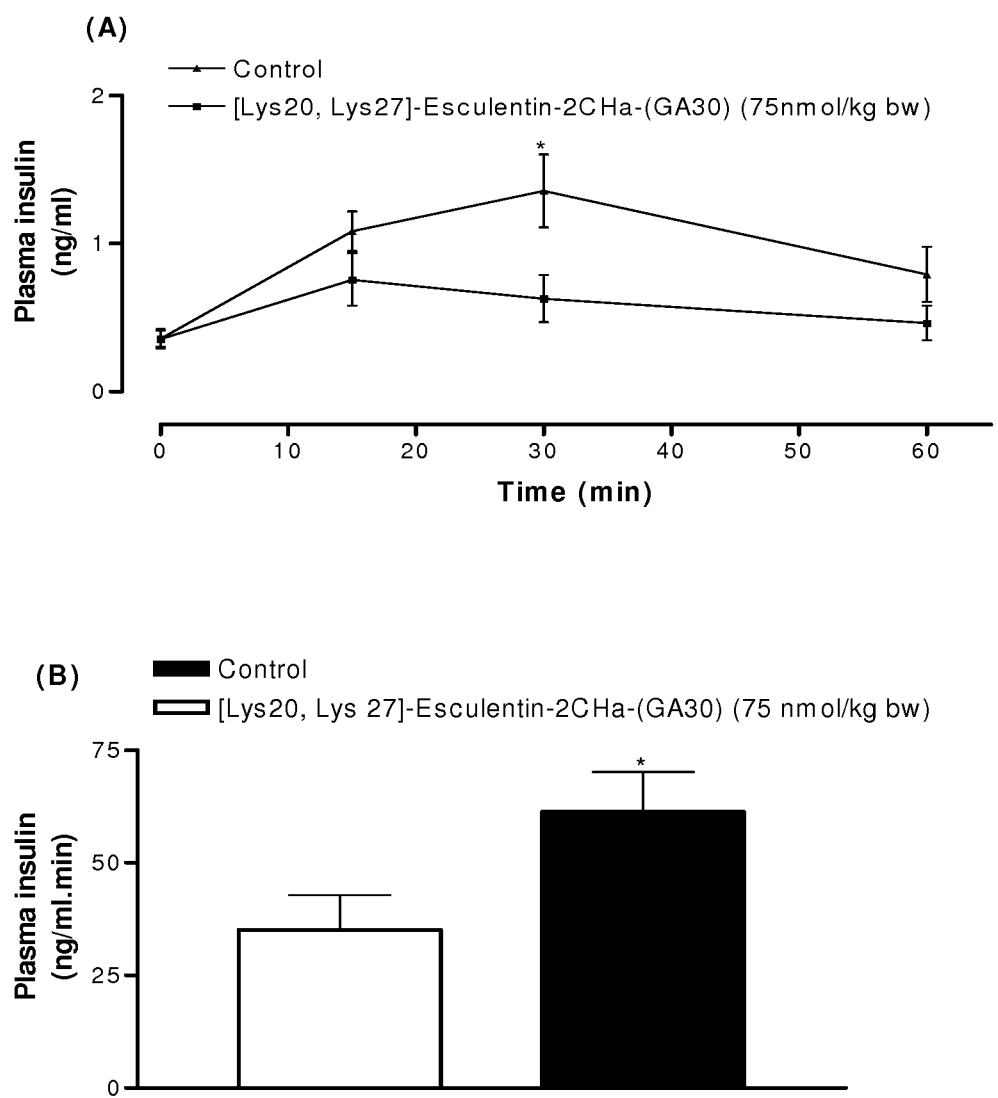
FIG. 38 illustrates the effects of [Lys20, Lys27]-esculentin-2CHa-(GA30) on plasma insulin in lean Swiss TO mice expressed as (A) line graph and (B) area under the curve. Plasma insulin was measured prior to and after intraperitoneal injection of glucose (180 mmol) alone (control) or in combination with peptide (75 nmol/kg bw). Values are Mean±SEM for 8 mice. *P<0.05 compared to control.

The in vitro effects of administration of peptides according to the present invention on insulin release were assessed as described above herein. Results obtained confirmed the dose-dependent stimulatory effects of esculentin-2CHa (FIG. 1A). Moreover, these effects were retained in all the substituted analogues (FIG. 2A-5A). Interestingly, esculentin-2CHa(GA30), the shortest version of the synthetic analogue appears to be more potent than the native peptide at lower concentrations (FIG. 7B). These effects were not associated with beta cell cytotoxicity (FIG. 1B-6B).

The insulin-release stimulatory effects of esculentin-2CHa and its synthetic analogues were retained in the presence of high (16.7 mM) glucose concentration. These effects were inhibited but not abolished in the presence of verapamil and diazoxide (FIGS. 9A-14A). Chelation of extracellular calcium also resulted in a significant reduction in the insulin-releasing effects of the peptides (FIGS. 9B-14B). These results suggest that the actions of esculentin-2CHa and its analogues are physiologic and may involve well-known pathways of insulin secretion. The peptides also enhanced membrane depolarization (FIGS. 15-20) and caused significant increase in intracellular calcium (FIGS. 21-26). These observations further confirm the involvement of the $K_{ATP}$-dependent pathway in the actions of the peptides. All the peptides were degraded within 2 hours of incubation with mouse plasma.

TABLE 1

HPLC and mass spectrometry analysis of Esculentin-2CHa-(GA30) and its analogues and GLP-1 (7-36) NH2

| Peptide | Theoretical molecular mass | Measured molecular mass | Retention time (minutes) |
|---|---|---|---|
| Esculentin-2CHa-(GA30) | 3052.62 | 3053.73 | 30.6 |
| [D-Arg7]-Esculentin-2CHa-(GA30) | 3052.62 | 3053.17 | 30.7 |
| [D-Lys15]-Esculentin-2CHa-(GA30) | 3052.62 | 3052.04 | 27.8 |
| [D-Lys23]-Esculentin-2CHa-(GA30) | 3052.62 | 3054.03 | 26.5 |
| [D-Lys15, D-Lys23]-Esculentin-2CHa-(GA30) | 3052.62 | 3053.82 | 24.9 |
| [D-Arg7, D-Lys15, D-Lys23]-Esculentin-2CHa-(GA30) | 3052.62 | 3053.92 | 21.8 |
| [L-Orn15, L-Orn23]-Esculentin-2CHa-(GA30) | 3024.56 | 3026.31 | 30.2 |
| Esculentin-2CHa-(GA30)-NH2 | 3051.63 | 3050.99 | 31.8 |
| Lys15-Octanoate-Esculentin-2CHa-(GA30) | 3178.65 | 3177.56 | 36.1 |
| Lys23-Octanoate-Esculentin-2CHa-(GA30) | 3178.65 | 3176.62 | 36.2 |

Example 2—Effects on Body Weight and Energy Intake

In the present description and drawings, Peptide 2 represents Esculentin-2CHa-(GA30), Peptide 7 represents [D-Arg7, D-Lys15,D-Lys23]-esculentin-2CHa-(GA30), and Peptide 10 represents Lys15-octanoate-Esculentin-2CHa-(GA30).

Figure 40:
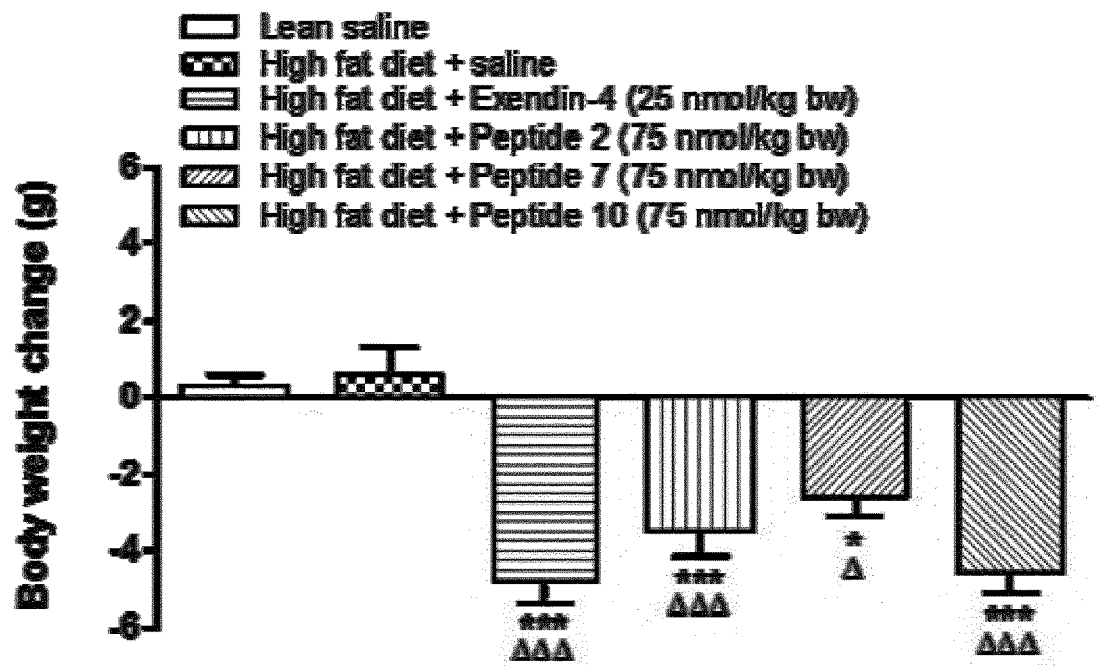
FIG. 40 illustrates the effect of administration of Exendin-4, Esculentin-2CHa-(GA30), [D-Arg7, D-Lys15,D-Lys23]-esculentin-2CHa-(GA30), and Lys15-octanoate-Esculentin-2CHa-(GA30) on body weight on body weight change (Day 0-Day 28) of Swiss TO mice on high fat diet; Values are mean±SEM (n=6 to 8). *p<0.05, p<0.01, *p<0.001 compared to lean saline. Δp<0.05, ΔΔp<0.01, ΔΔΔp<0.001 compared to high fat diet saline control.

In vivo anti-diabetic effects of Exendin-4, Esculentin-2CHa-(GA30), [D-Arg7, D-Lys15,D-Lys23]-esculentin-2CHa-(GA30), and Lys15-octanoate-Esculentin-2CHa-(GA30) were assessed using Swiss TO mice fed high fat diet, with appropriate controls (saline treated mice on standard diet or high fat diet). Twice-daily administration of Exendin-4, Esculentin-2CHa-(GA30), [D-Arg7, D-Lys15, D-Lys23]-esculentin-2CHa-(GA30), and Lys15-octanoate-Esculentin-2CHa-(GA30) over a period of 28 days resulted in significant reduction in body weight (from initial body weight before administration of peptides) compared to lean and high fat diet saline control mice ($p<0.05$, $p<0.001$, FIG. 40). This effect on body weight change was comparable to Exendin-4, a GLP-1 mimetic. Peptide administration did not alter cumulative energy intake over the period of 28 days (FIG. 41).

Example 3—Effects on Blood Glucose and Plasma Insulin Levels

Lys15-octanoate-Esculentin-2CHa-(GA30) reduced blood glucose levels markedly from day 6 while [D-Arg7, D-Lys15,D-Lys23]-esculentin-2CHa-(GA30) reduced blood glucose levels from day 21 ($p<0.05$, $p<0.01$). All peptides reduced blood glucose change compared to high fat diet saline control ($p<0.05$, $p<0.01$, FIG. 42, middle). Non-fasted terminal blood glucose levels were significantly lower in peptide treated groups compared to saline control and normalized to lean saline control levels ($p<0.01$, $p<0.001$, FIG. 42, lower). In high fat diet saline control mice, plasma insulin levels progressively increased reflecting the hyperinsulinaemic state in insulin resistance (FIG. 43). Esculentin-2CHa-(GA30) and Lys15-octanoate-Esculentin-2CHa-(GA30) treatment reduced plasma insulin levels significantly from day 12 (from day 18 for [D-Arg7, D-Lys15,D-Lys23]-esculentin-2CHa-(GA30)) compared to high fat diet saline control, with area under curve markedly lower than high fat diet saline control ($p<0.05$, FIG. 43). Non-fasted plasma insulin levels were markedly lower in peptide treated groups compared to high fat diet saline control ($p<0.05$, $p<0.01$, FIG. 43).

Example 4—Effects on Glucose Tolerance and Insulin Sensitivity

Exendin-4, Esculentin-2CHa-(GA30), [D-Arg7, D-Lys15,D-Lys23]-esculentin-2CHa-(GA30), and Lys15-octanoate-Esculentin-2CHa-(GA30) also improved glucose tolerance, with lowered plasma glucose and insulin levels (FIGS. 44 and 45). In high fat diet saline controls, blood glucose and plasma insulin levels significantly increased over 90 min, compared to lean saline control ($p<0.05$, $p<0.01$, FIGS. 44 and 45). High fat diet saline control mice displayed markedly high plasma glucose levels even after injection of insulin, compared to lean saline control mice, reflecting the degree of insulin resistance ($p<0.01$, $p<0.001$, FIG. 46). All peptides improved insulin sensitivity in a similar fashion to Exendin-4, compared to high fat diet saline control ($p<0.05$, $p<0.01$, $p<0.001$, FIG. 46). To assess whether the blood glucose lowering effects were not due to acute effects after injections, blood glucose profile over a 24 h period was monitored. Blood glucose levels over 24 h period were significantly raised in high fat diet saline control mice compared to lean saline controls ($p<0.05$, $p<0.01$). Peptides indeed reduced blood glucose levels after chronic 28 day administration compared to high fat diet saline control ($p<0.5$, FIG. 47).

Example 5—Effects on Fat Mass

Effects of high fat diet and peptide administration on fat mass were assessed by DXA scanning. Lean mass was unaltered by high fat diet or peptides (FIG. 48). However, high fat diet significantly increased fat mass and fat (%) compared to lean saline controls ($p<0.01$, $p<0.001$, FIG. 48).

Example 6—Effects on Islet Function

Islet function was assessed using islets isolated from all groups of mice. High fat diet affected the secretory response to glucose, GLP-1 and alanine. Peptide treatment restored glucose, GLP-1 and alanine responsiveness in islets, in a manner similar to Exendin-4 ($p<0.05$, $p<0.01$, FIG. 49).

Example 7—Effects on Islet Morphology

Islet morphometric analyses revealed that high fat diet significantly increased islet area, beta and alpha cell area compared to lean saline control ($p<0.001$, FIG. 50A). Exendin-4, Esculentin-2CHa-(GA30), [D-Arg7, D-Lys15,D-Lys23]-esculentin-2CHa-(GA30), and Lys15-octanoate-Esculentin-2CHa-(GA30) significantly reduced islet area, beta and alpha cell area compared to high fat diet saline control ($p<0.001$, FIG. 50B). Number of islets per $mm^2$ of pancreas section was increased in high fat saline control, compared to lean saline control ($p<0.05$, FIG. 51, upper). Assessment of islet size distribution showed that high fat diet increased proportion of large sized islets while decreasing proportion of small islets, compared to lean saline control (FIG. 51, lower). In peptide treated groups of mice, proportion of large sized islets decreased compared to high fat diet saline control (FIG. 51, lower).

Example 8—Effects on Plasma Lipid Profile

High fat diet significantly increased LDL levels compared to lean saline control ($p<0.01$, FIG. 52A). Chronic administration of peptides did not affect total cholesterol, HDL or triglyceride levels in high fat fed mice (FIGS. 52A and 52B). However, Lys15-octanoate-Esculentin-2CHa-(GA30) treatment reduced LDL levels compared to high fat diet saline control ($p<0.05$, FIG. 52A).

The peptides and peptide analogues of the present invention stimulate insulin-release in a concentration-dependent manner from glucose responsive clonal pancreatic cell-line, BRIN-DB11. Esculentin-2CHa(GA30), the shortest version of the synthetic analogue appears to be more potent than the native peptide at lower concentrations. These effects were not associated with beta cell cytotoxicity. These observations together with the lack of haemolytic effects of these peptides further suggest that administration of these peptides in human may be safe.

Without being bound by theory, by incubating BRIN-BD11 cells with the known modulators of insulin release in the absence or presence of the peptides and peptide analogues of the present invention (10-6M), it was shown that the stimulatory effect of the peptides was inhibited in the presence of verapamil (50 µM) and chelation of extracellular calcium but completely abolished in the presence of diazoxide (200 µM). Moreover, insulin secretion increased with the co-incubation of the peptide with IBMX (200 µM), and tolbutamide (200 µM).

The effect of the peptides on membrane depolarization and intracellular calcium concentration (two processes that are critical to physiologic insulin secretion) was also investigated. Results obtained revealed that esculentin-2CHa significantly enhanced membrane depolarization and caused an increase in intracellular calcium. These results suggest that the actions of esculentin-2CHa and its analogues are physiologic and may involve well-known pathways of insulin secretion. Esculentin-2CHa and its analogues significantly reduced plasma glucose and increase plasma insulin concentrations in mice with diet-induced obesity diabetes following intraperitoneal injection of high glucose load. These observations further confirm the involvement of the $K_{ATP}$-dependent pathway in the actions of the peptides.

All the peptides were degraded within 2 hours of incubation with mouse plasma as shown by HPLC and MALDI-TOF profiles obtained for intact peptides and their degraded products.

Esculentin-2CHa significantly reduced plasma glucose concentration in mice with diet-induced obesity diabetes following intraperitoneal injection of high glucose load. Acute in vivo effects of esculentin-2CHa-(GA30) and [Lys20,Lys27.Ser31,Ser37]-esculentin-2CHa were comparable to the effects of native esculentin-CHa. Plasma insulin concentration was significantly increased in mice injected with the native esculentin-2CHa, esculentin-2CHa-(GA30) [Lys20, Lys27]-esculentin-2CHa-(GA30) and [Lys20, Lys27.Ser31,Ser37]-esculentin-2CHa.

Peptides of the present invention exerted anti-diabetic effects in high fat fed mice when administered twice-daily over a period of 28 days. The effects were comparable to Exendin-4 in reducing body weight, lowering blood glucose levels, improving glucose tolerance and insulin sensitivity, islet function and islet cell distribution. Peptide administration did not affect plasma amylase or liver function in all groups of mice.

The invention claimed is:

1. An isolated esculentin-2CHa peptide or analogue thereof, comprising:
   (i) at least 30 amino acid residues corresponding to at least the first 30 amino acids from the N-terminal end of the esculentin-2CHa peptide; and
   (ii) at least one amino acid substitution or modification selected from the group consisting of:
      (a) an amino acid substitution or modification at position 7 wherein the amino acid substitution is substitution with the D-isomer of arginine (D-Arg);
      (b) an amino acid substitution or modification at position 15 selected from at least one of the group consisting of:
         substitution with the D-isomer of lysine (D-Lys);
         substitution with ornithine; and
         modification by addition of a fatty acid to the amino acid residue;
      (c) an amino acid substitution or modification at position 23 selected from at least one of the group consisting of:
         substitution with the D-isomer of lysine (D-Lys);
         substitution with ornithine; and
         modification by addition of a fatty acid to the amino acid residue; and
      (d) an amino acid substitution or modification at position 30, wherein the amino acid modification is addition of an amide group.

2. The isolated esculentin-2CHa peptide or analogue thereof according to claim 1, wherein the peptide or peptide analogue comprises at least 37 amino acid residues corresponding to at least the first 37 amino acids from the N-terminal end of the esculentin-2CHa peptide.

3. The isolated esculentin-2CHa peptide or analogue thereof according to claim 1, further comprising at least one additional amino acid substitution or modification selected from the group consisting of:
   (a) an amino acid substitution or modification at position 31; and
   (b) an amino acid substitution or modification at position 37.

4. The isolated esculentin-2CHa peptide or analogue thereof according to claim 1, wherein the amino acid substitution or modification at position 15 is modification by addition of a fatty acid to the amino acid residue, wherein the fatty acid is a medium-chain fatty acid having 6-12 carbon atoms.

5. The isolated esculentin-2CHa peptide or analogue thereof according to claim 1, wherein the amino acid substitution or modification at position 23 is modification by addition of a fatty acid to the amino acid residue, wherein the fatty acid is a medium-chain fatty acid having 6-12 carbon atoms.

6. The isolated esculentin-2CHa peptide or analogue thereof according to claim 2, comprising an amino acid substitution or modification at position 31, wherein the amino acid substitution at position 31 is substitution with serine (Ser).

7. The isolated esculentin-2CHa peptide or analogue thereof according to claim 2, comprising an amino acid substitution or modification at position 37, wherein the amino acid substitution at position 37 is substitution with serine (Ser).

8. A pharmaceutical composition comprising an esculentin-2CHa peptide or analogue thereof according to claim 1, and a pharmaceutically acceptable carrier.

9. The pharmaceutical composition according to claim 8, wherein the peptide or peptide analogue is in the form of a pharmaceutically acceptable salt.

10. A method of treating a subject that has at least one disease selected from the group consisting of diabetes, insulin resistance, obesity, and hypercholesterolemia, comprising administering a pharmaceutically acceptable amount of the pharmaceutical composition according to claim 8 to the subject, thereby treating the disease in the subject.

11. The method according to claim 10, wherein the subject has diabetes, and wherein the diabetes is type 2 diabetes.

12. The method according to claim 10, comprising administering to the subject of 75 nmol/kg body weight of the esculentin-2CHa peptide or analogue thereof in the pharmaceutical composition.

13. The isolated esculentin-2CHa peptide or analogue thereof according to claim 1, comprising:
   the amino acid substitution at position 7, wherein the amino acid substitution is substitution with the D-isomer of arginine (D-Arg).

14. The isolated esculentin-2CHa peptide or analogue thereof according to claim 1, comprising:
   the amino acid substitution at position 15, wherein the amino acid substitution is substitution with the D-isomer of lysine (D-Lys).

15. The isolated esculentin-2CHa peptide or analogue thereof according to claim 1, comprising:
   the amino acid substitution at position 23, wherein the substitution is substitution with the D-isomer of lysine (D-Lys).

16. The isolated esculentin-2CHa peptide or analogue thereof according to claim 1, comprising:
   the amino acid substitution at position 15, wherein the substitution is substitution with the D-isomer of lysine (D-Lys); and the amino acid substitution at position 23, wherein is substitution is substitution with the D-isomer of lysine (D-Lys).

17. The isolated esculentin-2CHa peptide or analogue thereof according to claim 1, comprising:
   the amino acid substitution at position 7, wherein the amino acid substitution is substitution with the D-isomer of arginine (D-Arg);
   the amino acid substitution at position 15, wherein the amino acid substitution is substitution with the D-isomer of lysine (D-Lys); and
   the amino acid substitution or modification at position 23, wherein the amino acid substation is substitution with the D-isomer of lysine (D-Lys).

18. The isolated esculentin-2CHa peptide or analogue thereof according to claim 1, comprising:
   the amino acid modification at position 30, wherein the amino acid modification is addition of an amide group.

* * * * *

SEQUENCE LISTING

```
<160> NUMBER OF SEQ ID NOS: 15

<210> SEQ ID NO 1
<211> LENGTH: 37
<212> TYPE: PRT
<213> ORGANISM: Lithobathes chiricahuensis

<400> SEQUENCE: 1

Gly Phe Ser Ser Ile Phe Arg Gly Val Ala Lys Phe Ala Ser Lys Gly
1               5                   10                  15

Leu Gly Lys Asp Leu Ala Lys Leu Gly Val Asp Leu Val Ala Cys Lys
            20                  25                  30

Ile Ser Lys Gln Cys
        35

<210> SEQ ID NO 2
<211> LENGTH: 30
<212> TYPE: PRT
<213> ORGANISM: Lithobathes chiricahuensis

<400> SEQUENCE: 2

Gly Phe Ser Ser Ile Phe Arg Gly Val Ala Lys Phe Ala Ser Lys Gly
1               5                   10                  15

Leu Gly Lys Asp Leu Ala Lys Leu Gly Val Asp Leu Val Ala
            20                  25                  30

<210> SEQ ID NO 3
<211> LENGTH: 30
<212> TYPE: PRT
<213> ORGANISM: Lithobathes chiricahuensis

<400> SEQUENCE: 3

Gly Phe Ser Ser Ile Phe Arg Gly Val Ala Lys Phe Ala Ser Lys Gly
1               5                   10                  15

Leu Gly Lys Asp Leu Ala Lys Leu Gly Val Asp Leu Val Ala
            20                  25                  30

<210> SEQ ID NO 4
<211> LENGTH: 30
<212> TYPE: PRT
<213> ORGANISM: Lithobathes chiricahuensis
```

```
<400> SEQUENCE: 4

Gly Phe Ser Ser Ile Phe Arg Gly Val Ala Lys Phe Ala Ser Lys Gly
1               5                   10                  15

Leu Gly Lys Asp Leu Ala Lys Leu Gly Val Asp Leu Val Ala
            20                  25                  30

<210> SEQ ID NO 5
<211> LENGTH: 30
<212> TYPE: PRT
<213> ORGANISM: Lithobathes chiricahuensis

<400> SEQUENCE: 5

Gly Phe Ser Ser Ile Phe Arg Gly Val Ala Lys Phe Ala Ser Lys Gly
1               5                   10                  15

Leu Gly Lys Asp Leu Ala Lys Leu Gly Val Asp Leu Val Ala
            20                  25                  30

<210> SEQ ID NO 6
<211> LENGTH: 30
<212> TYPE: PRT
<213> ORGANISM: Lithobathes chiricahuensis

<400> SEQUENCE: 6

Gly Phe Ser Ser Ile Phe Arg Gly Val Ala Lys Phe Ala Ser Lys Gly
1               5                   10                  15

Leu Gly Lys Asp Leu Ala Lys Leu Gly Val Asp Leu Val Ala
            20                  25                  30

<210> SEQ ID NO 7
<211> LENGTH: 30
<212> TYPE: PRT
<213> ORGANISM: Lithobathes chiricahuensis

<400> SEQUENCE: 7

Gly Phe Ser Ser Ile Phe Arg Gly Val Ala Lys Phe Ala Ser Lys Gly
1               5                   10                  15

Leu Gly Lys Asp Leu Ala Lys Leu Gly Val Asp Leu Val Ala
            20                  25                  30

<210> SEQ ID NO 8
<211> LENGTH: 28
<212> TYPE: PRT
<213> ORGANISM: Lithobathes chiricahuensis

<400> SEQUENCE: 8

Gly Phe Ser Ser Ile Phe Arg Gly Val Ala Lys Phe Ala Ser Gly Leu
1               5                   10                  15

Gly Lys Asp Leu Ala Leu Gly Val Asp Leu Val Ala
            20                  25

<210> SEQ ID NO 9
<211> LENGTH: 30
<212> TYPE: PRT
<213> ORGANISM: Lithobathes chiricahuensis

<400> SEQUENCE: 9

Gly Phe Ser Ser Ile Phe Arg Gly Val Ala Lys Phe Ala Ser Lys Gly
1               5                   10                  15

Leu Gly Lys Asp Leu Ala Lys Leu Gly Val Asp Leu Val Ala
            20                  25                  30
```

<210> SEQ ID NO 10
<211> LENGTH: 30
<212> TYPE: PRT
<213> ORGANISM: Lithobathes chiricahuensis

<400> SEQUENCE: 10

Gly Phe Ser Ser Ile Phe Arg Gly Val Ala Lys Phe Ala Ser Lys Gly
1               5                   10                  15

Leu Gly Lys Asp Leu Ala Lys Leu Gly Val Asp Leu Val Ala
            20                  25                  30

<210> SEQ ID NO 11
<211> LENGTH: 30
<212> TYPE: PRT
<213> ORGANISM: Lithobathes chiricahuensis

<400> SEQUENCE: 11

Gly Phe Ser Ser Ile Phe Arg Gly Val Ala Lys Phe Ala Ser Lys Gly
1               5                   10                  15

Leu Gly Lys Asp Leu Ala Lys Leu Gly Val Asp Leu Val Ala
            20                  25                  30

<210> SEQ ID NO 12
<211> LENGTH: 30
<212> TYPE: PRT
<213> ORGANISM: Lithobathes chiricahuensis

<400> SEQUENCE: 12

Gly Phe Ser Ser Ile Phe Arg Gly Val Ala Lys Phe Ala Ser Lys Gly
1               5                   10                  15

Leu Gly Lys Lys Leu Ala Lys Leu Gly Val Lys Leu Val Ala
            20                  25                  30

<210> SEQ ID NO 13
<211> LENGTH: 37
<212> TYPE: PRT
<213> ORGANISM: Lithobathes chiricahuensis

<400> SEQUENCE: 13

Gly Phe Ser Ser Ile Phe Arg Gly Val Ala Lys Phe Ala Ser Lys Gly
1               5                   10                  15

Leu Gly Lys Lys Leu Ala Lys Leu Gly Val Lys Leu Val Ala Cys Lys
            20                  25                  30

Ile Ser Lys Gln Cys
        35

<210> SEQ ID NO 14
<211> LENGTH: 37
<212> TYPE: PRT
<213> ORGANISM: Lithobathes chiricahuensis

<400> SEQUENCE: 14

Gly Phe Ser Ser Ile Phe Arg Gly Val Ala Lys Phe Ala Ser Lys Gly
1               5                   10                  15

Leu Gly Lys Asp Leu Ala Lys Leu Gly Val Asp Leu Val Ala Ser Lys
            20                  25                  30

Ile Ser Lys Gln Ser
        35

<210> SEQ ID NO 15
<211> LENGTH: 37

```
<212> TYPE: PRT
<213> ORGANISM: Lithobathes chiricahuensis

<400> SEQUENCE: 15

Gly Phe Ser Ser Ile Phe Arg Gly Val Ala Lys Phe Ala Ser Lys Gly
1               5                   10                  15

Leu Gly Lys Lys Leu Ala Lys Leu Gly Val Lys Leu Val Ala Ser Lys
            20                  25                  30

Ile Ser Lys Gln Ser
            35
```